(12) United States Patent
Fleury et al.

(10) Patent No.: US 10,315,984 B2
(45) Date of Patent: *Jun. 11, 2019

(54) NEPRILYSIN INHIBITORS

(71) Applicant: THERAVANCE BIOPHARMA R&D IP, LLC, South San Francisco, CA (US)

(72) Inventors: Melissa Fleury, Brisbane, CA (US); Adam D. Hughes, Half Moon Bay, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/843,427

(22) Filed: Dec. 15, 2017

(65) Prior Publication Data

US 2018/0327350 A1 Nov. 15, 2018

Related U.S. Application Data

(63) Continuation of application No. 15/581,327, filed on Apr. 28, 2017, now Pat. No. 9,884,807, which is a
(Continued)

(51) Int. Cl.
C07C 229/22 (2006.01)
C07D 249/04 (2006.01)
C07D 401/04 (2006.01)
C07D 405/12 (2006.01)
A61K 31/42 (2006.01)
A61K 31/4196 (2006.01)
A61K 31/415 (2006.01)
A61K 45/06 (2006.01)
C07D 257/04 (2006.01)
C07D 231/14 (2006.01)
C07C 271/22 (2006.01)
C07D 263/38 (2006.01)
C07D 261/18 (2006.01)
C07D 249/18 (2006.01)
A61K 31/4192 (2006.01)
C07D 231/20 (2006.01)
(Continued)

(52) U.S. Cl.
CPC ............ C07C 229/22 (2013.01); A61K 31/41 (2013.01); A61K 31/415 (2013.01); A61K 31/4155 (2013.01); A61K 31/4192 (2013.01); A61K 31/4196 (2013.01); A61K 31/42 (2013.01); A61K 31/4439 (2013.01); A61K 31/675 (2013.01); A61K 45/06 (2013.01); C07C 271/22 (2013.01); C07D 207/26 (2013.01); C07D 231/14 (2013.01); C07D 231/18 (2013.01); C07D 231/20 (2013.01); C07D 249/04 (2013.01); C07D 249/12 (2013.01); C07D 249/18 (2013.01); C07D 253/08 (2013.01); C07D 257/04 (2013.01); C07D 261/18 (2013.01); C07D 263/38 (2013.01); C07D 401/04 (2013.01); C07D 405/12 (2013.01); C07D 405/14 (2013.01); C07F 9/65031 (2013.01)

(58) Field of Classification Search
None
See application file for complete search history.

(56) References Cited

U.S. PATENT DOCUMENTS 4,189,604 A 2/1980 Umezawa et al.
4,206,232 A 6/1980 Ondetti et al.
(Continued)

FOREIGN PATENT DOCUMENTS

WO 2011/088797 A1 7/2011

OTHER PUBLICATIONS

Ksander et al., "Dicarboxylic acid dipeptide neutral endopeptidase inhibitors", Journal of Medicinal Chemistry, 38 (10): 1689-1700 (1995).
(Continued)

Primary Examiner — Kamal A Saeed
(74) Attorney, Agent, or Firm — Jeffrey A. Hagenah

(57) ABSTRACT

In one aspect, the invention relates to compounds having the formula XII:

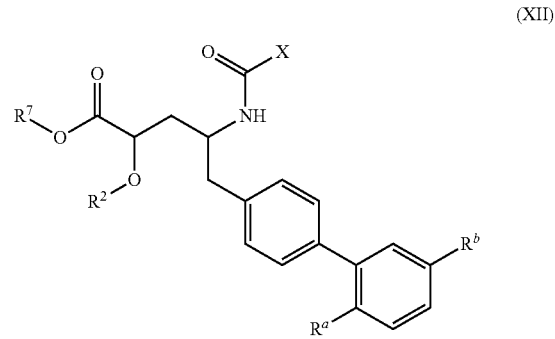

(XII)

where $R^a$, $R^b$, $R^2$, $R^7$, and X are as defined in the specification, or a pharmaceutically acceptable salt thereof. The compounds described herein are prodrugs of compounds having neprilysin inhibition activity. In another aspect, the invention relates to pharmaceutical compositions comprising these compounds; methods of using these compounds; and processes and intermediates for preparing these compounds.

3 Claims, No Drawings

Related U.S. Application Data continuation of application No. 14/792,810, filed on Jul. 7, 2015, now Pat. No. 9,670,140, which is a continuation of application No. 13/911,819, filed on Jun. 6, 2013, now Pat. No. 9,108,934.

(60) Provisional application No. 61/773,969, filed on Mar. 7, 2013, provisional application No. 61/657,229, filed on Jun. 8, 2012.

(51) Int. Cl.
*A61K 31/4155* (2006.01)
*A61K 31/4439* (2006.01)
*C07D 405/14* (2006.01)
*C07D 249/12* (2006.01)
*A61K 31/41* (2006.01)
*A61K 31/675* (2006.01)
*C07F 9/6503* (2006.01)
*C07D 231/18* (2006.01)
*C07D 253/08* (2006.01)
*C07D 207/26* (2006.01)

(56) References Cited

U.S. PATENT DOCUMENTS

| | | |
|---|---|---|
| 4,374,829 A | 2/1983 | Harris et al. |
| 4,513,009 A | 4/1985 | Roques et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 9/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,686,184 B2 | 4/2014 | Fleury et al. |
| 8,691,868 B2 | 4/2014 | Hughes et al. |
| 9,045,443 B2 | 6/2015 | Mammen et al. |
| 9,108,934 B2 | 8/2015 | Hughes et al. |
| 9,670,140 B2 | 6/2017 | Hughes et al. |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0309724 A1 | 12/2012 | Fleury et al. |

OTHER PUBLICATIONS

Misawa et al., "Structure-based design of dipeptide derivatives for the human neutral endopeptidase", BioOrganic & Medicinal Chemistry, 19: 5935-5947 (2011).
PCT International Search Report for PCT/US2013/044546 dated Aug. 16, 2013.

NEPRILYSIN INHIBITORS

CROSS-REFERENCE TO RELATED APPLICATIONS

This application is a continuation of U.S. application Ser. No. 15/581,327, filed on Apr. 28, 2017, now allowed; which is a continuation of U.S. application Ser. No. 14/792,810, filed on Jul. 7, 2015, now U.S. Pat. No. 9,670,140; which is a continuation of U.S. application Ser. No. 13/911,819, filed on Jun. 6, 2013, now U.S. Pat. No. 9,108,934; which application claims the benefit of U.S. Provisional Application No. 61/657,229, filed on Jun. 8, 2012 and U.S. Provisional Application No. 61/773,969, filed on Mar. 7, 2013; the entire disclosures of which are incorporated herein by reference.

BACKGROUND OF THE INVENTION

Field of the Invention

The present invention relates to novel compounds which are metabolized in vivo to compounds having activity as neprilysin inhibitors. The invention also relates to pharmaceutical compositions comprising these compounds, processes and intermediates for preparing these compounds and methods of using these compounds to treat diseases such as hypertension, heart failure, pulmonary hypertension, and renal disease.

State of the Art

Commonly-assigned U.S. Patent Publication No. 2012/0157383, filed on Dec. 14, 2011 to Gendron et al., describes novel compounds that have activity as neprilysin inhibitors, the disclosure of which is incorporated herein by reference. In particular, compounds of the genus:

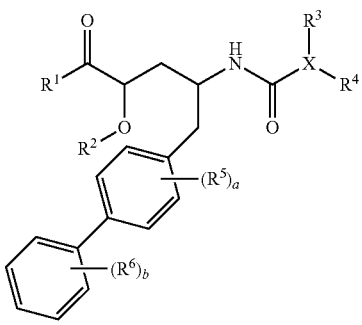

are described. Depending upon the variables, compounds within this genus can be referred to as being in the active form or as being a prodrug, which is metabolized in vivo to generate the active form of the compound.

In spite of these compounds however, there remains a need for compounds and prodrugs within this genus that have different metabolic and cleavage properties. For example, there remains a need for active compounds and/or prodrug compounds having improved oral absorption and for prodrug compounds that undergo rapid cleavage to form the active compound. This invention is directed to that need.

SUMMARY OF THE INVENTION

One aspect of the invention relates to a compound of formula XII:

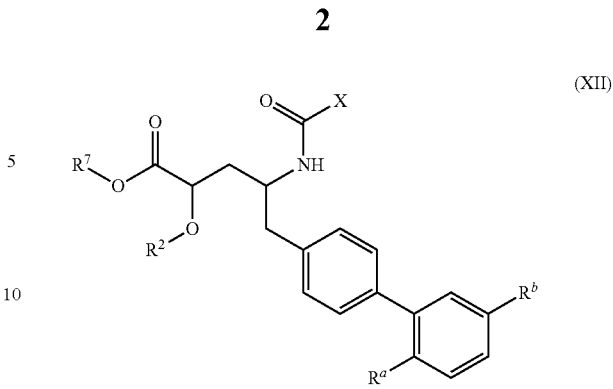

where:
(i) $R^a$ is H; $R^b$ is Cl; X is

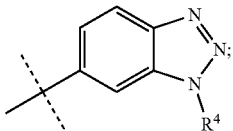

and
$R^2$ is H, $R^4$ is —OH, and $R^7$ is selected from —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

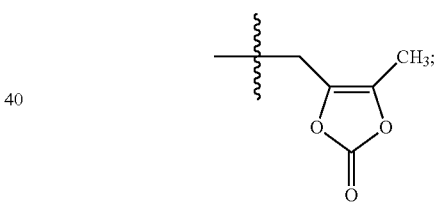

or $R^2$ is H, $R^4$ is selected from —O-benzyl, —OCHR$^c$OC(O)—C$_{1-4}$alkyl, —OCH$_2$OC(O)CHR$^d$—NH$_2$, and —OCH$_2$OC(O)CHR$^d$—NHC(O)O—C$_{1-6}$alkyl, and $R^7$ is selected from H and —CH$_2$OC(O)CH$_3$; or $R^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, $R^4$ is —OH, and $R^7$ is H; or
(ii) $R^a$ is H; $R^b$ is Cl; X is

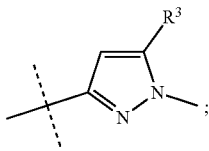

and
$R^2$ is H, $R^3$ is —OH and $R^7$ is selected from —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

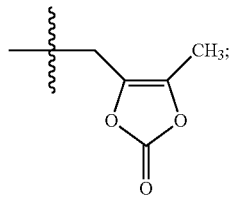 [SMILES: *Cc1oc(=O)oc1C]

or R$^3$ is selected from —OC(O)CH$_2$CH$_3$, —OC(O)CH$_2$CH(CH$_3$)$_2$, —OC(O)-phenyl, —OCH$_2$OC(O)CHR$^d$—NH$_2$, and —OCH$_2$OC(O)CHR$^d$—NHC(O)O—C$_{1-6}$alkyl, and R$^7$ is H; or R$^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, R$^3$ is —OH, and R$^7$ is H; or (iii) IV is H; R$^b$ is Cl; X is

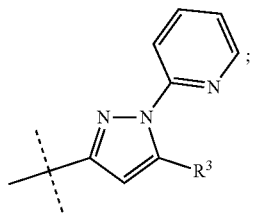

and
R$^2$ is H, R$^3$ is —OH and R$^7$ is selected from —CH$_2$CH$_3$, —CH$_2$CH(CH$_3$)$_2$, —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

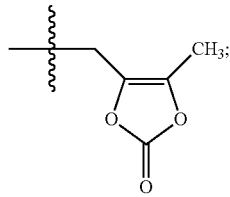 [SMILES: *Cc1oc(=O)oc1C]

or R$^2$ is H, R$^3$ is selected from —OC(O)CH$_2$CH$_3$, —OC(O)CH$_2$CH(CH$_3$)$_2$, —OC(O)-phenyl, —OCH$_2$OC(O)CHR$^d$—NH$_2$, and —OCH$_2$OC(O)CHR$^d$—NHC(O)O—C$_{1-6}$alkyl, and R$^7$ is H; or R$^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, R$^3$ is —OH, and R$^7$ is H; or (iv) IV is F; R$^b$ is Cl; X is

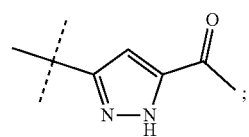

and R$^2$ is H and R$^7$ is selected from H, —CH$_2$CH$_3$, —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

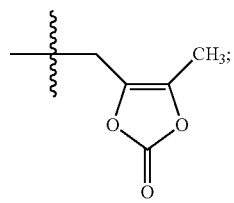 [SMILES: *Cc1oc(=O)oc1C]

or R$^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, and R$^7$ is H; or (v) R$^a$ is H; R$^b$ is Cl; X is

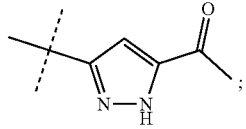

and
R$^2$ is H and R$^7$ is selected from H, —CH$_2$CH$_3$, —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

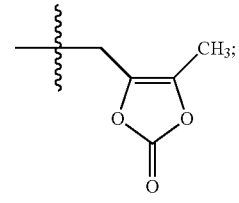 [SMILES: *Cc1oc(=O)oc1C]

or R$^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, and R$^7$ is H; or (vi) R$^a$ is H; R$^b$ is Cl; X is

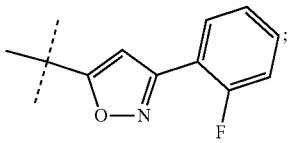

and
R$^2$ is H and R$^7$ is selected from H, —CH$_2$CH$_3$, —CH$_2$CF$_3$, —(CH$_2$)$_2$CF$_3$, —CH$_2$CF$_2$CH$_3$, —CH$_2$CF$_2$CF$_3$, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH₃)₂, —CH₂OC(O)CHR$^d$—NH₂, —CH₂OC(O)CHR$^d$—NHC(O)O—C$_{1-6}$alkyl, benzyl, and

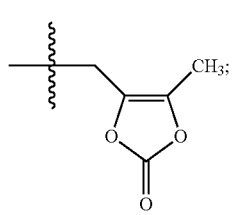 [SMILES: *Cc1oc(=O)oc1C]

or R² is selected from —C(O)—C$_{1-6}$alkyl, —C(O)CHR$^d$—NH₂, —C(O)CHR$^d$—NHC(O)O—C$_{1-6}$alkyl, and —P(O)(OR$^e$)₂, and R⁷ is H; or (vii) R$^a$ is H; R$^b$ is Cl; X is

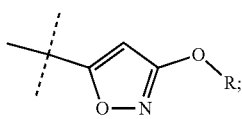

R is H or —CH₃; and

R² is H and R⁷ is selected from —CH₂CH₃, —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH₃)₂, —CH₂OC(O)CHR$^d$—NH₂, —CH₂OC(O)CHR$^d$—NHC(O)O—C$_{1-6}$alkyl, benzyl, and

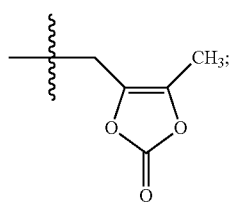 [SMILES: *Cc1oc(=O)oc1C]

or R² is selected from —C(O)—C$_{1-6}$alkyl, —C(O)CHR$^d$—NH₂, —C(O)CHR$^d$—NHC(O)O—C$_{1-6}$alkyl, and —P(O)(OR$^e$)₂, and R⁷ is H; or (viii) R$^a$ is F; R$^b$ is Cl; X is

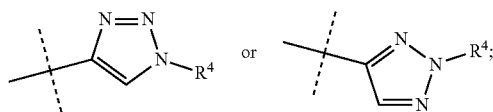

and

R² is H, R⁴ is —OH, and R⁷ is selected from —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH₃)₂, —CH₂OC(O)CHR$^d$—NH₂, —CH₂OC(O)CHR$^d$—NHC(O)O—C$_{1-6}$alkyl, benzyl, and

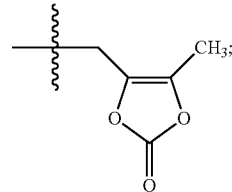 [SMILES: *Cc1oc(=O)oc1C]

or R² is H, R⁴ is selected from —O-benzyl, —OCHR$^c$OC(O)—C$_{1-4}$alkyl, —OCH₂OC(O)CH[CH(CH₃)₂]NH₂, —OCH₂OC(O)CH[CH(CH₃)₂]—NHC(O)OCH₃ and

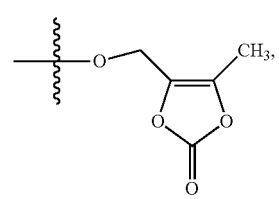

and R⁷ is H; or R² is selected from —C(O)—C$_{1-6}$alkyl, —C(O)CHR$^d$—NH₂, —C(O)CHR$^d$—NHC(O)O—C$_{1-6}$alkyl, and —P(O)(OR$^e$)₂, R⁴ is —OH, and R⁷ is H; or (ix) R$^a$ is H; R$^b$ is Cl; X is

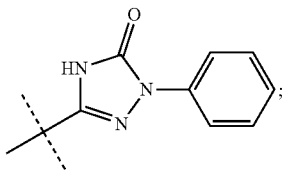

and

R² is H and R⁷ is selected from —CH₂CH₃, —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH₃)₂, —CH₂OC(O)CHR$^d$—NH₂, —CH₂OC(O)CHR$^d$—NHC(O)O—C$_{1-6}$alkyl, benzyl, and

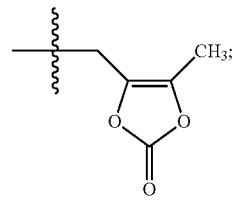 [SMILES: *Cc1oc(=O)oc1C]

or R² is selected from —C(O)—C$_{1-6}$alkyl, —C(O)CHR$^d$—NH₂, —C(O)CHR$^d$—NHC(O)O—C$_{1-6}$alkyl, and —P(O)(OR$^e$)₂, and R⁷ is H; or (x) $R^a$ is H; $R^b$ is H; X is

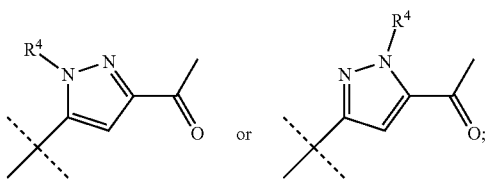

and $R^2$ and $R^4$ are H, and $R^7$ is selected from —$CH_2CF_3$, —$(CH_2)_2CF_3$, —$CH_2CF_2CH_3$, —$CH_2CF_2CF_3$, —$C(CH_3)(CF_3)_2$, —$CH(CH_2CH_3)CF_3$, —$CH(CH_3)CF_2CF_3$, —$(CH_2)_{2-3}OH$, —$CH_2CH(NH_2)COOCH_3$, $CHR^c OC(O)$—$C_{1-4}$alkyl, —$CHR^c OC(O)O$—$C_{2-4}$alkyl, —$CHR^c OC(O)O$-cyclohexyl, —$C_{2-4}$alkylene-$N(CH_3)_2$, —$CH_2OC(O)CHR^d$—$NH_2$, —$CH_2OC(O)CHR^d$—$NHC(O)O$—$C_{1-6}$alkyl, and benzyl; or $R^2$ is H, $R^4$ is selected from —$CH_2OC(O)CH[CH(CH_3)_2]$—$NHC(O)OCH_3$ and —$CH_2OC(O)CH[CH(CH_3)_2]NH_2$, and $R^7$ is H; or $R^2$ is selected from —$C(O)$—$C_{1-6}$alkyl, —$C(O)CHR^d$—$NH_2$, —$C(O)CHR^d$—$NHC(O)O$—$C_{1-6}$alkyl, and —$P(O)(OR^e)_2$, $R^4$ is H, and $R^7$ is H; or $R^2$ is H, $R^4$ is —$CH_2OP(O)(OR^e)_2$ or —$CH_2OC(O)CH[CH(CH_3)_2]NH_2$, and $R^7$ is —$CH_2CH_3$; or $R^2$ is —$C(O)CH[CH(CH_3)_2]NH_2$, $R^4$ is H, and $R^7$ is —$CH_2CH_3$; or (xi) $R^a$ is H; $R^b$ is Cl; X is

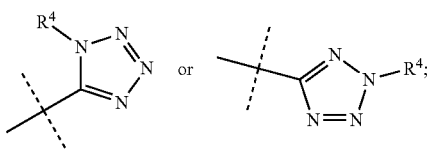

and $R^2$ and $R^4$ are H, and $R^7$ is selected from H, —$CH_2CH_3$, —$CH_2CF_3$, —$(CH_2)_2CF_3$, —$CH_2CF_2CH_3$, —$CH_2CF_2CF_3$, —$C(CH_3)(CF_3)_2$, —$CH(CH_2CH_3)CF_3$, —$CH(CH_3)CF_2CF_3$, —$(CH_2)_{2-3}OH$, —$CH_2CH(NH_2)COOCH_3$, —$(CH_2)_2OCH_3$, —$CHR^c OC(O)$—$C_{1-4}$alkyl, —$CHR^c OC(O)O$—$C_{2-4}$alkyl, —$CHR^c OC(O)O$-cyclohexyl, —$C_{2-4}$alkylene-$N(CH_3)_2$, —$CH_2OC(O)CHR^d$—$NH_2$, —$CH_2OC(O)CHR^d$—$NHC(O)O$—$C_{1-6}$alkyl, and benzyl; or $R^2$ is H, $R^4$ is selected from —$CH_2OC(O)CH[CH(CH_3)_2]$—$NHC(O)OCH_3$ and —$CH_2OC(O)CH[CH(CH_3)_2]NH_2$, and $R^7$ is H; or $R^2$ is selected from —$C(O)$—$C_{1-6}$alkyl, —$C(O)CHR^d$—$NH_2$, —$C(O)CHR^d$—$NHC(O)O$—$C_{1-6}$alkyl, and —$P(O)(OR^e)_2$, $R^4$ is H, and $R^7$ is H; or $R^2$ is H, $R^4$ is —$CH_2OP(O)(OR^e)_2$ or —$CH_2OC(O)CH[CH(CH_3)_2]NH_2$, and $R^7$ is —$CH_2CH_3$; or $R^2$ is —$C(O)CH[CH(CH_3)_2]NH_2$, $R^4$ is H, and $R^7$ is —$CH_2CH_3$;

where each $R^c$ is independently H or —$C_{1-3}$alkyl; each $R^d$ is independently H, —$CH_3$, —$CH(CH_3)_2$, phenyl, or benzyl; and each $R^e$ is independently H, —$C_{1-6}$alkyl, or phenyl;

or a pharmaceutically acceptable salt thereof.

The present invention provides compounds which are metabolized in vivo to compounds that have been found to possess neprilysin (NEP) enzyme inhibition activity. Accordingly, compounds of the invention are expected to be useful and advantageous as therapeutic agents for treating patients suffering from a disease or disorder that is treated by inhibiting the NEP enzyme or by increasing the levels of its peptide substrates. Thus, one aspect of the invention relates to a method of treating hypertension, heart failure, or renal disease, comprising administering to a patient a therapeutically effective amount of a compound of the invention.

Another aspect of the invention relates to pharmaceutical compositions comprising a pharmaceutically acceptable carrier and a compound of the invention.

Yet another aspect of the invention relates to processes and intermediates useful for preparing compounds of the invention. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process.

Yet another aspect of the invention relates to the use of a compound of formula I or a pharmaceutically acceptable salt thereof, for the manufacture of a medicament, especially for the manufacture of a medicament useful for treating hypertension, heart failure, or renal disease. Another aspect of the invention relates to use of a compound of the invention for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-6}$alkyl, meaning an alkyl group having from 1 to 6 carbon atoms where the carbon atoms are in any acceptable configuration. Representative alkyl groups include, by way of example, methyl, ethyl, n-propyl, isopropyl, n-butyl, s-butyl, isobutyl, t-butyl, n-pentyl, n-hexyl, and the like.

As used herein, the phrase "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

As used herein, the term "prodrug" is intended to mean an inactive (or significantly less active) precursor of a drug that is converted into its active form in the body under physiological conditions, for example, by normal metabolic processes. Such compounds may not necessarily possess pharmacological activity at NEP, but may be administered orally or parenterally and thereafter metabolized in the body to form a compound that is pharmacologically active at NEP.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

The compound of the invention contain one or more chiral centers and therefore, these compounds may be prepared and used in various stereoisomeric forms. In some embodiments, in order to optimize the therapeutic activity of the compounds of the invention, e.g., to treat hypertension, it may be desirable that the carbon atoms have a particular (R,R), (S,S), (S,R), or (R,S) configuration or are enriched in a stereoisomeric form having such configuration. In other embodiments, the compounds of the invention are present as racemic mixtures. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, $^{15}$N, $^{18}$O, $^{17}$O, $^{35}$S, $^{36}$Cl, and $^{18}$F. Of particular interest are compounds of formula I enriched in tritium or carbon-14 which can be used, for example, in tissue distribution studies; compounds of the invention enriched in deuterium especially at a site of metabolism resulting, for example, in compounds having greater metabolic stability; and compounds of formula I enriched in a positron emitting isotope, such as $^{11}$C, $^{18}$F, $^{15}$O an $^{13}$N, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

U.S. Patent Publication No. 2012/0157383 specifically disclosed (2R,4R)-5-(3'-chlorobiphenyl-4-yl)-2-hydroxy-4-[(3-hydroxy-3H-benzotriazole-5-carbonyl)amino]pentanoic acid, which is represented by formula I':

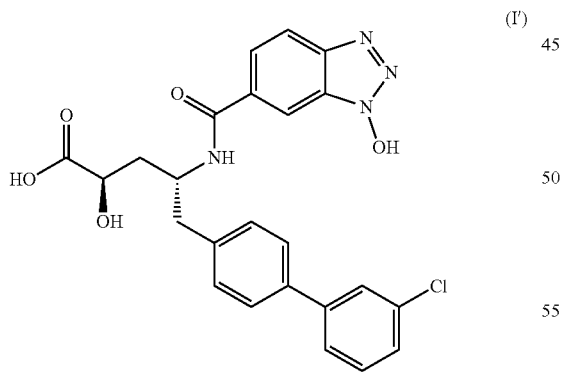

(I')

In one embodiment, this compound is referred to as the active form and is administered as a prodrug, which is metabolized in vivo to form the compound of formula I'. U.S. Patent Publication No. 2012/0157383 also disclosed the ethyl ester prodrug of the compound of formula I'.

One aspect of the invention relates to other prodrugs of the compound of formula I'. These prodrugs are represented by formula XII, where $R^a$ is H, $R^b$ is Cl, and X is:

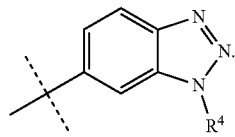

In one embodiment, these compounds are represented by formula I:

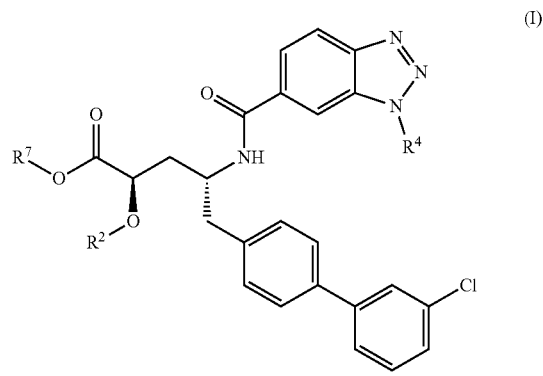

(I)

where $R^2$ is H, $R^4$ is —OH, and $R^7$ is selected from —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

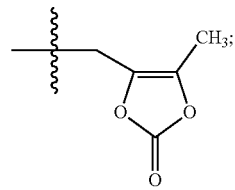 [SMILES: *Cc1oc(=O)oc1C]

or $R^2$ is H, $R^4$ is selected from —O-benzyl, —OCHR$^c$OC(O)—C$_{1-4}$alkyl, —OCH$_2$OC(O)CHR$^d$—NH$_2$, and —OCH$_2$OC(O)CHR$^d$—NHC(O)O—C$_{1-6}$alkyl, and $R^7$ is selected from H and —CH$_2$OC(O)CH$_3$; or $R^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, $R^4$ is —OH, and $R^7$ is H; where each $R^c$ is independently H or —C$_{1-3}$alkyl; each $R^d$ is independently H, —CH$_3$, —CH(CH$_3$)$_2$, phenyl, or benzyl; and each $R^e$ is independently H, —C$_{1-6}$alkyl, or phenyl; or a pharmaceutically acceptable salt thereof.

In one particular embodiment of the compounds of Formula I, $R^2$ is H, $R^4$ is —OH and $R^7$ is selected from —CH$_2$CF$_3$, —(CH$_2$)$_2$CF$_3$, —CH$_2$CF$_2$CH$_3$, —CH$_2$OC(O)CH$_3$, —CH$_2$OC(O)(CH$_2$)$_2$CH$_3$, —CH$_2$OC(O)CH[CH(CH$_3$)$_2$]NH$_2$, —CH$_2$OC(O)CH[CH(CH$_3$)$_2$]—NHC(O)OCH$_3$, benzyl, and

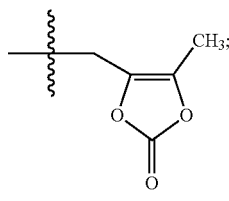 [SMILES: *Cc1oc(=O)oc1C]

or $R^2$ is H, $R^4$ is —OCH$_2$OC(O)CH$_3$ and $R^7$ is selected from H and —CH$_2$OC(O)CH$_3$; or $R^2$ is H, $R^4$ is selected from —OCH$_2$OC(O)(CH$_2$)$_2$CH$_3$, —CH$_2$OC(O)CH[CH(CH$_3$)$_2$]NH$_2$, and —OCH$_2$OC(O)CH[CH(CH$_3$)$_2$]—NHC(O)OCH$_3$, and $R^7$ is H; or $R^2$ is H, $R^4$ is —O-benzyl and $R^7$ is H.

The compound (2R,4R)-5-(3'-chlorobiphenyl-4-yl)-2-hydroxy-4-[(5-hydroxy-1-methyl-1H-pyrazole-3-carbonyl)amino]pentanoic acid is also specifically disclosed in U.S. Patent Publication No. 2012/0157383, and is represented by formula II':

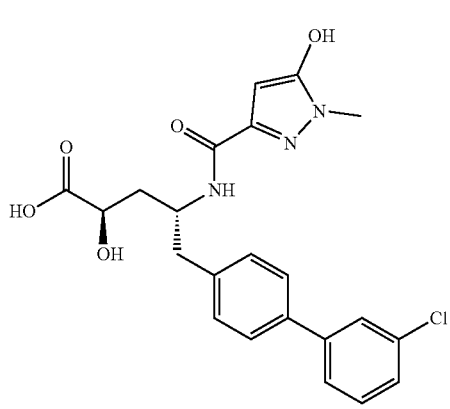

In one embodiment, this compound is referred to as the active form and is administered as a prodrug, which is metabolized in vivo to form the compound of formula II'. U.S. Patent Publication No. 2012/0157383 also disclosed the isobutyl ester prodrug of the compound of formula II'.

Another aspect of the invention relates to other prodrugs of the compound of formula II'. These prodrugs are represented by formula XII, where $R^a$ is H, $R^b$ is Cl, and X is:

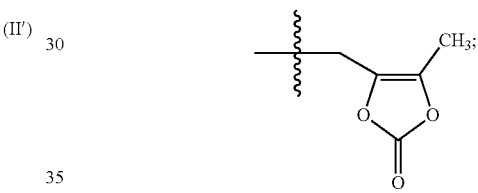

In one embodiment, these compounds are represented by formula II:

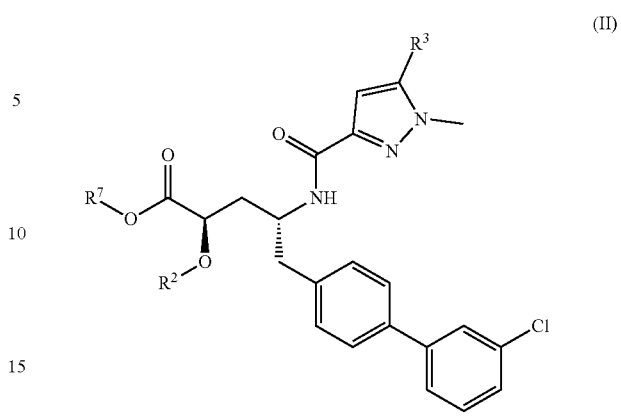

where $R^2$ is H, $R^3$ is —OH and $R^7$ is selected from —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$ alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

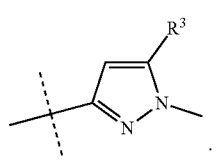

or $R^3$ is selected from —OC(O)CH$_2$CH$_3$, —OC(O)CH$_2$CH(CH$_3$)$_2$, —OC(O)-phenyl, —OCH$_2$OC(O)CHR$^d$—NH$_2$, and —OCH$_2$OC(O)CHR$^d$—NHC(O)O—C$_{1-6}$alkyl, and $R^7$ is H; or $R^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, $R^3$ is —OH, and $R^7$ is H; where each $R^c$ is independently H or —C$_{1-3}$alkyl; each $R^d$ is independently H, —CH$_3$, —CH(CH$_3$)$_2$, phenyl, or benzyl; and each $R^e$ is independently H, —C$_{1-6}$alkyl, or phenyl; or a pharmaceutically acceptable salt thereof.

In one particular embodiment of the compounds of Formula II, $R^2$ is H, $R^3$ is —OH and $R^7$ is selected from —CH$_2$CH$_3$, —CH$_2$CF$_2$CF$_3$, —CH(CH$_2$CH$_3$)CF$_3$, —CH(CH$_3$)CF$_2$CF$_3$, —CH$_2$OC(O)(CH$_2$)$_2$CH$_3$, —CH$_2$OC(O)CH[CH(CH$_3$)$_2$]NH$_2$, benzyl, and

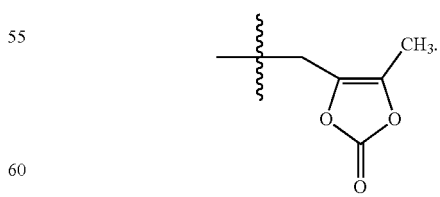

The compound (2R,4R)-5-(3'-chlorobiphenyl-4-yl)-2-hydroxy-4-[(5-hydroxy-1-pyridin-2-yl-1H-pyrazole-3-carbonyl)amino]pentanoic acid is also specifically disclosed in U.S. Patent Publication No. 2012/0157383, and is represented by formula III':

(III')

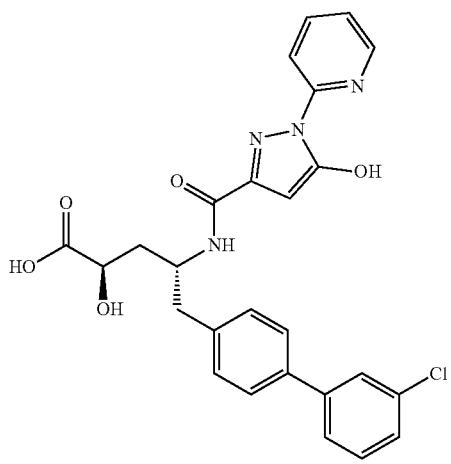

In one embodiment, this compound is referred to as the active form and is administered as a prodrug, which is metabolized in vivo to form the compound of formula III'.

Another aspect of the invention relates to other prodrugs of the compound of formula III'. These prodrugs are represented by formula XII, where $R^a$ is H, $R^b$ is Cl, and X is:

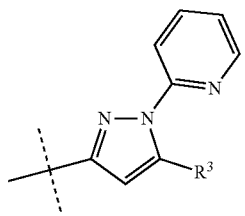

In one embodiment, these compounds are represented by formula III:

(III)

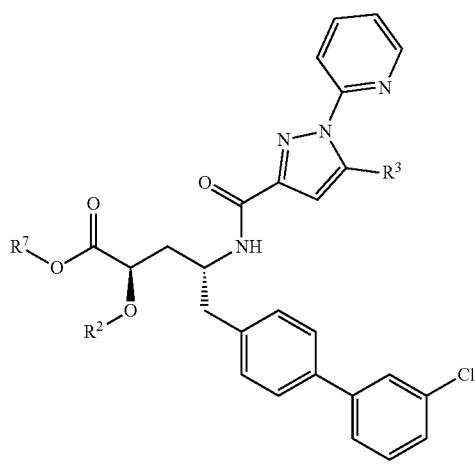

where $R^2$ is H, $R^3$ is —OH and $R^7$ is selected from —CH$_2$CH$_3$, —CH$_2$CH(CH$_3$)$_2$, —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

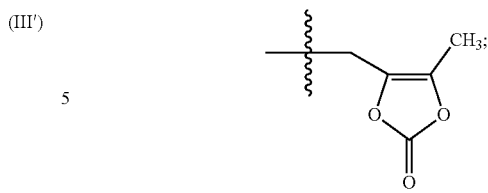

or $R^2$ is H, $R^3$ is selected from —OC(O)CH$_2$CH$_3$, —OC(O)CH$_2$CH(CH$_3$)$_2$, —OC(O)-phenyl, —OCH$_2$OC(O)CHR$^d$—NH$_2$, and —OCH$_2$OC(O)CHR$^d$—NHC(O)O—C$_{1-6}$alkyl, and $R^7$ is H; or $R^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, $R^3$ is —OH, and $R^7$ is H; where each $R^c$ is independently H or —C$_{1-3}$alkyl; each $R^d$ is independently H, —CH$_3$, —CH(CH$_3$)$_2$, phenyl, or benzyl; and each $R^e$ is independently H, —C$_{1-6}$alkyl, or phenyl; or a pharmaceutically acceptable salt thereof.

In one particular embodiment of the compounds of Formula III, $R^2$ is H, $R^3$ is —OH and $R^7$ is selected from —CH$_2$CH$_3$, —CH$_2$CH(CH$_3$)$_2$, —CH$_2$OC(O)CHR$^d$—NHC(O)O—C$_{1-6}$alkyl, benzyl, and

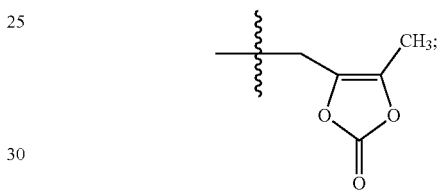

where $R^d$ is —CH(CH$_3$)$_2$. In another embodiment of the compounds of Formula III, $R^2$ is H, $R^3$ is —OCH$_2$OC(O)CH[CH(CH$_3$)$_2$]NH$_2$, and $R^7$ is H. In still another embodiment of the compounds of Formula III, $R^2$ is —C(O)CH[CH(CH$_3$)$_2$]NH$_2$, $R^3$ is —OH, and $R^7$ is H.

Another aspect of the invention relates to a compound of formula XII, where $R^a$ is F, $R^b$ is Cl, and X is:

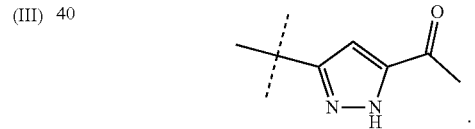

In one embodiment, these compounds are represented by formula IV:

(IV)

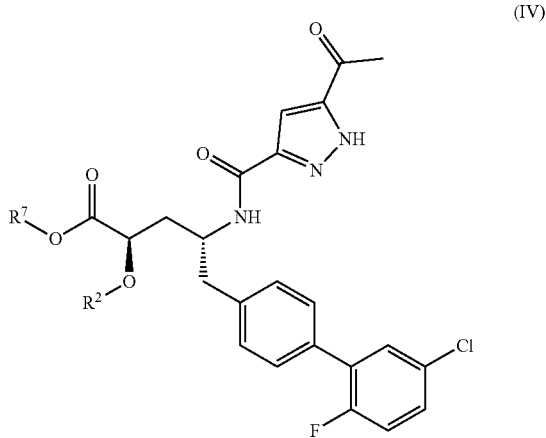

where R² is H and R⁷ is selected from H, —CH₂CH₃, —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C₁₋₄alkyl, —CHR$^c$OC(O)O—C₂₋₄alkyl, —CHR$^c$OC(O)O-cyclohexyl, —C₂₋₄alkylene-N(CH₃)₂, —CH₂OC(O)CHR$^d$—NH₂, —CH₂OC(O)CHR$^d$—NHC(O)O—C₁₋₆alkyl, benzyl, and

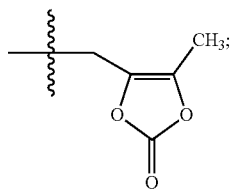 [SMILES: *Cc1oc(=O)oc1C]

or R² is selected from —C(O)—C₁₋₆alkyl, —C(O)CHR$^d$—NH₂, —C(O)CHR$^d$—NHC(O)O—C₁₋₆alkyl, and —P(O)(OR$^e$)₂, and R⁷ is H; where each R$^c$ is independently H or —C₁₋₃alkyl; each R$^d$ is independently H, —CH₃, —CH(CH₃)₂, phenyl, or benzyl; and each R$^e$ is independently H, —C₁₋₆alkyl, or phenyl; or a pharmaceutically acceptable salt thereof.

In one particular embodiment of the compounds of Formula IV, R² is H and R⁷ is selected from H and —CH₂CH₃.

Another aspect of the invention relates to a compound of formula XII, where R$^a$ is H, R$^b$ is Cl, and X is:

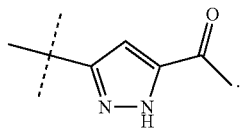

In one embodiment, these compounds are represented by formula V:

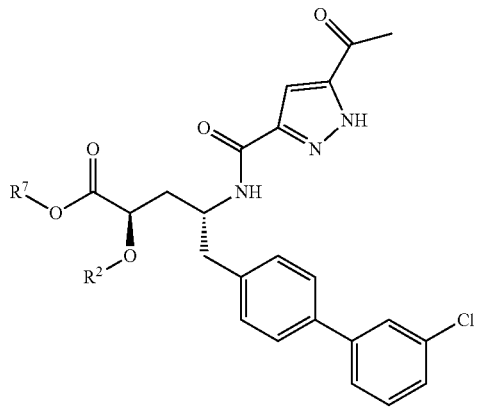

(V)

where R² is H and R⁷ is selected from H, —CH₂CH₃, —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C₁₋₄alkyl, —CHR$^c$OC(O)O—C₂₋₄alkyl, —CHR$^c$OC(O)O-cyclohexyl, —C₂₋₄alkylene-N(CH₃)₂, —CH₂OC(O)CHR$^d$—NH₂, —CH₂OC(O)CHR$^d$—NHC(O)O—C₁₋₆alkyl, benzyl, and

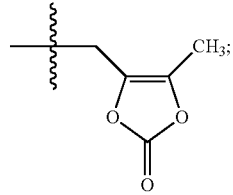 [SMILES: *Cc1oc(=O)oc1C]

or R² is selected from —C(O)—C₁₋₆alkyl, —C(O)CHR$^d$—NH₂, —C(O)CHR$^d$—NHC(O)O—C₁₋₆alkyl, and —P(O)(OR$^e$)₂, and R⁷ is H; where each R$^c$ is independently H or —C₁₋₃alkyl; each R$^d$ is independently H, —CH₃, —CH(CH₃)₂, phenyl, or benzyl; and each R$^e$ is independently H, —C₁₋₆alkyl, or phenyl; or a pharmaceutically acceptable salt thereof.

In one particular embodiment of the compounds of Formula V, R² is H and R⁷ is selected from H and —CH₂CH₃.

Another aspect of the invention relates to a compound of formula XII, where R$^a$ is H, R$^b$ is Cl, and X is:

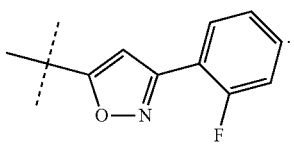

In one embodiment, these compounds are represented by formula VI:

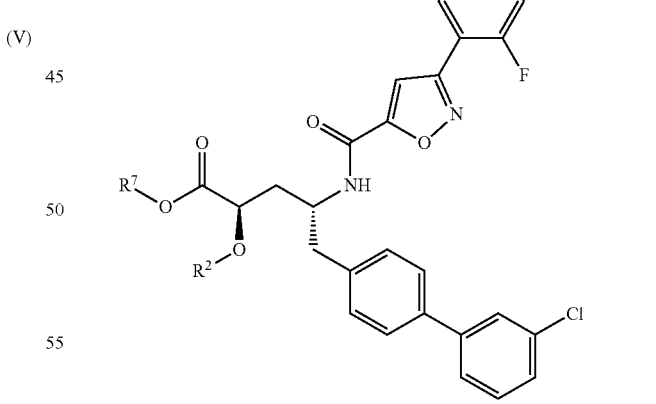

(VI)

where R² is H and R⁷ is selected from H, —CH₂CH₃, —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR$^c$OC(O)—C₁₋₄alkyl, —CHR$^c$OC(O)O—C₂₋₄alkyl, —CHR$^c$OC(O)O-cyclohexyl, —C₂₋₄alkylene-N(CH₃)₂, —CH₂OC(O)CHR$^d$—NH₂, —CH₂OC(O)CHR$^d$—NHC(O)O—C₁₋₆alkyl, benzyl, and

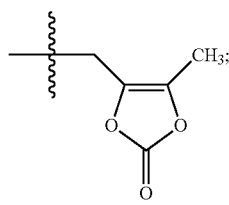 [SMILES: *Cc1oc(=O)oc1C]

or R² is selected from —C(O)—C₁₋₆alkyl, —C(O)CHR^d—NH₂, —C(O)CHR^d—NHC(O)O—C₁₋₆alkyl, and —P(O)(OR^e)₂, and R⁷ is H; where each R^c is independently H or —C₁₋₃alkyl; each R^d is independently H, —CH₃, —CH(CH₃)₂, phenyl, or benzyl; and each R^e is independently H, —C₁₋₆alkyl, or phenyl; or a pharmaceutically acceptable salt thereof.

In one particular embodiment of the compounds of Formula VI, R² is H and R⁷ is selected from H, —CH₂OC(O)CH₃, —CH₂OC(O)OCH₂CH₃, —CH₂OC(O)OCH(CH₃)₂, and —C(O)CH[CH(CH₃)₂]—NHC(O)OCH₃.

The compound (2R,4R)-5-(3'-chlorobiphenyl-4-yl)-2-hydroxy-4-[(3-methoxy-isoxazole-5-carbonyl)amino]pentanoic acid is also specifically disclosed in U.S. Patent Publication No. 2012/0157383, and is represented by formula VII':

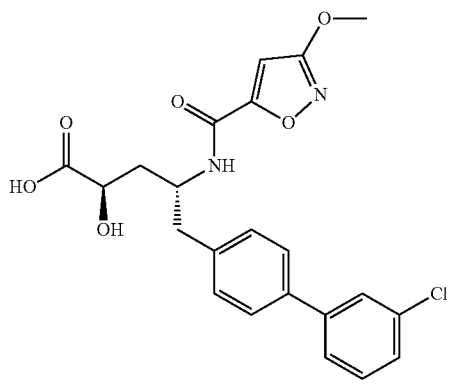

(VII')

In one embodiment, this compound is referred to as the active form and is administered as a prodrug, which is metabolized in vivo to form the compound of formula VII'.

Another aspect of the invention relates to other prodrugs of the compound of formula VII'. These prodrugs are represented by formula XII, where R^a is H, R^b is Cl, and X is:

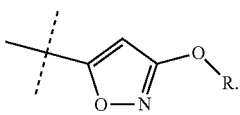

where R is H or —CH₃. In one embodiment, these compounds are represented by formula VII:

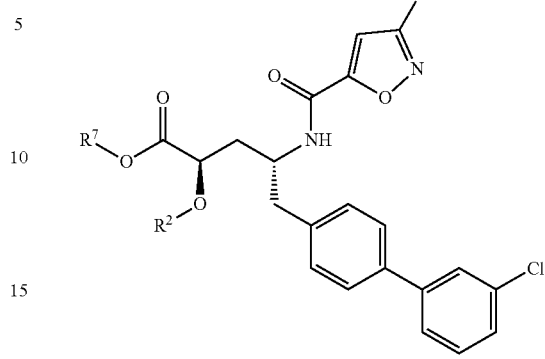

(VII)

where R² is H and R⁷ is selected from —CH₂CH₃, —CH₂CF₃, —(CH₂)₂CF₃, —CH₂CF₂CH₃, —CH₂CF₂CF₃, —C(CH₃)(CF₃)₂, —CH(CH₂CH₃)CF₃, —CH(CH₃)CF₂CF₃, —(CH₂)₂₋₃OH, —CH₂CH(NH₂)COOCH₃, —(CH₂)₂OCH₃, —CHR^cOC(O)—C₁₋₄alkyl, —CHR^cOC(O)O—C₂₋₄alkyl, —CHR^cOC(O)O-cyclohexyl, —C₂₋₄alkylene-N(CH₃)₂, —CH₂OC(O)CHR^d—NH₂, —CH₂OC(O)CHR^d—NHC(O)O—C₁₋₆alkyl, benzyl, and

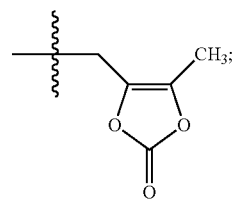 [SMILES: *Cc1oc(=O)oc1C]

or R² is selected from —C(O)—C₁₋₆alkyl, —C(O)CHR^d—NH₂, —C(O)CHR^d—NHC(O)O—C₁₋₆alkyl, and —P(O)(OR^e)₂, and R⁷ is H; where each R^c is independently H or —C₁₋₃alkyl; each R^d is independently H, —CH₃, —CH(CH₃)₂, phenyl, or benzyl; and each R^e is independently H, —C₁₋₆alkyl, or phenyl; or a pharmaceutically acceptable salt thereof.

In one particular embodiment of the compounds of Formula VII, R is —CH₃, R² is H, and R⁷ is selected from —CH₂OC(O)CH₃, —CH₂OC(O)OCH(CH₃)₂, —CH₂OC(O)OCH₂CH₃, and —CH₂OC(O)CH[CH(CH₃)₂]—NHC(O)OCH₃.

The compound (2R,4R)-5-(5'-chloro-2'-fluorobiphenyl-4-yl)-2-hydroxy-4-[(1-hydroxy-1H-[1,2,3]triazole-4-carbonyl)amino]pentanoic acid is also specifically disclosed in U.S. Patent Publication No. 2012/0157383, and is represented by formula VIII':

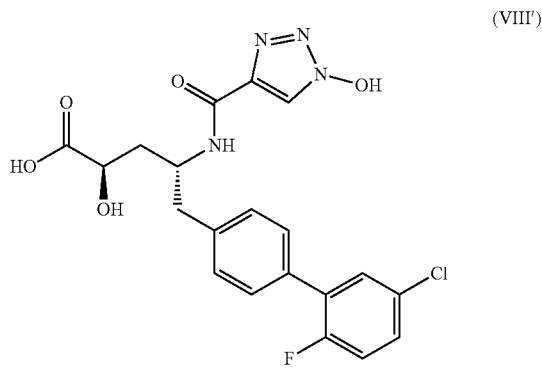 [SMILES: O=C(N[C@H](Cc1ccc(-c2cc(Cl)ccc2F)cc1)C[C@@H](O)C(=O)O)c1cn(O)nn1]

(VIII')

In one embodiment, this compound is referred to as the active form and is administered as a prodrug, which is metabolized in vivo to form the compound of formula VIII'. U.S. Patent Publication No. 2012/0157383 also disclosed the isopropyl ester, ethyl ester, isobutyl ester, and heptyl ester prodrugs of the compound of formula VIII'.

Another aspect of the invention relates to other prodrugs of the compound of formula VIII'. These prodrugs are represented by formula XII, where $R^a$ is F, $R^b$ is Cl, and X is:

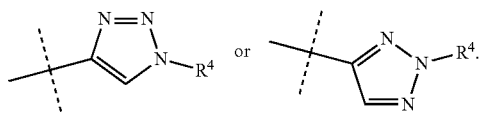

In one embodiment, these compounds are represented by formula VIIIa or VIIIb:

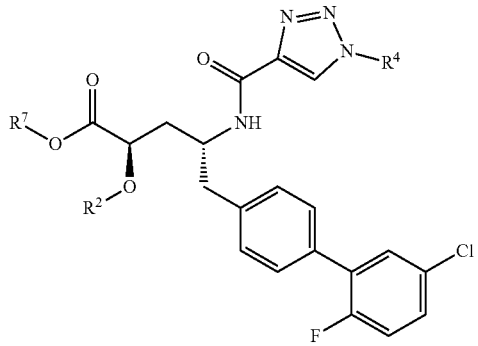
(VIIIa)

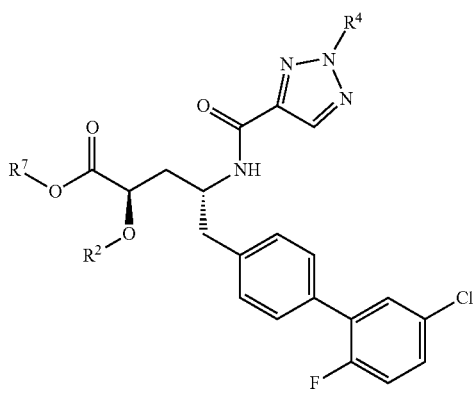
(VIIIb)

where $R^2$ is H, $R^4$ is —OH, and $R^7$ is selected from —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$ alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

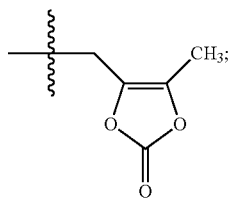 [SMILES: *Cc1oc(=O)oc1C]

or $R^2$ is H, $R^4$ is selected from —O-benzyl, —OCHR$^c$OC(O)—C$_{1-4}$alkyl, —OCH$_2$OC(O)CH[CH(CH$_3$)$_2$]NH$_2$, —OCH$_2$OC(O)CH[CH(CH$_3$)$_2$]—NHC(O)OCH$_3$ and

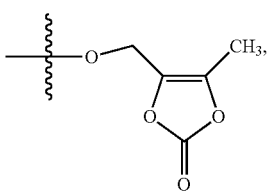 [SMILES: *OCc1oc(=O)oc1C]

and $R^7$ is H; or $R^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, $R^4$ is —OH, and $R^7$ is H; where each $R^c$ is independently H or —C$_{1-3}$alkyl; each $R^d$ is independently H, —CH$_3$, —CH(CH$_3$)$_2$, phenyl, or benzyl; and each $R^e$ is independently H, —C$_{1-6}$alkyl, or phenyl; or a pharmaceutically acceptable salt thereof.

In one particular embodiment of the compounds of Formula VIIIa and VIIIb, $R^2$ is H, $R^4$ is —OH and $R^7$ is selected from —CH$_2$CF$_2$CF$_3$, —CH$_2$OC(O)CH$_3$, —CH$_2$OC(O)(CH$_2$)$_2$CH$_3$, —CH$_2$OC(O)OCH$_2$CH$_3$, —CH$_2$OC(O)OCH(CH$_3$)$_2$, —CH(CH$_3$)OC(O)O-cyclohexyl, —CH$_2$OC(O)CH[CH(CH$_3$)$_2$]—NHC(O)OCH$_3$, and

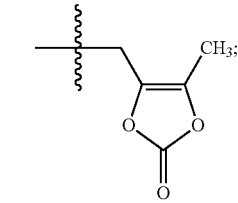 [SMILES: *Cc1oc(=O)oc1C]

or $R^2$ is H, $R^4$ is selected from —OCH$_2$OC(O)(CH$_2$)$_2$CH$_3$, —OCH$_2$OC(O)CH[CH(CH$_3$)$_2$]NH$_2$, —OCH$_2$OC(O)CH[CH(CH$_3$)$_2$]—NHC(O)OCH$_3$, and

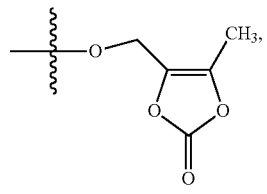 [SMILES: *OCc1oc(=O)oc1C]

and $R^7$ is H.

The compound (2R,4R)-5-(3'-chlorobiphenyl-4-yl)-2-hydroxy-4-[(5-oxo-1-phenyl-4,5-dihydro-1H-[1,2,4]triazole-3-carbonyl)amino]pentanoic acid is also specifically disclosed in U.S. Patent Publication No. 2012/0157383, and is represented by formula IX':

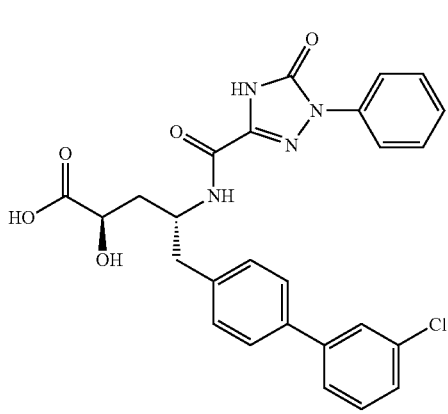

(IX')

In one embodiment, this compound is referred to as the active form and is administered as a prodrug, which is metabolized in vivo to form the compound of formula IX'.

Another aspect of the invention relates to other prodrugs of the compound of formula IX'. These prodrugs are represented by formula XII, where $R^a$ is H, $R^b$ is Cl, and X is:

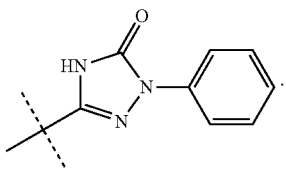

In one embodiment, these compounds are represented by formula IX:

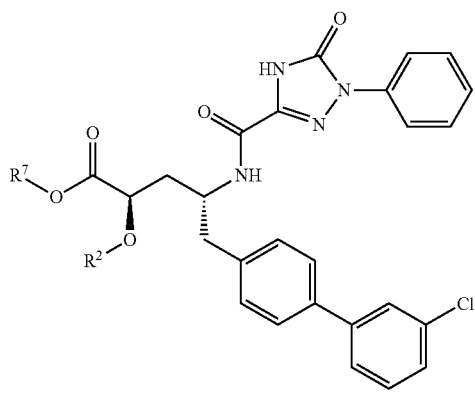

(IX)

where $R^2$ is H and $R^7$ is selected from —CH$_2$CH$_3$, —CH$_2$CF$_3$, —(CH$_2$)$_2$CF$_3$, —CH$_2$CF$_2$CH$_3$, —CH$_2$CF$_2$CF$_3$, —C(CH$_3$)(CF$_3$)$_2$, —CH(CH$_2$CH$_3$)CF$_3$, —CH(CH$_3$)CF$_2$CF$_3$, —(CH$_2$)$_{2-3}$OH, —CH$_2$CH(NH$_2$)COOCH$_3$, —(CH$_2$)$_2$OCH$_3$, —CHR$^c$OC(O)—C$_{1-4}$alkyl, —CHR$^c$OC(O)O—C$_{2-4}$alkyl, —CHR$^c$OC(O)O-cyclohexyl, —C$_{2-4}$ alkylene-N(CH$_3$)$_2$, —CH$_2$OC(O)CHR$^d$—NH$_2$, —CH$_2$OC(O)CHR$^d$—NHC(O)O—C$_{1-6}$alkyl, benzyl, and

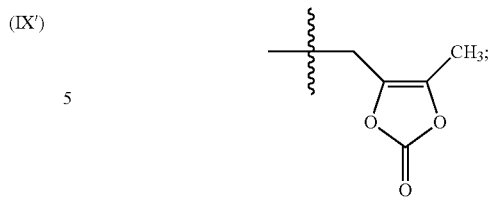

or $R^2$ is selected from —C(O)—C$_{1-6}$alkyl, —C(O)CHR$^d$—NH$_2$, —C(O)CHR$^d$—NHC(O)O—C$_{1-6}$alkyl, and —P(O)(OR$^e$)$_2$, and $R^7$ is H; where each $R^c$ is independently H or —C$_{1-3}$alkyl; each $R^d$ is independently H, —CH$_3$, —CH(CH$_3$)$_2$, phenyl, or benzyl; and each $R^e$ is independently H, —C$_{1-6}$alkyl, or phenyl; or a pharmaceutically acceptable salt thereof.

In one particular embodiment of the compounds of Formula IX, $R^2$ is H and $R^7$ is selected from —CH$_2$OC(O)OCH$_2$CH$_3$ and —CH$_2$OC(O)CH[CH(CH$_3$)$_2$]—NHC(O)OCH$_3$.

The compound (2R,4R)-4-[(5-acetyl-2H-pyrazole-3-carbonyl)amino]-5-biphenyl-4-yl-2-hydroxypentanoic acid is also specifically disclosed in U.S. Patent Publication No. 2012/0157383, and is represented by formula X':

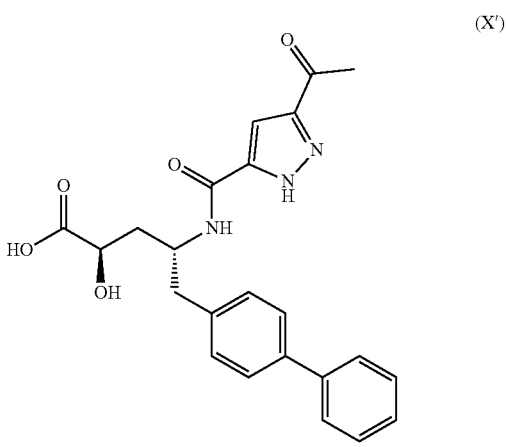 [SMILES: CC(=O)c1cc(C(=O)N[C@H](Cc2ccc(-c3ccccc3)cc2)C[C@@H](O)C(=O)O)[nH]n1]

(X')

In one embodiment, this compound is referred to as the active form and is administered as a prodrug, which is metabolized in vivo to form the compound of formula X'. U.S. Patent Publication No. 2012/0157383 also disclosed the ethyl ester, butyl ester, methoxyethyl ester, medoxomil ester, mofetil ester, and methanesulfonylethyl ester prodrugs of the compound of formula X'.

Another aspect of the invention relates to other prodrugs of the compound of formula X'. These prodrugs are represented by formula XII, where $R^a$ is H, $R^b$ is H, and X is:

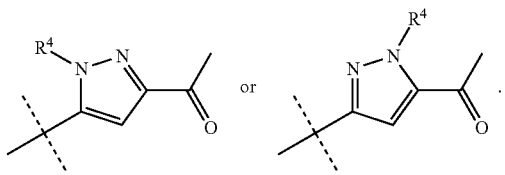

In one embodiment, these compounds are represented by formula Xa or Xb:

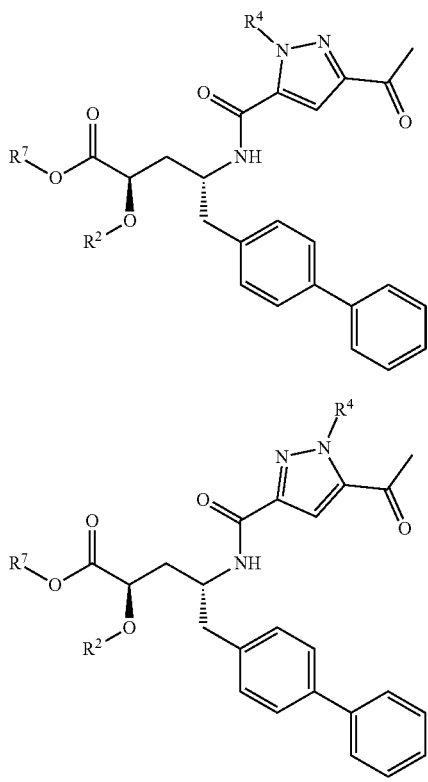

(Xa)

(Xb)

where $R^2$ and $R^4$ are H, and $R^7$ is selected from —$CH_2CF_3$, —$(CH_2)_2CF_3$, —$CH_2CF_2CH_3$, —$CH_2CF_2CF_3$, —$C(CH_3)(CF_3)_2$, —$CH(CH_2CH_3)CF_3$, —$CH(CH_3)CF_2CF_3$, —$(CH_2)_{2-3}OH$, —$CH_2CH(NH_2)COOCH_3$, —$CHR^cOC(O)$—$C_{1-4}alkyl$, —$CHR^cOC(O)O$—$C_{2-4}alkyl$, —$CHR^cOC(O)O$-cyclohexyl, —$C_{2-4}alkylene$-$N(CH_3)_2$, —$CH_2OC(O)CHR^d$—$NH_2$, —$CH_2OC(O)CHR^d$—$NHC(O)O$—$C_{1-6}alkyl$, and benzyl; or $R^2$ is H, $R^4$ is selected from —$CH_2OC(O)CH[CH(CH_3)_2]$—$NHC(O)OCH_3$ and —$CH_2OC(O)CH[CH(CH_3)_2]NH_2$, and $R^7$ is H; or $R^2$ is selected from —$C(O)$—$C_{1-6}alkyl$, —$C(O)CHR^d$—$NH_2$, —$C(O)CHR^d$—$NHC(O)O$—$C_{1-6}alkyl$, and —$P(O)(OR^e)_2$, $R^4$ is H, and $R^7$ is H; or $R^2$ is H, $R^4$ is —$CH_2OP(O)(OR^e)_2$ or —$CH_2OC(O)CH[CH(CH_3)_2]NH_2$, and $R^7$ is —$CH_2CH_3$; or $R^2$ is —$C(O)CH[CH(CH_3)_2]NH_2$, $R^4$ is H, and $R^7$ is —$CH_2CH_3$; and where each $R^c$ is independently H or —$C_{1-3}alkyl$; each $R^d$ is independently H, —$CH_3$, —$CH(CH_3)_2$, phenyl, or benzyl; and each $R^e$ is independently H, —$C_{1-6}alkyl$, or phenyl; or a pharmaceutically acceptable salt thereof.

In one particular embodiment of the compounds of Formula Xa and Xb, $R^2$ is H, $R^4$ is —$CH_2$—$OP(O)(OH)_2$ or —$CH_2OC(O)CH[CH(CH_3)_2]NH_2$, and $R^7$ is —$CH_2CH_3$. In another embodiment of the compounds of Formula Xa and Xb, $R^2$ is —$C(O)CH[CH(CH_3)_2]NH_2$, $R^4$ is H, and $R^7$ is —$CH_2CH_3$.

Another aspect of the invention relates to a compound of formula XII, where $R^a$ is H, $R^b$ is Cl, and X is:

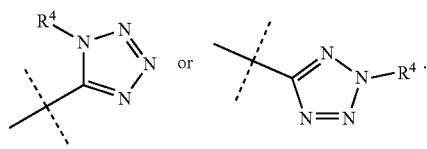

In one embodiment, these compounds are represented by formula XIa or XIb:

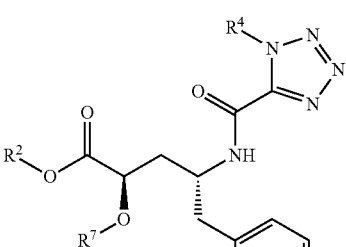

(XIa)

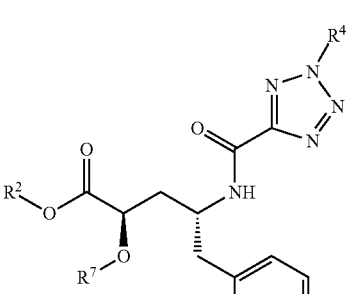

(XIb)

where $R^2$ and $R^4$ are H, and $R^7$ is selected from H, —$CH_2CH_3$, —$CH_2CF_3$, —$(CH_2)_2CF_3$, —$CH_2CF_2CH_3$, —$CH_2CF_2CF_3$, —$C(CH_3)(CF_3)_2$, —$CH(CH_2CH_3)CF_3$, —$CH(CH_3)CF_2CF_3$, —$(CH_2)_{2-3}OH$, —$CH_2CH(NH_2)COOCH_3$, —$(CH_2)_2OCH_3$, —$CHR^cOC(O)$—$C_{1-4}alkyl$, —$CHR^cOC(O)O$—$C_{2-4}alkyl$, —$CHR^cOC(O)O$-cyclohexyl, —$C_{2-4}alkylene$-$N(CH_3)_2$, —$CH_2OC(O)CHR^d$—$NH_2$, —$CH_2OC(O)CHR^d$—$NHC(O)O$—$C_{1-6}alkyl$, and benzyl; or $R^2$ is H, $R^4$ is selected from —$CH_2OC(O)CH[CH(CH_3)_2]$—$NHC(O)OCH_3$ and —$CH_2OC(O)CH[CH(CH_3)_2]NH_2$, and $R^7$ is H; or $R^2$ is selected from —$C(O)$—$C_{1-6}alkyl$, —$C(O)CHR^d$—$NH_2$, —$C(O)CHR^d$—$NHC(O)O$—$C_{1-6}alkyl$, and —$P(O)(OR^e)_2$, $R^4$ is H, and $R^7$ is H; or $R^2$ is H, $R^4$ is —$CH_2OP(O)(OR^e)_2$ or —$CH_2OC(O)CH[CH(CH_3)_2]NH_2$, and $R^7$ is —$CH_2CH_3$; or $R^2$ is —$C(O)CH[CH(CH_3)_2]NH_2$, $R^4$ is H, and $R^7$ is —$CH_2CH_3$; and where each $R^c$ is independently H or —$C_{1-3}alkyl$; each $R^d$ is independently H, —$CH_3$, —$CH(CH_3)_2$, phenyl, or benzyl; and each $R^e$ is independently H, —$C_{1-6}alkyl$, or phenyl; or a pharmaceutically acceptable salt thereof.

In one particular embodiment of the compounds of Formula XIa and XIb, $R^2$, $R^4$, and $R^7$ are H. In another embodiment of the compounds of Formula XIa and XIb, $R^2$ and $R^4$ are H, and $R^7$ is —$CH_2OC(O)OCH_2CH_3$.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. In some instances, reactions were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Fourth Edition, Wiley, New York, 2006, and references cited therein.

Carboxy-protecting groups are suitable for preventing undesired reactions at a carboxy group, and examples include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Amino-protecting groups are suitable for preventing undesired reactions at an amino group, and examples include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like.

Standard deprotection techniques and reagents are used to remove the protecting groups, and may vary depending upon which group is used. For example, sodium or lithium hydroxide is commonly used when the carboxy-protecting group is methyl, an acid such as TFA or HCl (e.g., 4.0 M HCl in 1,4-dioxane) is commonly used when the carboxy-protecting group is ethyl or t-butyl, and $H_2$/Pd/C may be used when the carboxy-protecting group is benzyl. A BOC amino-protecting group can be removed using an acidic reagent such as TFA in DCM or HCl in 1,4-dioxane, while a Cbz amino-protecting group can be removed by employing catalytic hydrogenation conditions such as $H_2$ (1 atm) and 10% Pd/C in an alcoholic solvent ("$H_2$/Pd/C").

Leaving groups are functional groups or atoms that can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

Suitable bases for use in these schemes include, by way of illustration and not limitation, potassium carbonate, calcium carbonate, sodium carbonate, triethylamine ($Et_3N$), pyridine, 1,8-diazabicyclo-[5.4.0]undec-7-ene (DBU), N,N-diisopropylethylamine (DIPEA), 4-methylmorpholine, sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), N,N-dimethylacetamide (DMA), dimethyl sulfoxide (DMSO), toluene, dichloromethane (DCM), chloroform ($CHCl_3$), carbon tetrachloride ($CCl_4$), 1,4-dioxane, methanol, ethanol, water, diethyl ether, acetone, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), 1,3-dicyclohexylcarbodiimide (DCC), N-(3-dimethylaminopropyl)-N'-ethylcarbodiimide (EDC), carbonyldiimidazole (CDI), 1-hydroxybenzotriazole (HOBt), and the like. Coupling reactions are conducted in an inert diluent in the presence of a base such as DIPEA, and are performed under conventional amide bond-forming conditions.

All reactions are typically conducted at a temperature within the range of about −78 C to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, chloroform); washing (for example, with saturated aqueous NaCl, saturated aqueous $NaHCO_3$, $Na_2CO_3$ (5%), $CHCl_3$ or 1M NaOH); drying (for example, over $MgSO_4$, over $Na_2SO_4$, or in vacuo); filtering; crystallizing (for example, from EtOAc and hexanes); being concentrated (for example, in vacuo); and/or purification (e.g., silica gel chromatography, flash chromatography, preparative HPLC, reverse phase-HPLC, or crystallization).

By way of illustration, compounds of the invention, as well as their salts, can be prepared as shown in Schemes I-IV.

Scheme I

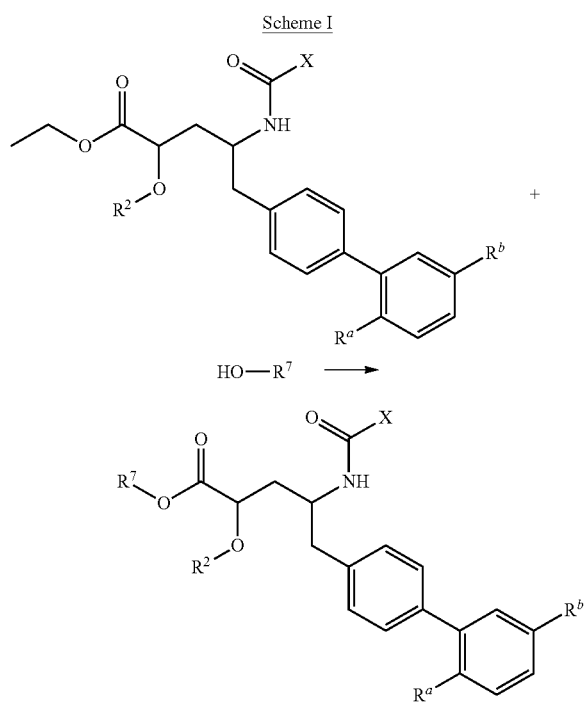

Scheme I is a transesterification reaction. Generally, this reaction involves reacting the ester with heat, the desired alcohol (HO—$R^7$) and a suitable acid catalyst, for example hydrochloric acid. The HO—$R^7$ alcohols are either commercially available or can be prepared by techniques that are known in the art or described herein. Exemplary HO—$R^7$ compounds include HO—$CH_2CF_3$, HO—$(CH_2)_2CF_3$, HO—$CH_2CF_2CH_3$, HO—$CH_2CF_2CF_3$, HO—$C(CH_3)(CF_3)_2$, HO—$CH(CH_2CH_3)CF_3$, HO—$CH(CH_3)CF_2CF_3$, benzyl alcohol, and

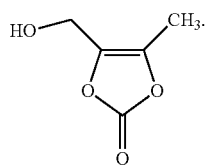

Scheme II

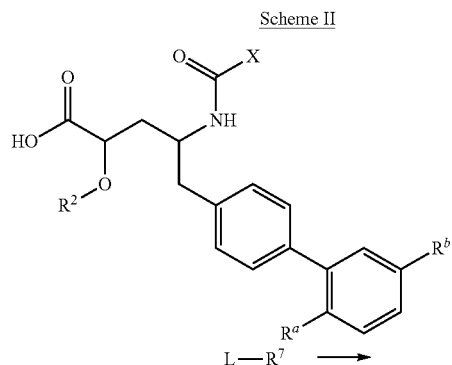

Scheme II is a nucleophilic substitution reaction, where L is a suitable leaving group. Generally, this reaction is conducted in the presence of a suitable base such as triethylamine in a suitable inert diluent or solvent such as acetone. The L-$R^7$ compounds are either commercially available or can be prepared by techniques that are known in the art or described herein. Exemplary L-$R^7$ compounds include Br—$(CH_2)_2OH$, Br—$(CH_2)_3OH$, Br—$(CH_2)_2OCH_3$, Br—$CH_2OC(O)CH_3$, Cl—$CH_2OC(O)(CH_2)_2CH_3$, Cl—$CH_2OC(O)OCH_2CH_3$, Cl—$CH_2OC(O)OCH(CH_3)_2$, Cl—$CH_2OC(O)O$-cyclohexyl, (S)-2-benzyloxycarbonylamino-3-methyl-butyric acid chloromethyl ester, and (S)-2-t-butoxycarbonylamino-3-methyl-butyric acid chloromethyl ester.

Alternately, in Scheme II, an alcohol have be used in place of the L-$R^7$, for example HO—$C_{2-4}$alkylene-$N(CH_3)_2$ in a coupling reaction using HOBt and EDC.

Scheme III

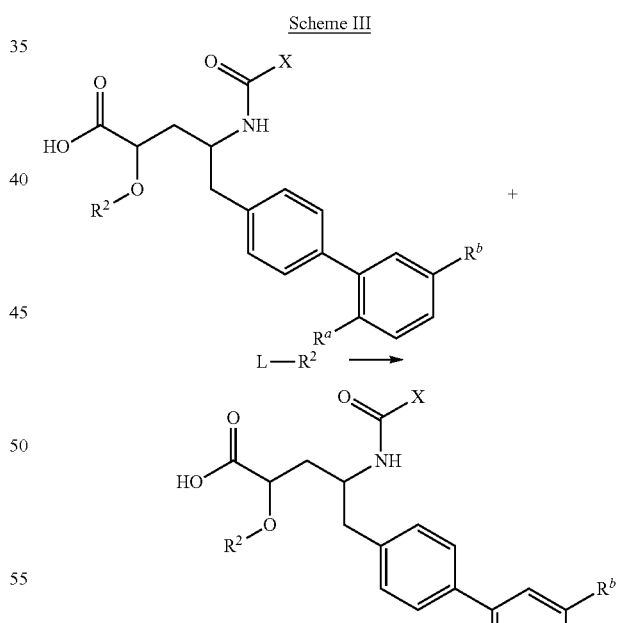

Scheme III is a nucleophilic substitution reaction, where L is a suitable leaving group. Generally, this reaction is conducted in the presence of a suitable base such as N,N-diisopropylethylamine in a suitable inert diluent or solvent such as dichloromethane. The L-$R^2$ compound is either commercially available or can be prepared by techniques that are known in the art or described herein. Exemplary L-R² compounds include Cl—C(O)—CH₃, Cl—C(O)—CH(CH₃)₂, and Cl—C(O)—CH₂CH(CH₃)₂.

Scheme IV

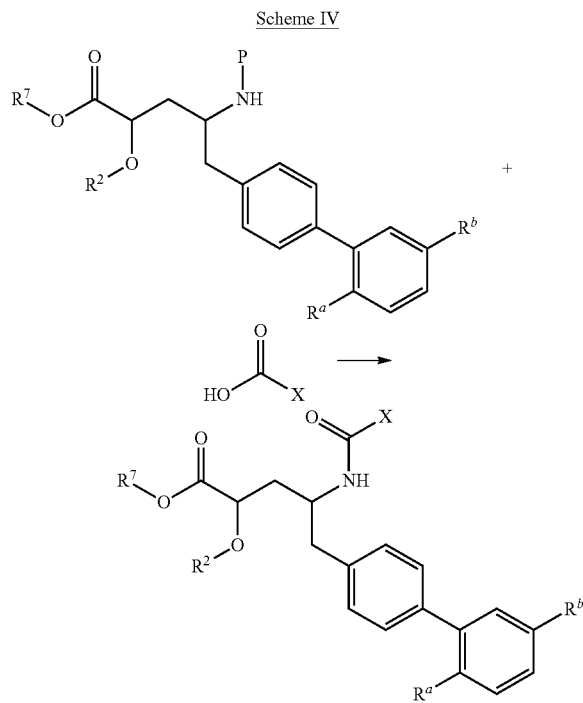

Scheme IV is a coupling reaction, where P is H or a suitable amino-protecting group. When P is an amino protecting group, the process further comprises deprotecting the compound before or in situ with the coupling step. Exemplary coupling reagents include HATU and HOBt with EDC. Generally, these reactions are conducted in the presence of a base such as DIPEA or 4-methylmorpholine, and an inert diluent or solvents such as DMF or DMA. The carboxylic acid starting materials are generally commercially available or can be prepared using procedures that are known in the art.

Further details regarding specific reaction conditions and other procedures for preparing representative compounds of the invention or intermediates thereof are described in the Examples set forth below.

Utility

The compounds of formula I'-III' and VII'-X' have activity as neprilysin inhibitors, and are expected to have therapeutic utility as neprilysin inhibitors. Prodrugs of these compounds, once metabolized in vivo, are expected to have the same utility. Thus, when discussing the activity of the compounds of the invention, it is understood that these prodrugs have the expected activity once metabolized.

Exemplary assays include by way of illustration and not limitation, assays that measure NEP inhibition. Useful secondary assays include assays to measure ACE inhibition and aminopeptidase P (APP) inhibition (e.g., as described in Sulpizio et al. (2005) JPET 315:1306-1313). A pharmacodynamic assay to assess the in vivo inhibitory potencies for ACE and NEP in anesthetized rats is described in Seymour et al. (1985) Hypertension 7(Suppl I):I-35-I-42 and Wigle et al. (1992) Can. J. Physiol. Pharmacol. 70:1525-1528), where ACE inhibition is measured as the percent inhibition of the angiotensin I pressor response and NEP inhibition is measured as increased urinary cyclic guanosine 3',5'-monophosphate (cGMP) output.

There are also many in vivo assays that can be used. The conscious spontaneously hypertensive rat (SHR) model is a renin dependent hypertension model. See for example, Intengan et al. (1999) Circulation 100(22):2267-2275 and Badyal et al. (2003) Indian Journal of Pharmacology 35:349-362. The conscious desoxycorticosterone acetate-salt (DOCA-salt) rat model is a volume dependent hypertension model that is useful for measuring NEP activity. See for example, Trapani et al. (1989) J. Cardiovasc. Pharmacol. 14:419-424, Intengan et al. (1999) Hypertension 34(4): 907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensive (DSS) hypertensive rat model is a model of hypertension that is sensitive to dietary salt (NaCl), and is described, for example, in Rapp (1982) Hypertension 4:753-763. The rat monocrotaline model of pulmonary arterial hypertension described, for example, in Kato et al. (2008) J. Cardiovasc. Pharmacol. 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) J. Amer. Soc. Nephrol. 7:1038-1044. Other animal models, such as the hot plate, tail-flick and formalin tests, can be used to measure the analgesic properties of a compound, as well as the spinal nerve ligation (SNL) model of neuropathic pain. See, for example, Malmberg et al. (1999) Current Protocols in Neuroscience 8.9.1-8.9.15. Other properties and utilities of the compounds can be demonstrated using various in vitro and in vivo assays well known to those skilled in the art.

The compounds of the invention are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a compound of the invention. For example, by inhibiting NEP, the compound is expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, the compounds are expected to have other physiological actions, for example, on the renal, central nervous, reproductive and gastrointestinal systems.

Cardiovascular Diseases

By potentiating the effects of vasoactive peptides like the natriuretic peptides and bradykinin, compounds of the invention are expected to find utility in treating and/or preventing medical conditions such as cardiovascular diseases. See, for example, Rogues et al. (1993) Pharmacol. Rev. 45:87-146 and Dempsey et al. (2009) Amer. J. of Pathology 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure, with or without accompanying renal disease. Thus, one embodiment of the invention relates to a method for treating hypertension, particularly primary hypertension or pulmonary arterial hypertension, comprising administering to a patient a therapeutically effective amount of a compound of the invention.

For treatment of primary hypertension, the therapeutically effective amount is typically the amount that is sufficient to lower the patient's blood pressure. This would include both mild-to-moderate hypertension and severe hypertension. When used to treat hypertension, the compound may be administered in combination with other therapeutic agents such as aldosterone antagonists, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting $\beta$-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a compound of the invention is combined with an $AT_1$ receptor antagonist, a diuretic, a calcium channel blocker, or a combination thereof, and used to treat primary hypertension. In another particular embodiment of the invention, a compound of the invention is combined with an $AT_1$ receptor antagonist, and used to treat hypertension with accompanying renal disease.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as $\alpha$-adrenergic antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, a compound of the invention is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of a compound of the invention. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting $\beta$-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a compound of the invention is combined with an aldosterone antagonist, a $\beta_1$-adrenergic receptor antagonist, an $AT_1$ receptor antagonist, or a diuretic, and used to treat congestive heart failure.

Diarrhea

As NEP inhibitors, compounds of the invention are expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marcais-Collado (1987) *Eur. J. Pharmacol.* 144(2): 125-132. When used to treat diarrhea, compounds of the invention may be combined with one or more additional antidiarrheal treatments.

Renal Diseases

By potentiating the effects of vasoactive peptides like the natriuretic peptides and bradykinin, compounds of the invention are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury or acute renal failure (see Sharkovska et al. (2011) *Clin. Lab.* 57:507-515 and Newaz et al. (2010) *Renal Failure* 32:384-390). When used to treat renal disease, the compound may be administered in combination with other therapeutic agents such as angiotensin-converting enzyme inhibitors, $AT_1$ receptor antagonists, and diuretics.

Preventative Therapy

By potentiating the effects of the natriuretic peptides, compounds of the invention are also expected to be useful in preventative therapy, due to the antihypertrophic and anti-fibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, compounds of the invention are expected to be useful to treat glaucoma. See, for example, Diestelhorst et al. (1989) *International Ophthalmology* 12:99-101. When used to treat glaucoma, compounds of the invention may be combined with one or more additional anti-glaucoma agents.

Pain Relief

As NEP inhibitors, compounds of the invention are expected to inhibit the degradation of endogenous enkephalins and thus such compounds may also find utility as analgesics. See, for example, Rogues et al. (1980) *Nature* 288:286-288 and Thanawala et al. (2008) *Current Drug Targets* 9:887-894. When used to treat pain, compounds of the invention may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-$HT_{1D}$ serotonin receptor agonists, and tricyclic antidepressants.

Other Utilities

Due to their NEP inhibition properties, compounds of the invention are also expected to be useful as antitussive agents, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE-V inhibitors, dopamine agonists, estrogen receptor agonists and/or antagonists, androgens, and estrogens. Due to their NEP inhibition properties, compounds of the invention are also expected to have anti-inflammatory properties, and are expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to their NEP inhibition properties, compounds of the invention are also expected to be useful in providing protection from nerve impairment caused by diabetes or diet induced obesity.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since the compounds of the invention are metabolized in vivo to compounds having activity as neprilysin inhibitors, they are also useful as a research tools for investigating or studying biological systems or samples having a NEP enzyme, for example to study diseases where the NEP enzyme or its peptide substrates plays a role. Accordingly, one aspect of the invention relates to a method of using a compound of the invention as a research tool, comprising conducting a biological assay using a compound of the invention. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a compound of the invention. These compounds can also be used as research tools by conducting biological assays using such compounds.

When used as a research tool, a biological system or sample comprising a NEP enzyme is typically contacted with a NEP enzyme-inhibiting amount of a compound of the invention. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the crystalline compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, the compounds of the invention can be used as research tools for evaluating other chemical compounds, and thus are also useful in screening assays to discover, for example, new compounds having NEP-inhibiting activity. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. In this manner, the compounds of the invention are used as standards in an assay to allow comparison of the results obtained with a test compound and with the compound of the invention to identify those test compounds that have about equal or superior activity, if any. For example, $pK_i$ data for a test compound or a group of test compounds is compared to the $pK_i$ data for a compound of the invention to identify those test compounds that have the desired properties, for example, test compounds having a $pK_i$ value about equal or superior to the compound of the invention, if any. This aspect of the invention includes, as separate embodiments, both the generation of comparison data (using the appropriate assays) and the analysis of test data to identify test compounds of interest.

Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more additional therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Such therapeutic agents are well known in the art, and include adenosine receptor antagonists, α-adrenergic receptor antagonists, $β_1$-adrenergic receptor antagonists, $β_2$-adrenergic receptor agonists, dual-acting β-adrenergic receptor antagonist/$α_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). It is also contemplated that the secondary agent may be administered more than 24 hours after administration of the compound of the invention. Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, compounds of the invention are administered in combination with an adenosine receptor antagonist, representative examples of which include, but are not limited to, naxifylline, rolofylline, SLV-320, theophylline, and tonapofylline.

In one embodiment, compounds of the invention are administered in combination with an α-adrenergic receptor antagonist, representative examples of which include, but are not limited to, doxazosin, prazosin, tamsulosin, and terazosin.

Compounds of the invention may also be administered in combination with a $\beta_1$-adrenergic receptor antagonist ("$\beta_1$-blockers"). Representative $\beta_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the $\beta_1$-blocker will be administered in an amount sufficient to provide from about 2-900 mg per dose.

In one embodiment, compounds of the invention are administered in combination with a $\beta_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like. Typically, the $\beta_2$-adrenergic receptor agonist will be administered in an amount sufficient to provide from about 0.05-500 µg per dose.

In one embodiment, compounds of the invention are administered in combination with an advanced glycation end product (AGE) breaker, examples of which include, by way of illustration and not limitation, alagebrium (or ALT-711), and TRC4149.

In another embodiment, compounds of the invention are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, compounds of the invention are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof.

In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day. In another embodiment, compounds of the invention are administered in combination with a dual-acting angiotensin-converting enzyme/neprilysin (ACE/NEP) inhibitor, examples of which include, but are not limited to: AVE-0848 ((4S,7S,2bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentyl-carbonyl]-L-tryptophan); fasidotril; fasidotrilate; enalaprilat; ER-32935 ((3R,6S,9aR)-6-[3 (S)-methyl-2(S)-sulfanylpentanamido]-5-oxoperhydrothiazolo[3,2-a] azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, compounds of the invention are administered in combination with an angiotensin-converting enzyme 2 (ACE2) activator or stimulator.

In one embodiment, compounds of the invention are administered in combination with an angiotensin-II vaccine, examples of which include, but are not limited to ATR12181 and CYT006-AngQb.

In one embodiment, compounds of the invention are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, compounds of the invention are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, compounds of the invention are administered in combination with antidiarrheal treatments. Representative treatment options include, but are not limited to, oral rehydration solutions (ORS), loperamide, diphenoxylate, and bismuth subsalicylate.

In yet another embodiment, a compound of the invention is administered in combination with an anti-glaucoma agent. Representative anti-glaucoma agents include, but are not limited to: α-adrenergic agonists such as brimonidine; $β_1$-adrenergic receptor antagonists; topical $β_1$-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, compounds of the invention are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, compounds of the invention are administered in combination with an anti-thrombotic agent. Representative anti-thrombotic agents include, but are not limited to: aspirin; anti-platelet agents such as clopidogrel, prasugrel, and ticlopidine; heparin, and combinations thereof.

In one embodiment, compounds of the invention are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compounds of the invention may also be administered in combination with a dual-acting agent, such as an $AT_1$ receptor antagonist/neprilysin inhibitor (ARB/NEP), examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-R(S)-2-mercapto-4-methylpentanoylamino)-methyl]imidazol-1-ylmethyl}-3'-fluorobiphenyl-2-carboxylic acid.

Compounds of the invention may also be administered in combination with multifunctional angiotensin receptor blockers as described in Kurtz & Klein (2009) *Hypertension Research* 32:826-834.

In one embodiment, compounds of the invention are administered in combination with a bradykinin receptor antagonist, for example, icatibant (HOE-140). It is expected that this combination therapy may present the advantage of preventing angioedema or other unwanted consequences of elevated bradykinin levels.

In one embodiment, compounds of the invention are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with an endothelin converting enzyme (ECE) inhibitor, examples of which include, but are not limited to, phosphoramidon, CGS 26303, and combinations thereof.

In a particular embodiment, compounds of the invention are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, a compound of the invention is administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, compounds of the invention are administered in combination with a monoamine reuptake inhibitor, examples of which include, by way of illustration and not limitation, norepinephrine reuptake inhibitors such as atomoxetine, buproprion and the buproprion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, compounds of the invention are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, compounds of the invention are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, compounds of the invention are administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, compounds of the invention are administered in combination with a neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, compounds of the invention are administered in combination with a nitric oxide donor, examples of which include, but are not limited to nicorandil; organic nitrates such as pentaerythritol tetranitrate; and sydnonimines such as linsidomine and molsidomine.

In yet another embodiment, compounds of the invention are administered in combination with a non-steroidal anti-inflammatory agent (NSAID). Representative NSAIDs include, but are not limited to: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, compounds of the invention are administered in combination with an N-methyl d-aspartate (NMDA) receptor antagonist, examples of which include, by way of illustration and not limitation, including amantadine, dextromethorphan, dextropropoxyphene, ketamine, ketobemidone, memantine, methadone, and so forth.

In still another embodiment, compounds of the invention are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, compounds of the invention are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, compounds of the invention are administered in combination with a prostaglandin receptor agonist, examples of which include, but are not limited to, bimatoprost, latanoprost, travoprost, and so forth.

Compounds of the invention may also be administered in combination with a renin inhibitor, examples of which include, but are not limited to, aliskiren, enalkiren, remikiren, and combinations thereof.

In another embodiment, compounds of the invention are administered in combination with a selective serotonin reuptake inhibitor (SSRI). Representative SSRIs include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, compounds of the invention are administered in combination with a 5-HT1D serotonin receptor agonist, examples of which include, by way of illustration and not limitation, triptans such as almotriptan, avitriptan, eletriptan, frovatriptan, naratriptan, rizatriptan, sumatriptan, and zolmitriptan.

In one embodiment, compounds of the invention are administered in combination with a sodium channel blocker, examples of which include, by way of illustration and not limitation, carbamazepine, fosphenytoin, lamotrigine, lidocaine, mexiletine, oxcarbazepine, phenytoin, and combinations thereof.

In one embodiment, compounds of the invention are administered in combination with a soluble guanylate cyclase stimulator or activator, examples of which include, but are not limited to ataciguat, riociguat, and combinations thereof.

In one embodiment, compounds of the invention are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, compounds of the invention are administered in combination with a vasopressin receptor antagonist, examples of which include, by way of illustration and not limitation, conivaptan and tolvaptan.

Combined secondary therapeutic agents may also be helpful in further combination therapy with compounds of the invention. For example, compounds of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic® or a combination of the calcium channel blocker amlodipine (in the besylate salt form) and the ARB olmesartan (in the medoxomil prodrug form), or a combination of a calcium channel blocker and a statin, all may also be used with the compounds of the invention. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a compound of the invention (30 g), a secondary agent (20 g), 440 g spray-dried lactose and 10 g magnesium stearate are thoroughly blended, and processed as described above.

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

| | |
|---|---|
| AcOH | acetic acid |
| BOC | t-butoxycarbonyl (—C(O)OC(CH$_3$)$_3$) |
| (BOC)$_2$O | di-t-butyl dicarbonate |
| DCC | dicyclohexylcarbodiimide |
| DCM | dichloromethane or methylene chloride |
| DIPEA | N,N-diisopropylethylamine |
| DMA | N,N-dimethylacetamide |
| DMAP | 4-dimethylaminopyridine |
| DMF | N,N-dimethylformamide |
| EDC | 1-(3-dimethylaminopropyl)-3-ethylcarbodiimide |
| Et$_3$N | triethylamine |
| Et$_2$O | diethyl ether |
| Et$_3$SiH | triethylsilane |
| EtOAc | ethyl acetate |
| EtOH | ethanol |
| HATU | N,N,N',N'-tetramethyl-O-(7-azabenzotriazol-1-yl)uronium hexafluorophosphate |
| HCTU | 2-(6-chloro-1H-benzotriazole-1-yl)-1,1,3,3-tetramethylaminium hexafluorophosphate |
| HEPES | 4-(2-hydroxyethyl)-1-piperazineethanesulfonic acid |
| HOBt | 1-hydroxybenzotriazole |
| MeCN | acetonitrile |
| MeOH | methanol |
| NaHMDS | sodium hexamethyldisilazide |
| Pd(dppf)$_2$Cl$_2$ | 1,1-bis(diphenylphosphino) ferrocene palladium chloride |
| Pd(PPh$_3$)$_4$ | tetrakis(triphenylphosphine)palladium(0) |
| PE | petroleum ether |
| PMB | p-methoxybenzyl |
| PyBOP | benzotriazol-1-yloxytris(pyrrolidino)phosphonium hexafluorophosphate |
| SilicaCat ®DPP-Pd | silica based diphenylphosphine palladium (II) catalyst |
| TFA | trifluoroacetic acid |
| THF | tetrahydrofuran |
| TMSCl | Trimethylsilyl chloride |
| Tr | trityl |

Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% H$_2$O/2% MeCN/1.0 mL/L TFA; solvent B was 90% MeCN/10% H$_2$O/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1: (S)-2-(4-Bromobenzyl)-5-oxopyrrolidine-1-carboxylic Acid t-Butyl Ester

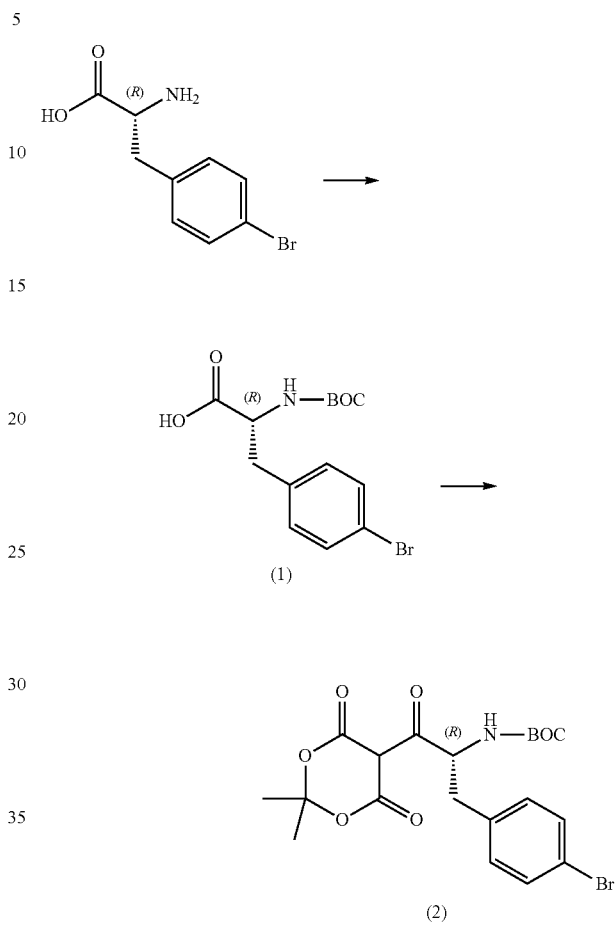

To a solution of (R)-2-amino-3-(4-bromophenyl)propionic acid (50 g, 0.2 mol) in MeCN (700 mL) was added a solution of NaOH (16.4 g, 0.4 mol) in water (700 mL) at −5° C. After stirring for 10 minutes, a solution of (BOC)$_2$O (44.7 g, 0.2 mol) in MeCN (100 mL) was added. The mixture was warmed to room temperature and stirred overnight. After the evaporation of the MeCN, the residue was diluted with DCM (800 mL) and acidified with 1 M HCl to pH 2 at −5° C. The aqueous was extracted with DCM (3×200 mL). The combined organic layers were washed with saturated aqueous NaCl (500 mL), dried over Na$_2$SO$_4$ and concentrated to yield Compound 1 (66.5 g) as a white solid. LC-MS: 366 [M+Na], 709 [2M+Na].

To a solution of Compound 1 (66.5 g, 193 μmol), Meldrum's acid (33.4 g, 232 mmol) and DMAP (37.7 g, 309 mmol) in anhydrous DCM (600 mL), was added dropwise a solution of DCC (47.9 g, 232 mmol) in anhydrous DCM (200 mL) over 1 hour at −5° C. under nitrogen. The mixture was stirred at −5° C. for 8 hours, then refrigerated overnight. Crystals of dicyclohexylurea were observed. The mixture was filtered, washed with 5% KHSO$_4$ (5×200 mL) and saturated aqueous NaCl (200 mL), then dried over anhydrous MgSO$_4$ under refrigeration overnight. The solution was then evaporated to yield crude Compound 2 (91 g) as a light yellow solid. LC-MS: 492 [M+Na], 961 [2M+Na].

(2) →

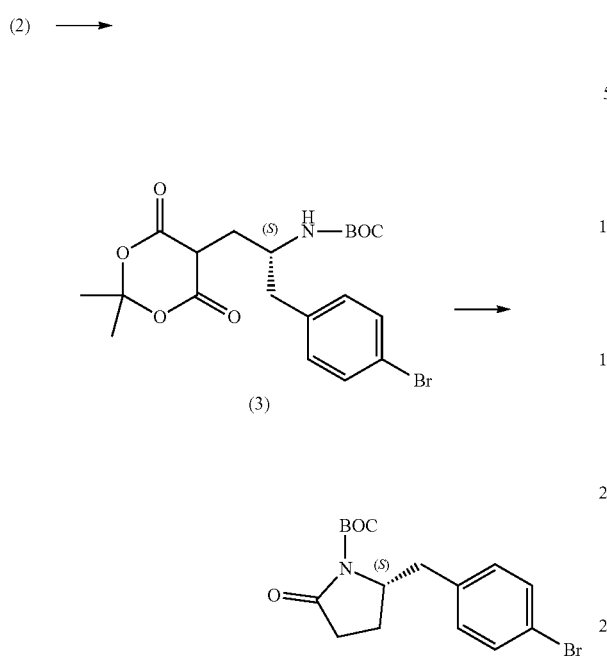

To a solution of crude Compound 2 (91 g, 193 mmol) in anhydrous DCM (1 L) was added AcOH (127.5 g, 2.1 mol) at −5° C. under nitrogen. The mixture was stirred at −5° C. for 30 minutes, then NaBH$_4$ (18.3 g, 483 mmol) was added in small portions over 1 hour. After stirring for another 1 hour at −5° C., saturated aqueous NaCl (500 mL) was added. The organic layer was washed with saturated aqueous NaCl (2×300 mL) and water (2×300 mL), dried over MgSO$_4$, filtered, and concentrated to yield the crude product, which was further purified by washing with Et$_2$O to yield Compound 3 (68 g) as a light yellow solid. LC-MS: 478 [M+Na], 933 [2M+Na].

A solution of Compound 3 (68 g, 149 mmol) in anhydrous toluene (500 mL) was refluxed under nitrogen for 3 hours. After evaporation of the solvent, the residue was purified by chromatography (hexanes:EtOAc=10:1) to yield the title compound (38 g) as a light yellow oil. LC-MS: 376 [M+Na], 729 [2M+Na].

Preparation 2: (3R,5R)-5-(3′-Chlorobiphenyl-4-ylmethyl)-1-(2,2-dimethylpropionyl)-3-hydroxypyrrolidin-2-one

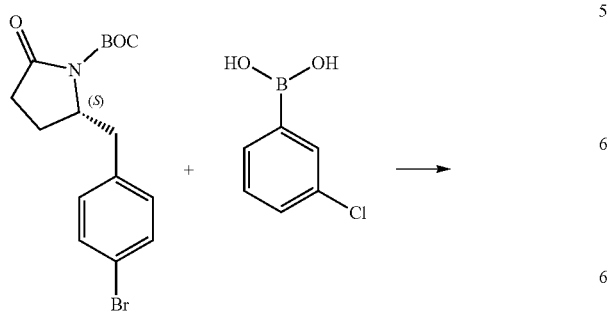

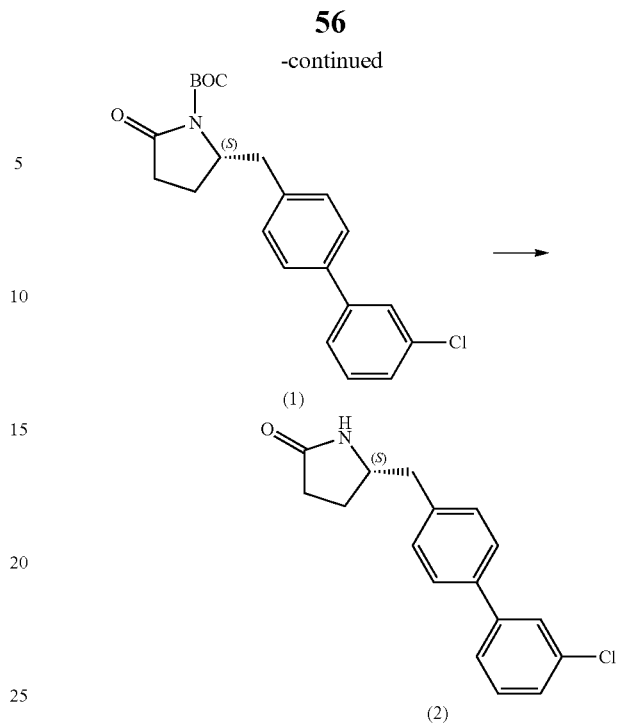

To a solution of (S)-2-(4-bromobenzyl)-5-oxopyrrolidine-1-carboxylic acid t-butyl ester (15 g, 43 mmol) in 1,4-dioxane (600 mL) was added 3-chlorophenylboronic acid (8 g, 51 mmol) and Pd(dppf)$_2$C$_2$ (3.1 g, 4.2 mmol) at room temperature under nitrogen. After stirring for 10 minutes, a solution of K$_2$CO$_3$ (11.7 g, 85 mmol) in water (60 mL) was added. The mixture was heated to 60° C. and stirred overnight. After evaporation of the solvent, water (200 mL) was added and extracted with EtOAc (3×200 mL). The combined organic layers were washed with saturated aqueous NaCl (400 mL), dried over Na$_2$SO$_4$, and concentrated to yield the crude product which was further purified by column chromatography (hexanes:EtOAc=6:1) to yield Compound 1 (15 g) as a light yellow solid. LC-MS: 408 [M+Na].

To a solution of Compound 1 (15 g, 0.039 mol) in anhydrous DCM (250 mL) was added TFA (20 mL, 270 mmol) at −5° C. under nitrogen. The mixture was warmed to room temperature and stirred overnight. After evaporation of the solvent, the residue was diluted with EtOAc (300 mL), then washed with saturated aqueous NaHCO$_3$ (3×200 mL), water (200 mL), saturated aqueous NaCl (250 mL), then dried over Na$_2$SO$_4$ and concentrated to yield crude Compound 2 (11 g) as a light yellow solid. LC-MS: 286 [M+H].

(2) →

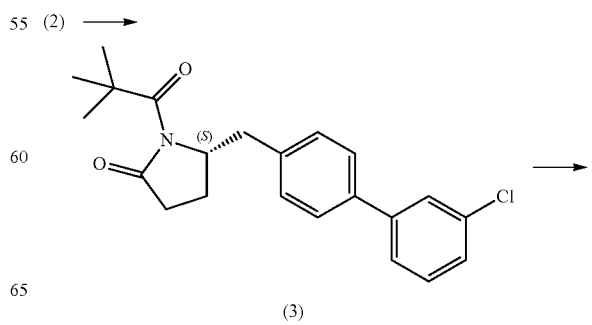

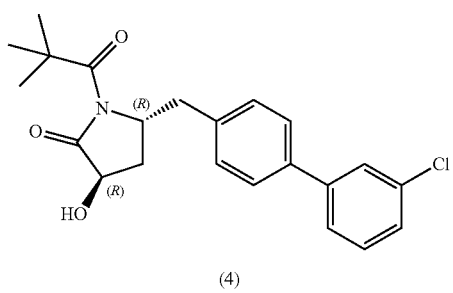

(4)

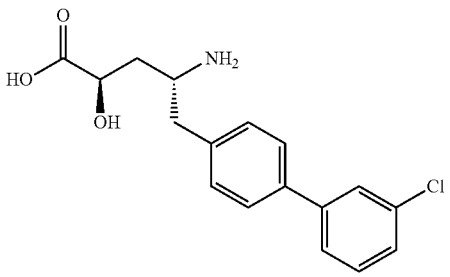

(1)

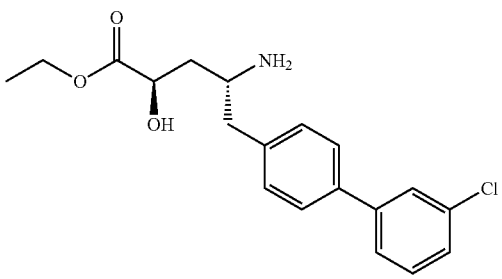

To a solution of NaH (2.3 g, 98 mmol) in anhydrous THF (200 mL) was added dropwise a solution of Compound 2 (11 g, 39 mmol) in anhydrous THF (100 mL) over 30 minutes at 0° C. under nitrogen. The mixture was warmed to room temperature and stirred for 2 hours. After cooling to 0° C., pivaloyl chloride (6 g, 51 mmol) was added dropwise over 30 minutes. The mixture was warmed to room temperature and stirred overnight. The reaction was quenched with saturated aqueous NH$_4$Cl (200 mL) and extracted with EtOAc (3×200 mL). The combined organic layers were washed with saturated aqueous NaCl (300 mL), dried over MgSO$_4$, filtered, and concentrated to yield the crude product which was further purified by chromatography (hexanes:EtOAc=25:1) to yield Compound 3 (10.5 g) as a light yellow solid. LC-MS: 391 [M+Na].

To a solution of Compound 3 (10.5 g, 29 mmol) in anhydrous THF (120 mL) was added dropwise NaHMDS (29 mL, 58 mmol) over 30 minutes at −78° C. under nitrogen. After stirring at −78° C. for 90 minutes, a solution of (+)-(8,8-dichlorocamphorylsulfonyl)oxaziridine (15.6 g, 52 mmol) was added dropwise over 30 minutes. After stirring at −78° C. for 2 hours, the reaction was quenched with saturated NH$_4$Cl (400 mL) and extracted with EtOAc (3×300 mL). The combined organic layers were washed with saturated aqueous NaCl (300 mL), dried over MgSO$_4$, filtered, and concentrated to give the crude product which was further purified by chromatography (hexanes:EtOAc=15:1) to yield the title compound (9.6 g) as a light yellow solid. LC-MS: 408 [M+Na].

Preparation 3: (2R,4R)-4-Amino-5-(3'-chlorobiphenyl-4-yl)-2-hydroxypentanoic Acid Ethyl Ester

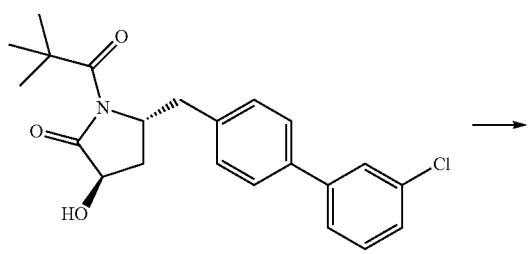

A solution of (3R,5R)-5-(3'-chlorobiphenyl-4-ylmethyl)-1-(2,2-dimethylpropionyl)-3-hydroxypyrrolidin-2-one (9.6 g, 25 mmol) in concentrated HCl (81 mL, 81 mmol) was heated at 100° C. for 16 hours. The mixture was then concentrated to give the crude product which was further purified by washing with Et$_2$O to yield Compound 1 (5.7 g) as a light yellow solid HCl salt. LC-MS: 320 [M+H].

To a solution of Compound 1 (5.7 g, 18 mmol) in EtOH (10 mL) was added 8M HCl in EtOH (120 mL, 960 mmol) at room temperature. The mixture was heated at 50° C. for 16 hours. After concentration, the crude product was further purified by washing with Et$_2$O to yield the title compound (2.1 g) as a light yellow solid HCl salt. LC-MS: 348 [M+H].

Preparation 4: (2R,4R)-5-(3'-Chlorobiphenyl-4-yl)-2-hydroxy-4-[(3-hydroxy-3H-benzotriazole-5-carbonyl)amino]pentanoic Acid Ethyl Ester

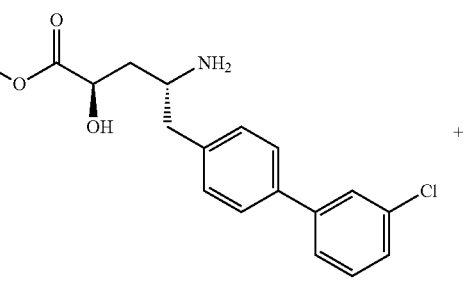

+

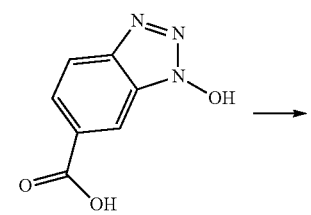

-continued

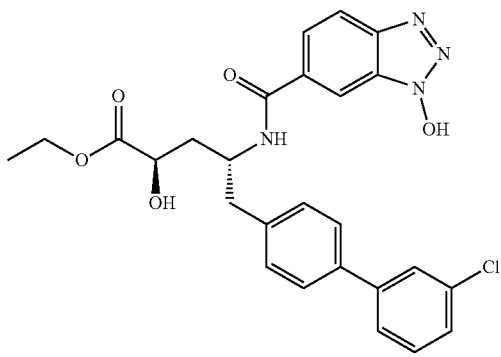

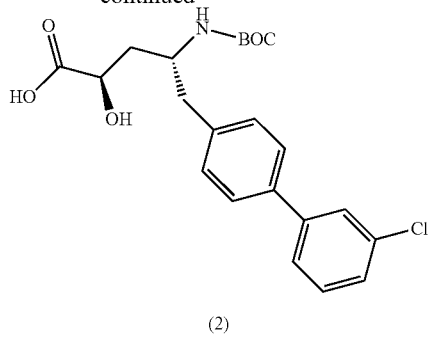

(2)

HATU (328 mg, 862 µmol) was added to a solution of 1-hydroxy-1H-1,2,3-benzotriazole-6-carboxylic acid (154 mg, 862 µmol) in DMF (1.5 mL, 19.5 mmol) and the resulting mixture was stirred at room temperature for 10 minutes. DIPEA (0.3 mL, 1.7 mmol) was added to the mixture, followed by (2R,4R)-4-amino-5-(3'-chlorobiphenyl-4-yl)-2-hydroxypentanoic acid ethyl ester (200 mg, 575 µmol) and the mixture was stirred at room temperature for 1 hour. The mixture was concentrated in vacuo and the resulting residue was purified by reverse phase chromatography (35-80% MeCN in water with 0.05% TFA) to yield the title compound (197 mg) as a white solid.

A solution of (3R,5R)-5-(3'-chlorobiphenyl-4-ylmethyl)-1-(2,2-dimethylpropionyl)-3-hydroxypyrrolidin-2-one (4.5 g, 11.7 mmol) in concentrated HCl (30 mL) was stirred at 100° C. for 16 hours. The mixture was concentrated in vacuo to yield Compound 1 (4 g) as a white solid HCl salt. LC-MS: 321 [M+H]+.

To a solution of NaOH (1.8 g, 45.2 mmol) in water (100 mL), was added Compound 1 (4 g, 11.3 mmol) in MeCN (100 mL) dropwise. The mixture was stirred for 10 minutes at 0° C. Di-t-butyldicarbonate (7.17 g, 33.8 mmol) was added and the mixture was stirred for 15 hours at room temperature. The resulting mixture was concentrated in vacuo to remove MeCN, then diluted with DCM (300 mL), and the pH adjusted to pH=5-6 with 1N aqueous HCl. Then the organic layer was collected and the residue was extracted with DCM (3×300 mL). The combined organic layers were concentrated and washed with hexanes (150 mL) to yield the title compound (4 g) as a white solid. LC-MS: 442 [M+Na]+.

Preparation 5: (2R,4R)-4-t-Butoxycarbonylamino-5-(3'-chlorobiphenyl-4-yl)-2-hydroxypentanoic Acid Preparation 6: (2R,4R)-4-Amino-5-(3'-chlorobiphenyl-4-yl)-2-hydroxypentanoic Acid 2,2,3,3,3-pentafluoropropyl Ester

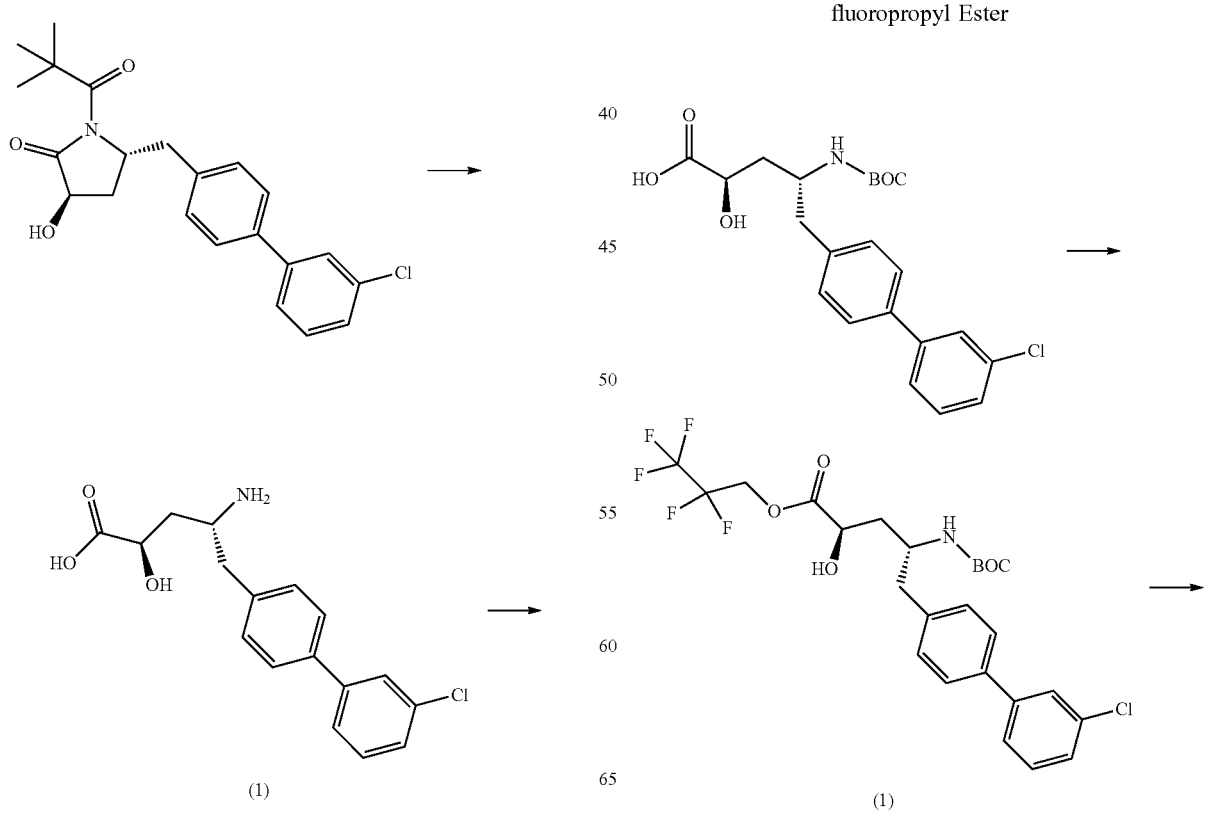

-continued

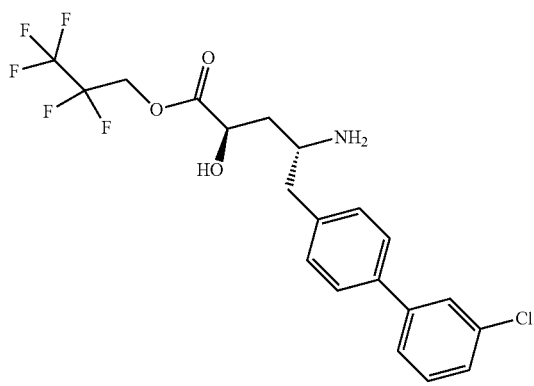

To a solution of (2R,4R)-4-t-butoxycarbonylamino-5-(3'-chlorobiphenyl-4-yl)-2-hydroxypentanoic acid (0.9 g, 6 mmol) and 2,2,3,3,3-pentafluoropropan-1-ol (450 mg, 3 mmol) in DCM (30 mL) was added DCC (880 mg, 4.3 mmol) and DMAP (260 mg, 2.1 mmol). The resulting mixture was stirred for 15 hours at room temperature, then concentrated in vacuo. The residue was dissolved in EtOAc (100 mL) and washed with water (30 mL) and saturated aqueous NaCl (30 mL). The organic layer was collected and concentrated and purified by column chromatography (hexanes/EtOAc=5:1) to yield Compound 1 (0.4 g) as a white solid. LC-MS: 574 [M+Na]+.

A solution of Compound 1 (0.4 g, 690 μmol) in 1.4 M HCl in a 1,4-dioxane solution (15 mL) was stirred overnight, and then concentrated in vacuo. The residue was dispersed in EtOAc (10 mL), and the precipitate was collected by filtration to yield the title compound as an off-white solid HCl salt (165 mg). LC-MS: 452 [M+H]+. 1H NMR: (DMSO-d6) 1.95-1.82 (m, 2H), 2.99-2.98 (m, 2H), 3.56 (br, 1H), 4.41-4.38 (m, 1H), 4.92-4.82 (m, 2H), 6.35 (s, 1H), 7.71-7.38 (m, 8H), 8.09 (s, 3H).

Preparation 7: (2R,4R)-4-Amino-5-(3'-chlorobiphenyl-4-yl)-2-hydroxypentanoic Acid 5-Methyl-2-oxo[1,3]dioxol-4-ylmethyl Ester

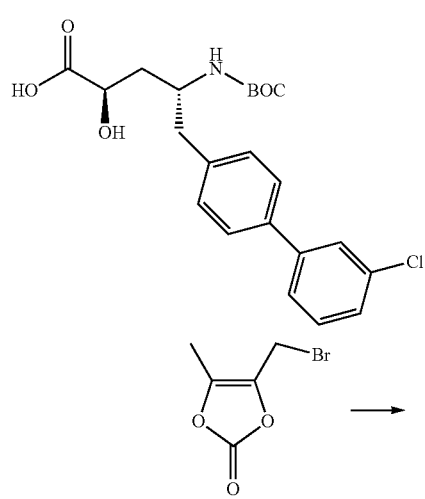

-continued

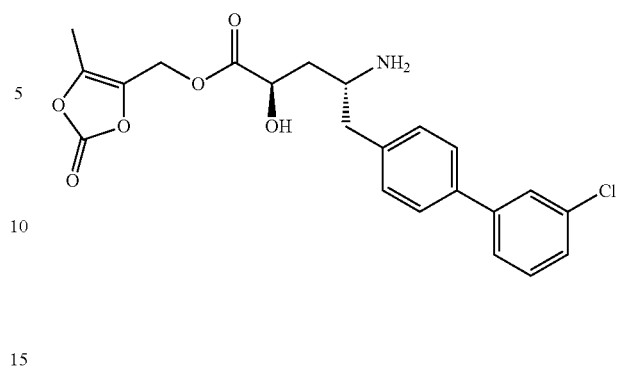

A suspension of (2R,4R)-4-t-butoxycarbonylamino-5-(3'-chlorobiphenyl-4-yl)-2-hydroxypentanoic acid (740 mg, 1.8 mmol), 4-(bromomethyl)-5-methyl-1,3-dioxol-2-one (340 mg, 1.8 mmol), potassium iodide (58 mg, 350 μmol), and K2CO3 (486 mg, 3.5 mmol) in DMF (20 mL) was stirred for 4 hours at room temperature. The mixture was diluted with EtOAc (150 mL) and washed with water (30 mL). The organic layer was collected and concentrated and purified by column chromatography (hexanes/EtOAc=1:1) to yield a white solid (490 mg). LC-MS: 554 [M+23]+. A solution of this solid (476 mg, 890 pimp in 3 N HCl in 1,4-dioxane (20 mL) was stirred overnight, and then concentrated in vacuo.

The residue was dispersed in EtOAc (10 mL), and the precipitate was collected by filtration to yield the title compound as an off-white solid (290 mg). LC-MS: 432 [M+H]+. 1H NMR: (DMSO-d6) 1.92-1.82 (m, 2H), 2.16 (s, 3H), 2.99 (br, 2H), 3.56 (br, 1H), 4.35-4.32 (m, 1H), 5.017 (s, 2H), 6.17 (s, 1H), 7.39-7.36 (m, 4H), 7.71-7.68 (m, 4H), 8.05 (s, 3H).

Preparation 8: (2R,4R)-4-Amino-5-(3'-chlorobiphenyl-4-yl)-2-hydroxypentanoic Acid Butyryloxymethyl Ester

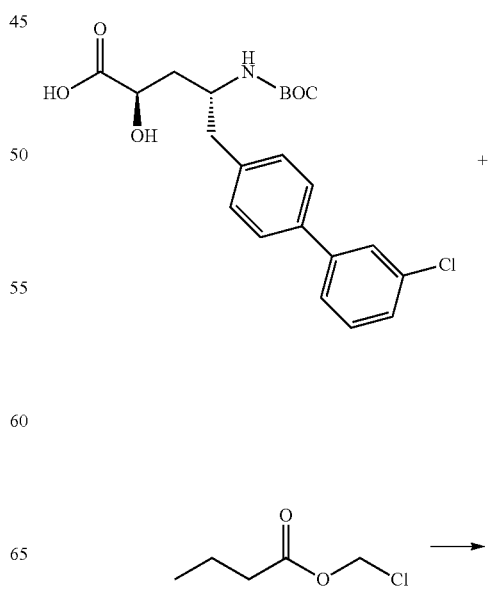

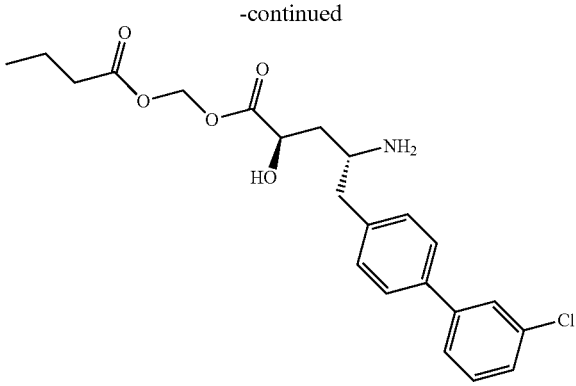

A solution of (2R,4R)-4-t-butoxycarbonylamino-5-(3'-chlorobiphenyl-4-yl)-2-hydroxypentanoic acid (900 mg, 2.1 mmol), chloromethyl butyrate (350 mg, 2.6 mmol), sodium iodide (481 mg, 3.21 mmol) and DIPEA (828 mg, 6.42 mmol) in DMF (20 mL) was stirred for 16 hours at 30° C. The mixture was diluted with EtOAc (150 mL) and washed with water (50 mL) and saturated aqueous NaCl (50 mL). The organic layer was collected and concentrated and purified by column chromatography (hexanes/EtOAc=5:1) to yield a white solid (240 mg). LC-MS: 542 [M+Na]$^+$. A solution of this solid (240 mg, 460 μmol) in 1.4 M HCl in 1,4-dioxane (15 mL) was stirred overnight, and then concentrated in vacuo. The residue was dispersed in EtOAc (10 mL), and the precipitated was collected by filtration to yield the title compound as an off-white solid HCl salt (140 mg). LC-MS: 420 [M+H]$^+$. $^1$H NMR: (DMSO) 0.85 (t, J=7.5 Hz, 3H), 1.61-1.52 (m, 2H), 1.89-1.86 (m, 2H), 2.30 (t, J=7.5 Hz, 2H), 2.98 (br, 2H), 3.56 (br, 1H), 4.33-4.30 (m, 1H), 5.74-5.68 (m, 2H), 6.21 (s, 1H), 7.37-7.35 (m, 4H), 7.70-7.767 (m, 4H), 8.01 (brs, 3H).

Preparation 9: (2R,4R)-4-Amino-5-(4-bromophenyl)-2-hydroxypentanoic Acid Ethyl Ester

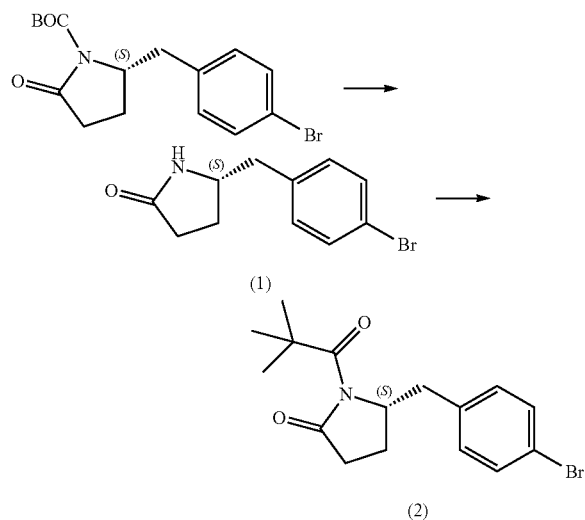

To a solution of (S)-2-(4-bromobenzyl)-5-oxopyrrolidine-1-carboxylic acid t-butyl ester (38 g, 107 mmol) in anhydrous DCM (250 mL) was added TFA (20 mL, 0.27 mol) at −5° C. under nitrogen. The mixture was warmed to room temperature and stirred overnight. After evaporation of the solvent, the residue was diluted with EtOAc (300 mL) and washed with saturated aqueous NaHCO$_3$ (3×200 mL), water (200 mL), saturated aqueous NaCl (250 mL), dried over Na$_2$SO$_4$ and concentrated to yield crude Compound 1 (24 g) as a light yellow solid. LC-MS: 254 [M+H].

To a solution of NaH (8.6 g, 250 mmol) in anhydrous THF (200 mL) was added dropwise a solution of Compound 1 (24 g, 94 mmol) in anhydrous THF (200 mL) over 30 minutes at 0° C. under nitrogen. The mixture was warmed to room temperature and stirred for 2 hours. After cooling to 0° C., pivaloyl chloride (18 g, 150 mmol) was added dropwise over 30 minutes. The mixture was warmed to room temperature and stirred overnight. The reaction was quenched with saturated aqueous NH$_4$Cl (300 mL) and extracted with EtOAc (3×200 mL). The combined organic layers were washed with saturated aqueous NaCl (300 mL), dried over MgSO$_4$, filtered and concentrated to yield the crude product, which was further purified by chromatography (hexanes:EtOAc=25:1) to yield Compound 2 (18 g) as a light yellow solid. LC-MS: 360 [M+Na].

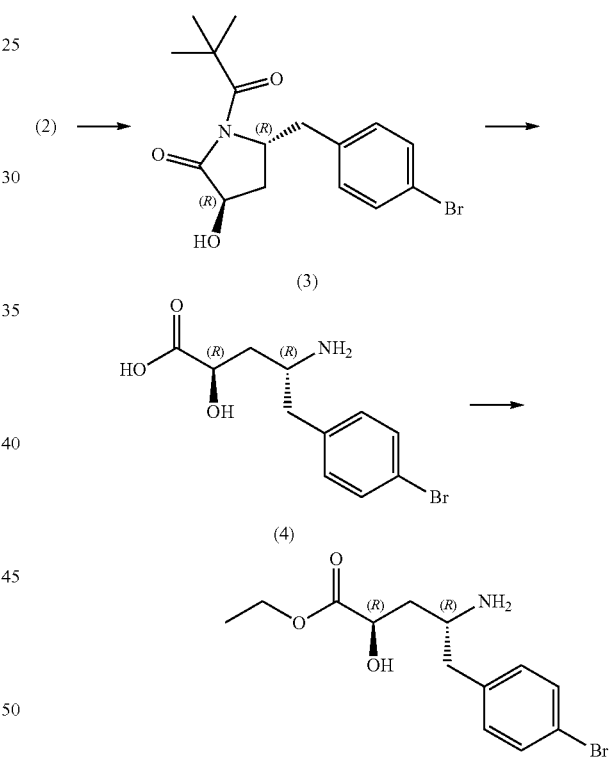

To a solution of Compound 2 (18 g, 53 mmol) in anhydrous THF (250 mL) was added dropwise NaHMDS (47.7 mL, 96 mmol) over 30 minutes at −78° C. under nitrogen. After stirring at −78° C. for 90 minutes, a solution of (+)-(8,8-dichlorocamphorylsulfonyl)-oxaziridine (31.6 g, 106 mmol) was added dropwise over 30 minutes. After stirring at −78° C. for 2 hours, the reaction was quenched with saturated aqueous NH$_4$Cl (400 mL) and extracted with EtOAc (3×300 mL). The combined organic layers were washed with saturated aqueous NaCl (300 mL), dried over MgSO$_4$, filtered, and concentrated to give the crude product which was further purified by chromatography (hexanes: EtOAc=15:1) to yield Compound 3 (8.9 g) as a light yellow solid. LC-MS: 376 [M+Na].

A solution of Compound 3 (8.9 g, 25 mmol) in concentrated HCl (81 mL, 81 mmol) was heated at 100° C. for 16 hours. The mixture was then concentrated to yield the crude product which was further purified by washing with Et$_2$O to yield Compound 4 (7 g) as a light yellow solid HCl salt. LC-MS: 323 [M+H].

A solution of Compound 4 (7 g, 22 mmol) in EtOH (10 mL) was combined with 8M HCl in EtOH (120 mL, 960 mmol) at room temperature. The mixture was heated at 50° C. for 16 hours, then concentrated. The crude product was further purified by washing with Et$_2$O to yield the title compound (6 g) as a light yellow solid HCl salt. LC-MS: 352 [M+H].

Preparation 10:
5-Hydroxy-1-pyridin-2-yl-1H-pyrazole-3-carboxylic Acid

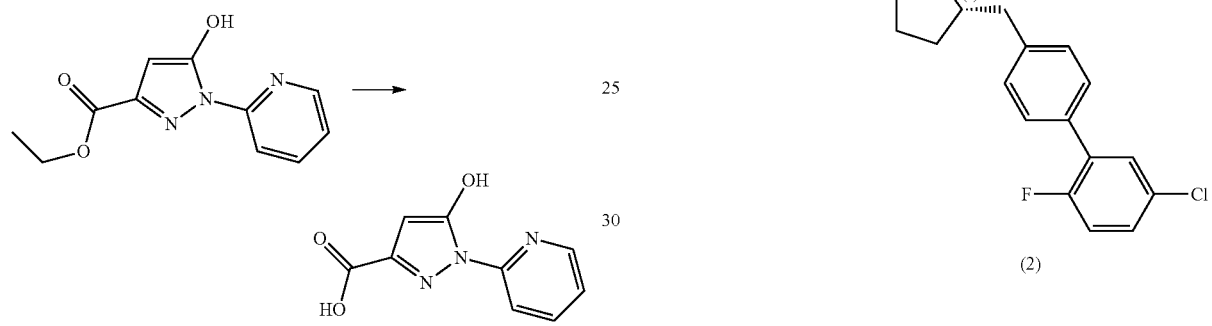

To a suspension of 5-hydroxy-1-pyridin-2-yl-1h-pyrazole-3-carboxylic acid ethyl ester (351.6 mg, 1.5 mmol) in MeOH (5.0 mL, 120 mmol) at room temperature was added LiOH monohydrate (126.5 mg, 3.0 mmol), forming a clear solution. The solution was stirred at room temperature overnight. The solution was then concentrated. To the resulting residue was added 1N aqueous HCl to achieve pH-2, forming a precipitate. Water (4.0 mL) was added and the resulting mixture was stirred at room temperature for 1 hour, then filtered. The solids were rinsed with water and dried under vacuum to yield the title compounds as a white solid (128 mg).

Preparation 11: (2R,4R)-4-Amino-5-(5'-chloro-2'-fluoro-biphenyl-4-yl)-2-hydroxypentanoic Acid

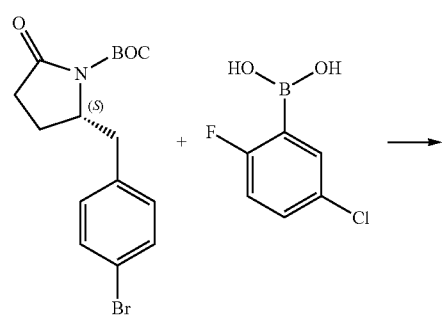

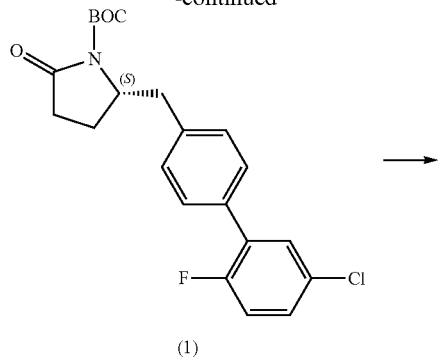

To a solution of (S)-2-(4-bromobenzyl)-5-oxopyrrolidine-1-carboxylic acid t-butyl ester (25 g, 70.6 mmol) in 1,4-dioxane (500 mL) was added 5-chloro-2-fluorophenylboronic acid (24.6 g, 141 mmol), Pd(PPh$_3$)$_4$ (4.1 g, 3.5 mmol) and a solution of K$_2$CO$_3$ (17.8 g, 141 mmol) in water (90 mL), at room temperature under nitrogen. The mixture was heated to 60° C. and stirred overnight. Water (500 mL) was added and the solvent evaporated. The mixture was extracted with EtOAc (3×200 mL). The combined organic layers were washed with saturated aqueous NaCl (300 mL) and filtered. The filtrate was concentrated to yield the crude product which was purified by chromatography to yield Compound 1 (22.7 g) as a light yellow solid. LC-MS: 829.2 [2M+Na$^+$].

To a solution of Compound 1 (4.9 g, 12.1 mol) in DCM (100 mL) was added TFA (4.5 mL, 60.7 mmol) at 0° C. under nitrogen, and stirred for 1 hour. The mixture was warmed to room temperature for 1.5 hours. After evaporation of the solvent, the residue was diluted with EtOAc (100 mL), then washed with saturated aqueous NaHCO$_3$ (3×100 mL), water (2×100 mL), saturated aqueous NaCl (100 mL), then dried over Na$_2$SO$_4$. The mixture was filtered and the filtrate was concentrated to yield crude Compound 2 (combined with a separate lot for a total of 16.9 g). LC-MS: 304 [M+H].

(2) →

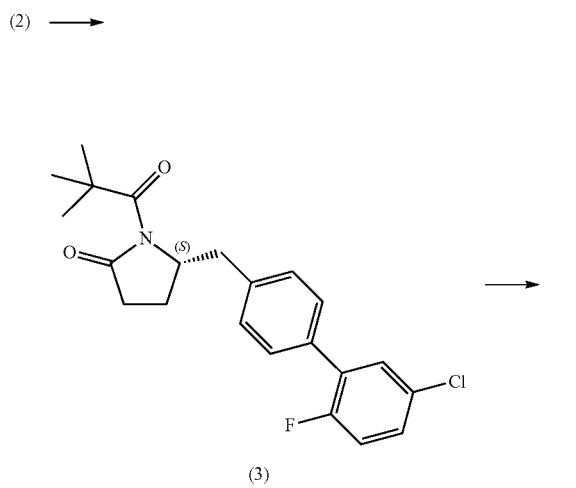

(3)

To a solution of NaH (2.4 g, 695 mmol) in THF (200 mL) was added dropwise a solution of Compound 2 (8.5 g, 278 mmol) in THF (50 mL) at 0° C. under nitrogen. The mixture was warmed to room temperature and stirred for 2 hours. After cooling to 0° C., pivaloyl chloride (5 g, 41.7 mmol) was added dropwise over 30 minutes. The mixture was warmed to room temperature and stirred for 9.5 hours. The reaction was quenched with saturated aqueous $NH_4Cl$ (250 mL) and extracted with EtOAc (3×400 mL). The combined organic layers were dried over $Na_2SO_4$ and concentrated to yield the crude product which was purified by chromatography to yield Compound 3 (18 g) as a yellow solid. LC-MS: 388 [M+H$^+$].

To a solution of Compound 3 (9 g, 23.2 mmol) in THF (200 mL) was added dropwise NaHMDS (20.9 mL, 41.8 mmol) at −78° C. under nitrogen. After stirring for 1 hour at −78° C., a solution of (+)-(8,8-dichlorocamphorylsulfonyl) oxaziridine (10.4 g, 34.8 mmol) in THF (50 mL) was added dropwise. After stirring at −78° C. for 1 hour, the reaction was quenched with saturated aqueous $NH_4Cl$ (50 mL) and extracted with EtOAc (3×400 mL). The combined organic layers were washed with 1M HCl (400 mL), saturated aqueous $NaHCO_3$ (400 mL), and saturated aqueous NaCl (400 mL), dried over $Na_2SO_4$, and concentrated to give the crude product which was purified by chromatography to yield Compound 4 (8.8 g) as a white semi-solid. LC-MS: 426.1 [M+Na$^+$].

(4) →

A solution of Compound 4 (8.8 g, 21.8 mmol) in EtOH (12 mL) was added to concentrated HCl (200 mL) and heated at 100° C. and stirred overnight. The mixture was then concentrated to give the crude product which was purified by washing with Et$_2$O (100 mL) to yield the title compound as a solid HCl salt (7.5 g). LC-MS: 338 [M+H$^+$].

Preparation 12: (2R,4R)-4-Amino-5-(5'-chloro-2'-fluorobiphenyl-4-yl)-2-hydroxypentanoic Acid Ethyl Ester A solution of Compound 5 (7.5 g, 20.1 mmol) in EtOH/HCl (100 mL) was heated at 50° C. overnight. The mixture was concentrated and the crude product was purified by washing with Et$_2$O (200 mL) to yield the title compound (6.5 g) as a white solid HCl salt. LC-MS: 366.1 [M+H$^+$].

Preparation 13: (2R,4R)-5-(4-Bromophenyl)-2-hydroxy-4-[(1-hydroxy-1H-1,2,3-triazole-4-carbonyl)amino]pentanoic Acid Ethyl Ester

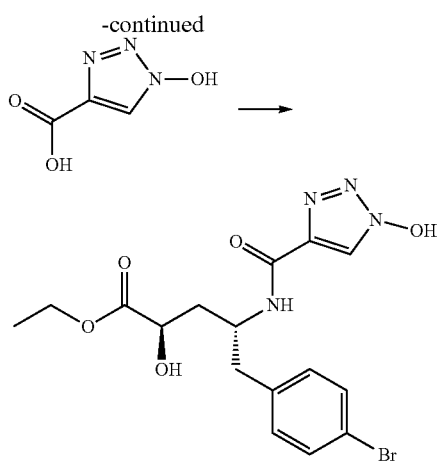

1-Hydroxy-1H-1,2,3-triazole-4-carboxylic acid was prepared by combining 1-hydroxy-1H-[1,2,3]triazole-4-carboxylic acid ethyl ester (2.0 g, 13 mmol), EtOH (25 mL, 430 mmol), and a pre-dissolved solution of LiOH monohydrate (1.6 g, 38.2 mmol) and water (10 mL, 600 mmol). The mixture was stirred at room temperature for 4 hours, then partially concentrated and acidified with HCl to cause precipitation. The solid was filtered and dried under vacuum to give 1.3 g of the desired acid.

1-Hydroxy-1H-1,2,3-triazole-4-carboxylic acid (163 mg, 1.3 mmol) was combined with HCTU (523 mg, 1.3 mmol) and DMF, and stirred for 5 minutes at room temperature. DIPEA (661 µL, 3.8 mmol) and (2R,4R)-4-amino-5-(4-bromophenyl)-2-hydroxypentanoic acid ethyl ester (0.400 g, 1.26 mmol) were added, and the resulting mixture was stirred for 10 minutes. The mixture was evaporated under reduced pressure and purified (C18 column; 20-70% MeCN in water with 5% TFA) to yield the title compound (330 mg).

Preparation 14: 5-(4-Methoxybenzyloxy)-1-methyl-1H-pyrazole-3-carboxylic Acid

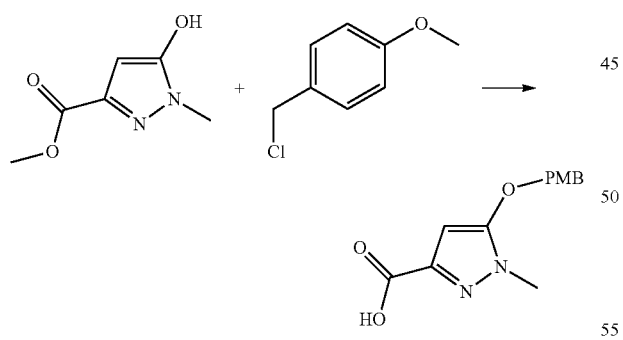

To a stirred solution of 5-hydroxy-1-methyl-1H-pyrazole-3-carboxylic acid methyl ester (200 mg, 1 mmol) in DMF (992 µL, 12.8 mmol) at 0° C. was added K$_2$CO$_3$ (195 mg, 1.4 mmol). After 10 minutes at 0° C. p-methoxybenzyl chloride (208 µL, 1.5 mmol) was added, and the resulting mixture was stirred at 60° C. for 1 hour, before allowing to cool to room temperature. MeOH (2.6 mL, 63.2 mmol) was added, followed by LiOH (61.4 mg, 2.6 mmol) in water (2.6 mL, 142 mmol), and the reaction was monitored for completion. The solvent was removed in vacuo. Water was added to the vial and the crude product was acidified with a 1N HCl aqueous solution. The solids were filtered to yield the title compound as a white solid (350 mg).

Preparation 15: (2R,4R)-5-(3'-Chlorobiphenyl-4-yl)-2-hydroxy-4-{[5-(4-methoxybenzyloxy)-1-methyl-1H-pyrazole-3-carbonyl]amino}pentanoic Acid

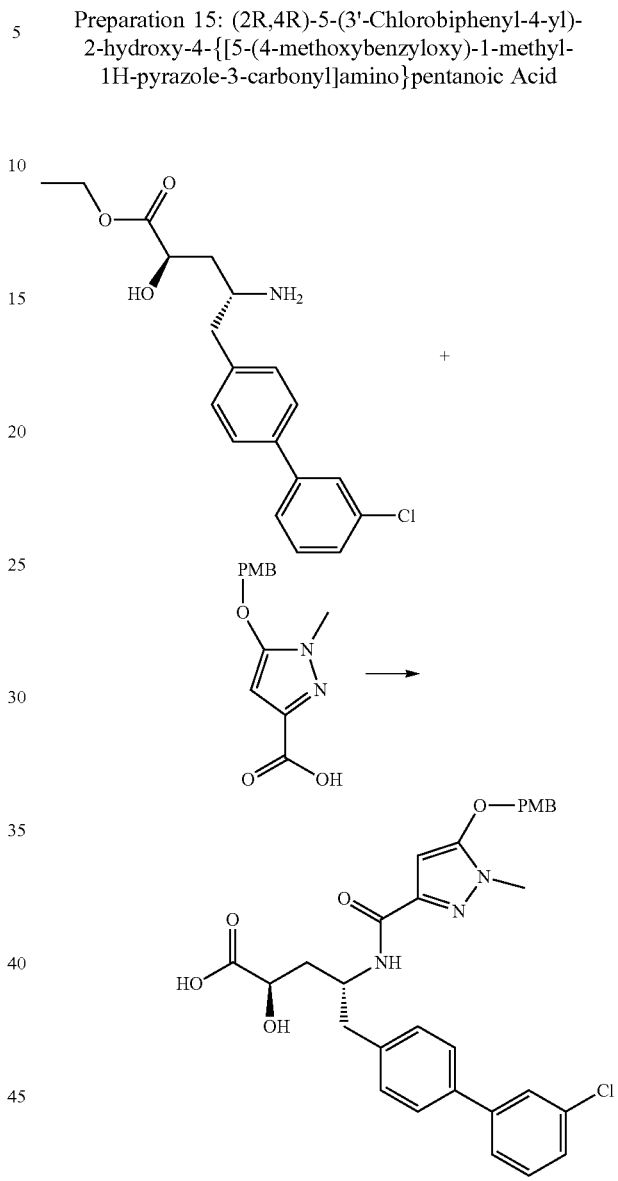

5-(4-Methoxy-benzyloxy)-1-methyl-1H-pyrazole-3-carboxylic acid (118.8 mg, 453 µmol) was combined with HCTU (187.3 mg, 453 µmol) and DMF (2.0 mL, 25.9 mmol). The mixture was stirred at room temperature for 15 minutes. DIPEA (225 µL, 1.3 mmol) and (2R,4R)-4-amino-5-(3'-chlorobiphenyl-4-yl)-2-hydroxypentanoic acid ethyl ester (150 mg, 430 µmol) were added and the mixture was stirred at room temperature for 15 minutes. The solvent was removed in vacuo. EtOH (1.5 mL, 25.9 mmol) was added, followed by a solution of 1 M LiOH in water (4.3 mL, 4.3 mmol). The mixture was stirred at room temperature for 1 hour. The solvent was removed in vacuo and the product was purified by reverse phase chromatography to yield the title compound (171 mg).

Preparation 16:
3-(2-Fluorophenyl)-isoxazole-5-carbonyl Chloride

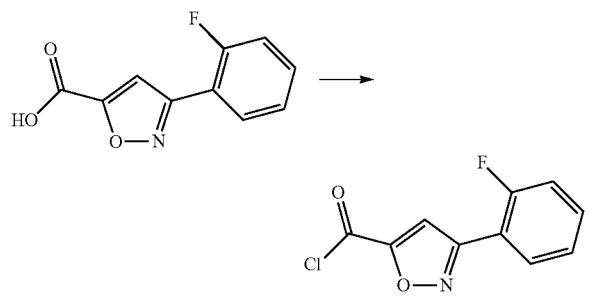

Oxalyl chloride (0.07 mL, 0.74 mmol) was added dropwise to a stirred solution of 3-(2-fluorophenyl)isoxazole-5-carboxylic acid (77 mg, 370 μmol) in THF (10 mL). The mixture was stirred at room temperature for 2 hours, then concentrated to yield the title compound (79 mg), which was used without further purification.

Preparation 17: 3-Methoxyisoxazole-5-carbonyl Chloride

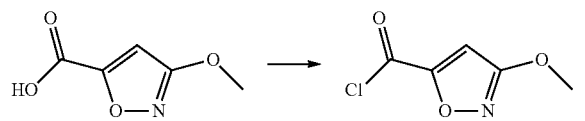

To a solution of 3-methoxyisoxazole-5-carboxylic acid (420 mg, 3 mmol) in THF (15 mL) and DMF (1 drop) was added dropwise oxalyl chloride (650 μL, 7 mmol) at 0° C. The mixture was then stirred at room temperature for 3 hours. The solution was concentrated in vacuo to yield the title compound as a light yellow oil (430 mg).

Preparation 18:
(S)-2-t-Butoxycarbonylamino-3-methylbutyric Acid Chloromethyl Ester

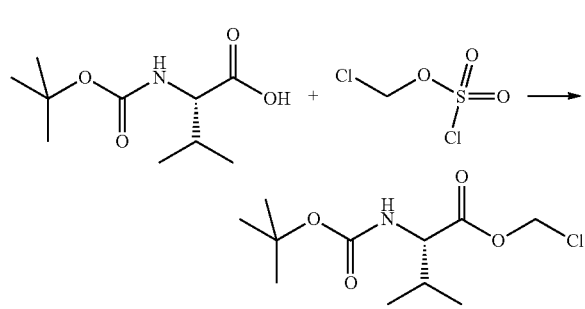

To a mixture of (S)-2-(t-butoxycarbonylamino)-3-methylbutanoic acid (28.6 g, 130 mmol) and NaHCO$_3$ (44 g, 520 mmol) and Bu$_4$NHSO$_4$ (4.4 g, 13 mmol) in DCM (200 mL) and water (200 mL) was added chloromethyl sulfochloridate (26 g, 158 mmol) at 0° C. The mixture was stirred at room temperature for 24 hours, and then was extracted with DCM (3×150 mL). The combined organic layers were washed with water (2×300 mL), and the DCM layer was purified by flash column (petroleum ether:EA=15:1) to yield the title compound as a yellow solid (35 g). LC-MS: 266 [M+H]$^+$.

Preparation 19:
(S)-2-Methoxycarbonylamino-3-methylbutyric Acid Chloromethyl Ester

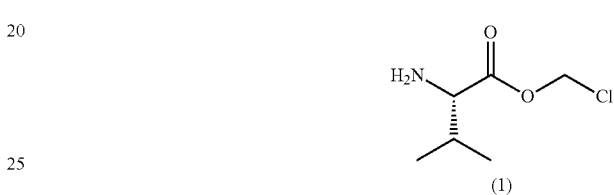

A solution of (S)-2-t-butoxycarbonylamino-3-methylbutyric acid chloromethyl ester (35 g, 132 mmol) in DCM (200 mL) was added dropwise a solution of TFA (50 mL) in DCM (100 mL) at 0° C. The resulting mixture was stirred at room temperature overnight and then concentrated in vacuo to yield crude Compound 1 as a yellow oil (21.8 g). LC-MS: 166 [M+H]$^+$.

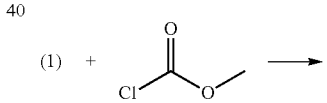

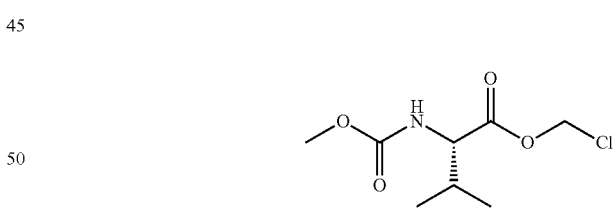

To a mixture of Compound 1 (21.8 g, 139 mmol) and methyl chloroformate (12 mL, 157 mmol) in THF (1 L) was added TEA (38 mL, 278 mmol) at 0° C. The resulting mixture was stirred at room temperature for 12 hours, then concentrated in vacuo. The residue was purified by flash column (petroleum ether:EtOAc=6:1) to yield the title compound as a yellow solid (20.3 g). LC-MS: 224 [M+H]$^+$. $^1$H NMR (400 MHz, DMSO-d$_6$): δ 0.97-1.02 (m, 6H), 2.16-2.21 (m, 1H), 3.68 (s, 1H), 4.14 (d, J=4 Hz, 1H), 5.76-5.91 (m, 2H).

Preparation 20:
(2R,4R)-4-Amino-5-biphenyl-4-yl-2-hydroxypentanoic Acid Ethyl Ester

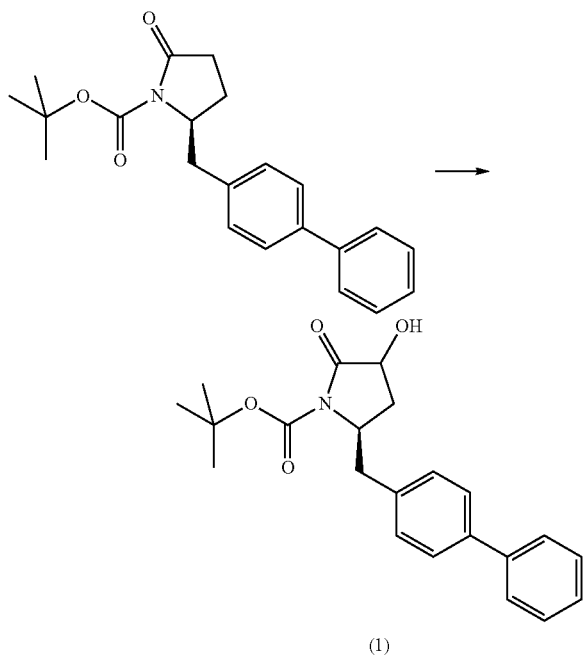

(1)

To a stirred solution of (S)-2-biphenyl-4-ylmethyl-5-oxopyrrolidine-1-carboxylic acid t-butyl ester (4.4 g, 12.4 mmol) in anhydrous THF (70 mL) was added a solution of 1 M LiHMDS in THF (28 mL) over 15 minutes at −65° C. under nitrogen. After stirring for 3 hours at −65° C., oxodiperoxymolybdenum(pyridine) (hexamethylphosphorictriamide) (9 g, 18.6 mmol) was added. The mixture was stirred for another 2 hours at −35° C., then saturated aqueous Na₂S₂O₃ (60 mL) was added. The organic layer was collected and washed with saturated aqueous NH₄Cl (60 mL×3) and saturated aqueous NaCl (60 mL×2), then dried over Na₂SO₄, and the solvent was removed under reduced pressure to yield the crude product which was further purified by chromatography (hexanes:EtOAc=5:1) to yield Compound 1 as a white solid (1.8 g). LC-MS: 757 [2M+Na].

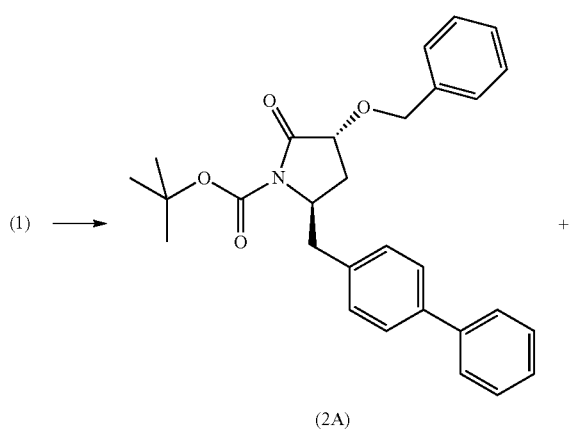

(1) →

(2A)

+

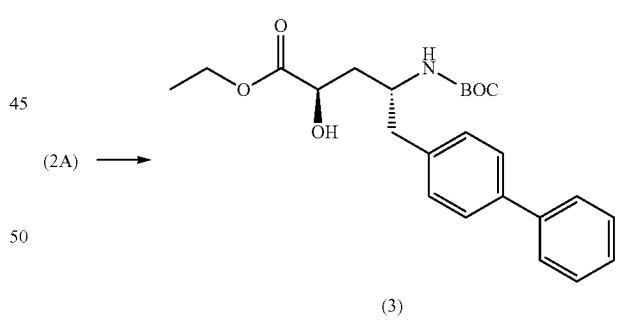

(2B)

To a solution of Compound 1 (1.8 g, 5.0 mmol) in anhydrous DCM (50 mL) was added DMAP (122 mg, 1 mmol) and Et₃N (1.5 g, 14.9 mmol) at 0° C. under nitrogen. After stirring for 0.5 hour at 0° C., benzyl chloride (1.0 g, 7.4 mmol) was added over 15 minutes. The mixture was stirred for an additional 2 hours at 0° C., then saturated aqueous NaHCO₃ (50 mL) was added. The organic layer was collected and washed with saturated aqueous NaHCO₃ (50 mL×2) and saturated aqueous NaCl (50 mL×1), then dried over Na₂SO₄. The solids were filtered out and the filtrate was concentrated to yield the crude product which was further purified by chromatography (hexanes:EtOAc=4:1) to yield Compound 2A (471 mg) and Compound 2B (883 mg) as white solids. LC-MS: 494 [M+Na]; 965 [2M+Na].

Compound 2A: ¹H NMR (300 MHz, CDCl₃): δ(ppm)=8.02 (m, 2H), 7.57-7.25 (m, 12H), 5.42 (m, 1H), 4.50 (m, 1H), 3.26-3.21 (m, 1H), 2.90 (m, 1H), 2.58 (m, 1H), 2.15-2.05 (m, 1H), 1.62 (m, 9H)

Compound 2B: ¹H NMR (300 MHz, CDCl₃): δ(ppm)=8.06 (m, 2H), 7.58-7.18 (m, 12H), 5.53-5.41 (m, 1H), 4.39 (m, 1H), 3.57-3.54 (m, 1H), 2.87-2.80 (m, 1H), 2.48-2.44 (m, 1H), 1.98 (m, 1H), 1.63 (m, 9H).

(2A) →

(3)

To a stirred solution of Compound 2A (471 mg, 1 mmol) in anhydrous EtOH (10 mL) was added anhydrous K₂CO₃ (691 mg, 5 mmol) at room temperature under nitrogen. After stirring for 20 hours at room temperature, the solids were filtered out. To the filtrate was added water (30 mL), DCM (30 mL) and saturated aqueous NaCl (5 mL). The aqueous layer was separated and extracted with DCM (30 mL×3). The combined organic layers were washed with saturated aqueous NaCl (50 mL), dried over Na₂SO₄, and concentrated to yield the crude product which was further purified by chromatography (hexanes:EtOAc=6:1) to yield Compound 3 as a white solid (275 mg). LC-MS: 436 [M+Na], 849 [2M+Na].

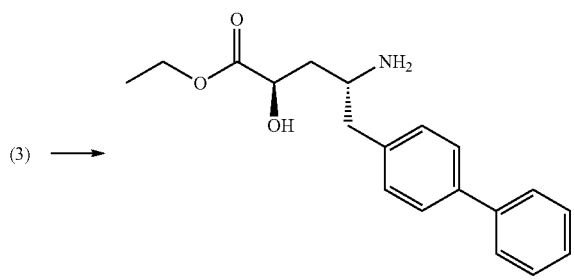 [SMILES: CCOC(=O)[C@H](O)C[C@H](N)Cc1ccc(-c2ccccc2)cc1]

(3) →

To EtOH (5 mL) was added acetyl chloride (685 mg) at −30° C. After stirring for 1 hour at −30° C., a solution of compound 3 (275 mg, 665 μmol) in anhydrous EtOH (5 mL) was added. The mixture was heated to 25° C. and stirred for 3 hours at 25° C. After evaporation of the solvent, the residue was washed with cold anhydrous Et$_2$O (10 mL) to yield the title compound as a white solid HCl salt (207 mg). LC-MS: 314 [M+H], 649 [2M+Na].

$^1$H NMR (300 MHz, CDCl$_3$): δ(ppm)=7.99 (m, 3H), 7.66-7.64 (m, 4H), 7.48-7.35 (m, 5H), 6.08 (m, 1H), 4.21 (m, 1H), 4.09-4.05 (m, 2H), 3.52 (m, 1H), 2.97-2.95 (m, 2H), 1.89-1.87 (m, 2H), 1.19-1.14 (m, 3H).

Preparation 21: (2R,4R)-4-Amino-5-(5'-chloro-2'-fluorobiphenyl-4-yl)-2-hydroxypentanoic acid 5-methyl-2-oxo-[1,3]dioxol-4-ylmethyl Ester

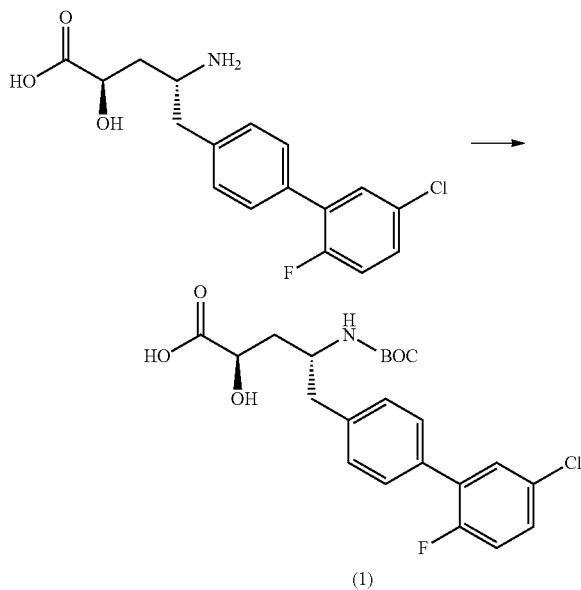

To a suspension of (2R,4R)-4-amino-5-(5'-chloro-2'-fluorobiphenyl-4-yl)-2-hydroxypentanoic acid (HCl salt; 10.3 g, 27.6 mmol) in THF (45 mL) was added aqueous NaOH (3.3 g, 82.8 mmol). A solution of (BOC)$_2$O (9.6 g, 44.2 mmol) in THF (25 mL) was added dropwise at 0° C. The resulting mixture was stirred at room temperature for 16 hours. The THF was removed and the residue was dissolved in water (50 mL). The solution was acidified to pH=3 with aqueous HCl (2N). The resulting precipitate was filtered off, and the cake was washed with water (20 mL) and purification by chromatography (DCM:MeOH=20:1) to yield Compound 1 as a white solid (9.0 g). LC-MS: 438 [M+H]$^+$.

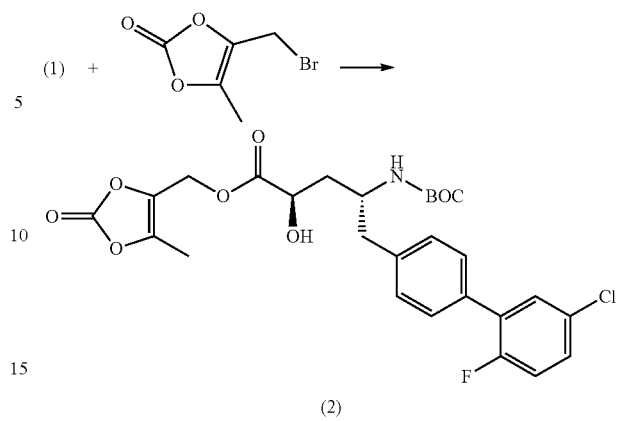

To a solution of Compound 1 (2 g, 4.6 mmol) and 4-(bromomethyl)-5-methyl-1,3-dioxol-2-one (880 mg, 4.6 mmol) in DMF (20 mL) was added K$_2$CO$_3$ (947 mg, 6.8 mmol) and KI (152 mg, 0.9 mmol). After stirring at room temperature for 2 hours, the mixture was diluted with water (50 mL) and extracted with EtOAc (2×100 mL). The combined organic layers were washed with saturated aqueous NaCl (2×100 mL), dried over anhydrous Na$_2$SO$_4$, filtered, and concentrated. The residue was purified by chromatography (DCM:EtOAc=10:1) to yield Compound 2 as a yellow foam (2.3 g). LC-MS: 572 [M+Na]$^+$.

(2) →

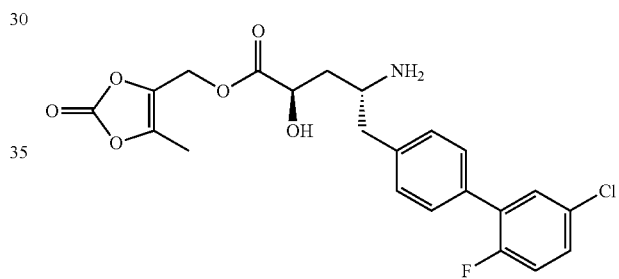

A solution of Compound 2 (2.3 g, 4.2 mmol) in HCl/dioxane (50 mL, 3.3 M) was stirred at room temperature for 2 hours. The solvent was removed, and the residue was washed with EtOAc (10 mL) to yield the title compound as a white solid (1.8 g). LC-MS: 450.0 [M+H]. $^1$H NMR (DMSO-d$_6$, 400 MHz) δ 1.85-1.92 (m, 2H), 2.17 (s, 3H), 2.99 (br, 2H), 3.57 (br, 1H), 4.26-4.42 (m, 1H), 5.02 (s, 2H), 6.19 (d, J=5.0 Hz, 1H), 7.34-7.45 (m, 3H), 7.49-7.51 (m, 1H), 7.53-7.68 (m, 3H), 7.99 (s, 3H).

Preparation 22: (2R,4R)-4-Amino-5-(5'-chloro-2'-fluorobiphenyl-4-yl)-2-hydroxypentanoic acid 2,2,3,3,3-pentafluoropropyl Ester

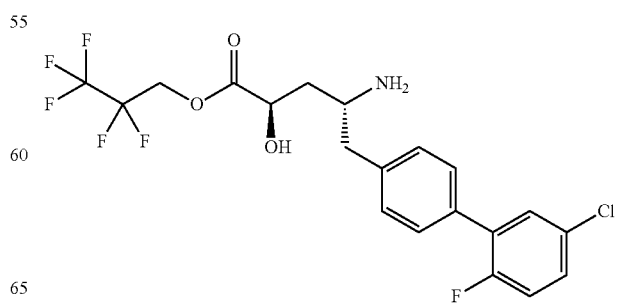

Using the procedures described herein, the title compound can also be prepared.

Preparation 23: (2R,4R)-4-Amino-5-(5'-chloro-2'-fluorobiphenyl-4-yl)-2-hydroxypentanoic Acid Butyryloxymethyl Ester

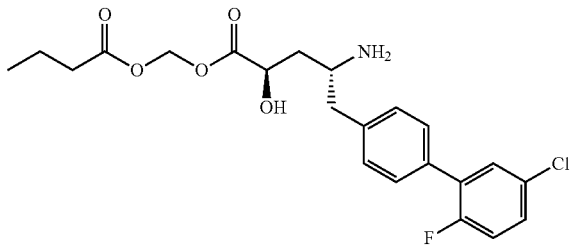 [SMILES: CCCC(=O)OCOC(=O)[C@H](O)C[C@H](N)Cc1ccc(-c2cc(Cl)ccc2F)cc1]

Using the procedures described herein, the title compound can also be prepared.

Example 1A: (2R,4R)-5-(3'-Chlorobiphenyl-4-Yl)-2-Hydroxy-4-[(3-Hydroxy-3H-benzotriazole-5-carbonyl)amino]pentanoic Acid

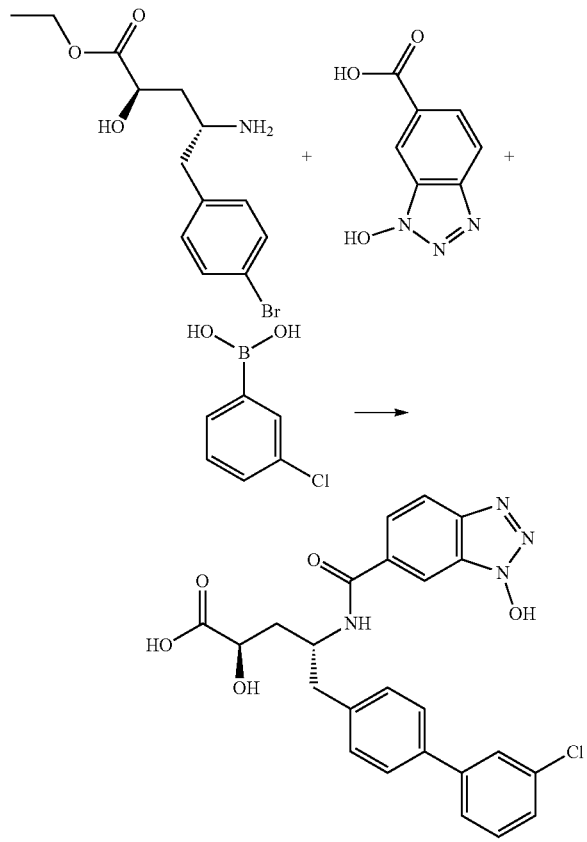

1-Hydroxy-1H-1,2,3-benzotriazole-6-carboxylic acid (56.6 mg, 316 μmol) and HCTU (131 mg, 316 μmol) were combined in DMF, and stirred for 5 minutes at room temperature. DIPEA (83 μL, 474 μmol) and (2R,4R)-4-amino-5-(4-bromophenyl)-2-hydroxypentanoic acid ethyl ester (50 mg, 0.2 mmol) were added, and the resulting mixture was stirred for 10 minutes. The mixture was evaporated under reduced pressure and purified (C18 column. 20-70% MeCN in water with 5% TFA). The clean fractions were lyophilized (40 mg). These solids were then combined with 3-chlorophenylboronic acid (44.5 mg, 285 μmol), $K_2CO_3$ (66 mg, 474 μmol), EtOH (0.8 mL, 10 mmol), and water (0.2 mL, 10 mmol). SilicaCat® DPP-Pd (0.28 mmol/g loading; 57 mg, 16 μmol) was added, and the resulting mixture was microwaved at 100° C. for 10 minutes. The mixture was filtered and 1 M LiOH in water (1.3 mL, 1.3 mmol) was added. The mixture was stirred for 30 minutes, evaporated under reduced pressure, and purified by preparative HPLC to yield the title compound (20.2 mg, purity 95%). MS m/z [M+H]$^+$ calc'd for $C_{24}H_{21}ClN_4O_5$, 481.12; found 481.2.

Example 1B: (2R,4R)-5-(3'-Chlorobiphenyl-4-yl)-2-hydroxy-4-[(3-hydroxy-3H-benzotriazole-5-carbonyl)amino]pentanoic Acid 3,3,3-Trifluoropropyl Ester

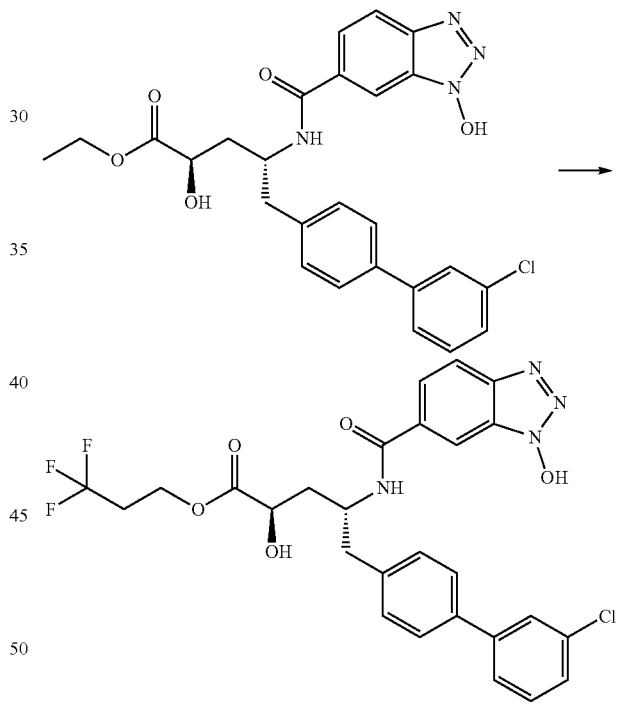

4.0 M HCl in 1,4-dioxane (196 μL, 786 μmol) was added to a solution of (2R,4R)-5-(3'-chlorobiphenyl-4-yl)-2-hydroxy-4-[(3-hydroxy-3H-benzotriazole-5-carbonyl)amino]pentanoic acid ethyl ester (50.0 mg, 98.2 μmol) in 3,3,3-trifluoropropan-1-ol (336 mg, 3.0 mmol), and the resulting mixture was stirred at 70° C. for 3 hours. The mixture was concentrated in vacuo to yield a white solid, which was purified by preparative HPLC (C18 column chromatography using 40-90% MeCN in water with 0.05% TFA) to yield the title compound as a white solid (18 mg, purity 100%). MS m/z [M+H]$^+$ calc'd for $C_{27}H_{24}ClF_3N_4O_5$, 577.14; found 577.1.

Example 1C: (2R,4R)-5-(3'-Chlorobiphenyl-4-yl)-2-hydroxy-4-[(3-hydroxy-3H-benzotriazole-5-carbonyl)amino]pentanoic Acid 2,2,2-Trifluoroethyl Ester

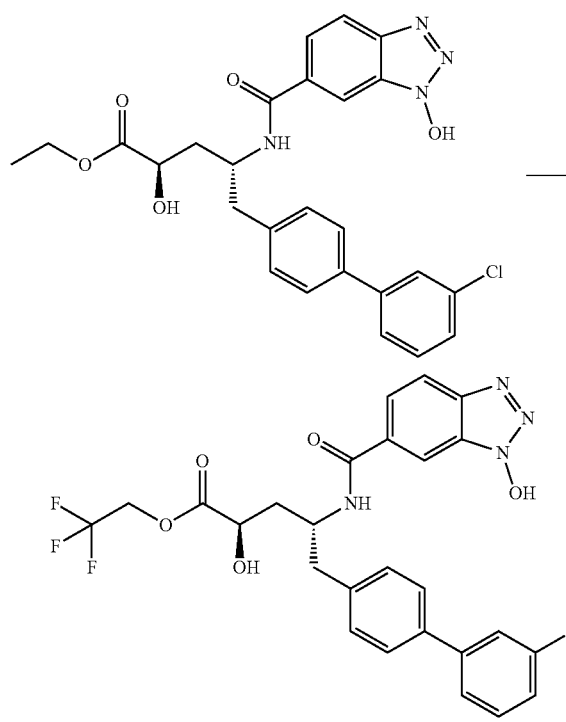

4.0 M HCl in 1,4-dioxane (196 µL, 786 µmol) was added to a solution of (2R,4R)-5-(3'-chlorobiphenyl-4-yl)-2-hydroxy-4-[(3-hydroxy-3H-benzotriazole-5-carbonyl)amino]pentanoic acid ethyl ester (50.0 mg, 98.2 µmol) in 2,2,2-trifluoroethanol (215 µL, 3.0 mmol), and the resulting mixture was stirred at 100° C. for 3 hours. The mixture was concentrated in vacuo to yield a clear colorless liquid, which was purified by preparative HPLC (C18 column chromatography using 40-90% MeCN in water with 0.05% TFA) to yield the title compound as a white solid (15.2 mg, purity 99%). MS m/z [M+H]$^+$ calc'd for $C_{26}H_{22}ClF_3N_4O_5$, 563.12; found 563.2.

Example 1D: (2R,4R)-5-(3'-Chlorobiphenyl-4-yl)-2-hydroxy-4-[(3-hydroxy-3H-benzotriazole-5-carbonyl)amino]pentanoic Acid 2,2,3,3,3-Pentafluoropropyl Ester

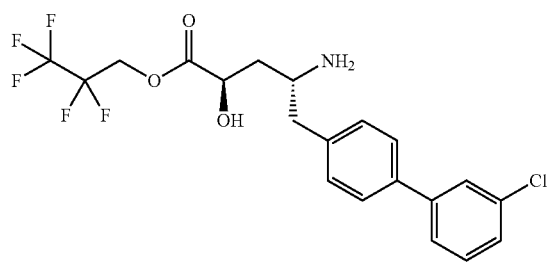

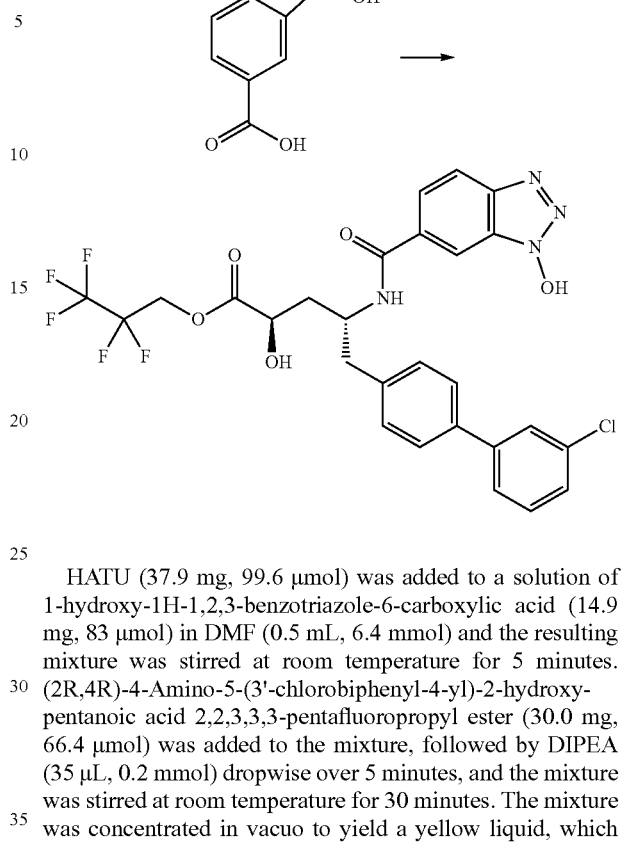

HATU (37.9 mg, 99.6 µmol) was added to a solution of 1-hydroxy-1H-1,2,3-benzotriazole-6-carboxylic acid (14.9 mg, 83 µmol) in DMF (0.5 mL, 6.4 mmol) and the resulting mixture was stirred at room temperature for 5 minutes. (2R,4R)-4-Amino-5-(3'-chlorobiphenyl-4-yl)-2-hydroxypentanoic acid 2,2,3,3,3-pentafluoropropyl ester (30.0 mg, 66.4 µmol) was added to the mixture, followed by DIPEA (35 µL, 0.2 mmol) dropwise over 5 minutes, and the mixture was stirred at room temperature for 30 minutes. The mixture was concentrated in vacuo to yield a yellow liquid, which was purified by preparative HPLC to yield the title compound as a white solid (2.9 mg, purity 100%). MS m/z [M+H]$^+$ calc'd for $C_{27}H_{22}ClF_5N_4O_5$, 613.12; found 613.0.

Example 1E: (2R,4R)-5-(3'-Chlorobiphenyl-4-yl)-2-hydroxy-4-[(3-hydroxy-3H-benzotriazole-5-carbonyl)amino]pentanoic Acid 5-Methyl-2-oxo-[1,3]dioxol-4-ylmethyl Ester

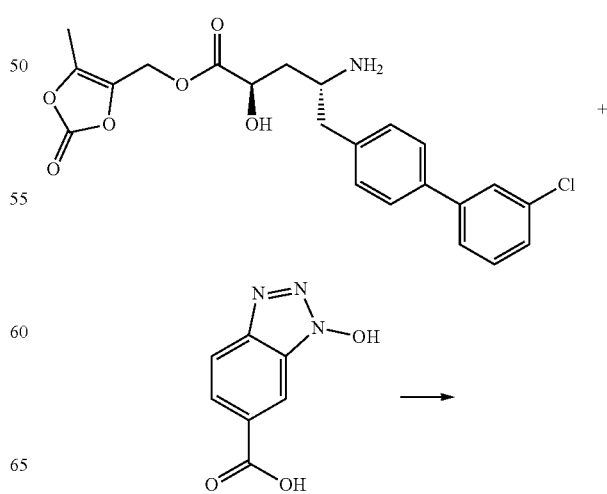

-continued

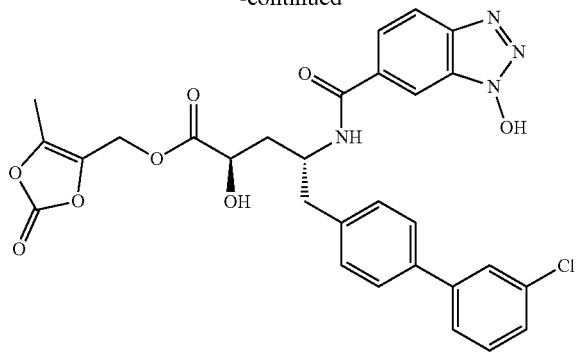

HATU (37.9 mg, 99.6 µmol) was added to a solution of 1-hydroxy-1H-1,2,3-benzotriazole-6-carboxylic acid (14.9 mg, 83 µmol) in DMF (0.5 mL, 6.4 mmol) and the resulting mixture was stirred at room temperature for 5 minutes. (2R,4R)-4-Amino-5-(3'-chlorobiphenyl-4-yl)-2-hydroxypentanoic acid 5-methyl-2-oxo[1,3]dioxol-4-ylmethyl ester (28.7 mg, 66.4 µmol) was added to the mixture, followed by DIPEA (35 µL, 0.2 mmol) dropwise over 5 minutes, and the mixture was stirred at room temperature for 30 minutes. The mixture was concentrated in vacuo to yield a yellow liquid, which was purified by preparative HPLC to yield the title compound as a white solid (37.8 mg, purity 98.5%). MS m/z [M+H]+ calc'd for $C_{29}H_{25}ClN_4O_8$, 593.14; found 593.0.

Example 1F: (2R,4R)-5-(3'-Chlorobiphenyl-4-yl)-2-hydroxy-4-[(3-hydroxy-3H-benzotriazole-5-carbonyl)amino]pentanoic Acid Butyryloxymethyl Ester

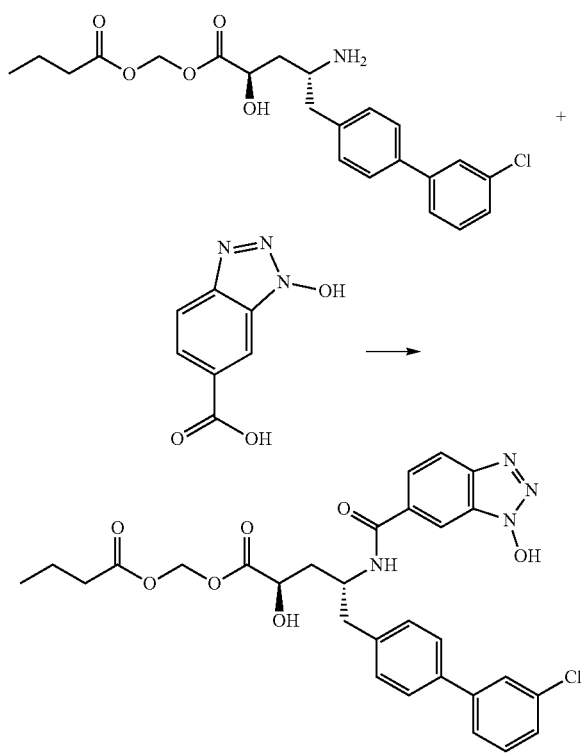

HATU (37.9 mg, 99.6 µmol) was added to a solution of 1-hydroxy-1H-1,2,3-benzotriazole-6-carboxylic acid (14.9 mg, 83 µmol) in DMF (0.5 mL, 6.4 mmol) and the resulting mixture was stirred at room temperature for 5 minutes. (2R,4R)-4-Amino-5-(3'-chlorobiphenyl-4-yl)-2-hydroxypentanoic acid butyryloxymethyl ester (27.9 mg, 66.4 µmol) was added to the mixture, followed by DIPEA (35 µL, 0.2 mmol) dropwise over 5 minutes, and the mixture was stirred at room temperature for 30 minutes. The mixture was concentrated in vacuo to yield a yellow liquid, which was purified by preparative HPLC to yield the title compound as a white solid (5.2 mg, purity 98.2%). MS m/z [M+H]+ calc'd for $C_{29}H_{29}ClN_4O_7$, 581.17; found 581.2.

Example 1G: (2R,4R)-4-[(3-Acetoxymethoxy-3H-benzotriazole-5-carbonyl)amino]-5-(3'-chlorobiphenyl-4-yl)-2-hydroxypentanoic Acid

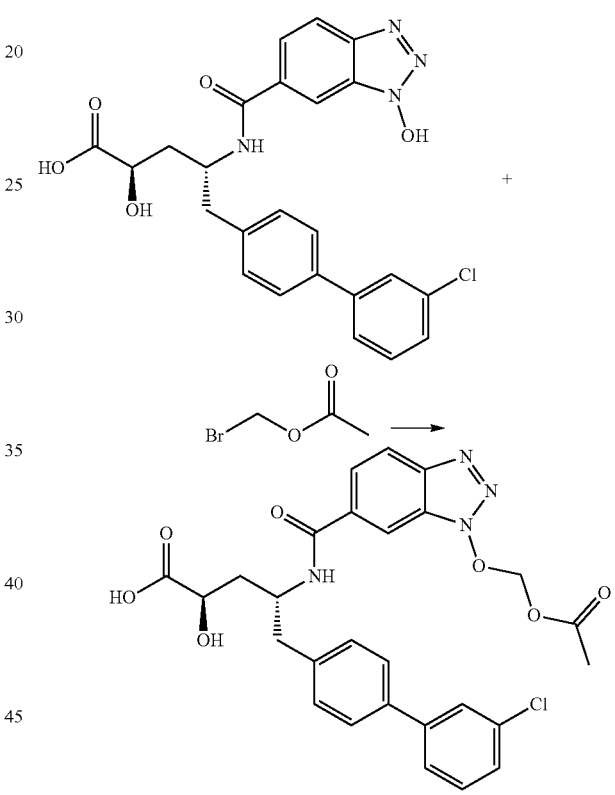

4.0 M HCl in 1,4-dioxane (270 mL, 1.1 mmol) was added to a solution of (2R,4R)-5-(3'-chlorobiphenyl-4-yl)-2-hydroxy-4-[(3-hydroxy-3H-benzotriazole-5-carbonyl)amino] pentanoic acid (130 mg, 270 µmol) in benzyl alcohol (559 µL, 5.4 mmol), and stirred at 60° C. for 1.5 hours. The mixture was then purified (C18 column chromatography, 55 g column, using 30-90% MeCN in water with 0.05% TFA) to yield an off-white solid. Bromomethyl acetate (45.5 mg, 297 µmol) was added to a solution of this off-white solid and $K_2CO_3$ (82.2 mg, 595 µmol) in DMF (3.1 mL, 40.0 mmol) and the resulting mixture was stirred at room temperature for 1 hour. The mixture was then purified (column chromatography, small column, using 40-90% MeCN in water with 0.05% TFA) to yield a clear colorless viscous liquid. 10% Pd/C, 50% wet (0.45 mmol/g loading; 30.0 mg, 13.5 µmol) was added to a solution of this clear colorless viscous liquid in MeOH (4.1 mL, 102 mmol) and the resulting mixture was stirred under hydrogen for 30 minutes. The mixture was filtered and the filtrate was concentrated in vacuo to yield a clear colorless liquid. The crude liquid was purified (C18 column chromatography, 55 g column, using 30-85% MeCN in water with 0.05% TFA) to yield the title compound (14.0 mg) as a white solid. MS m/z [M+H]+ calc'd for $C_{27}H_{25}ClN_4O_7$, 553.14; found 553.1.

Example 1H: (2R,4R)-4-[(3-Acetoxymethoxy-3H-benzotriazole-5-carbonyl)amino]-5-(3'-chlorobiphenyl-4-yl)-2-hydroxypentanoic Acid Acetoxymethyl Ester

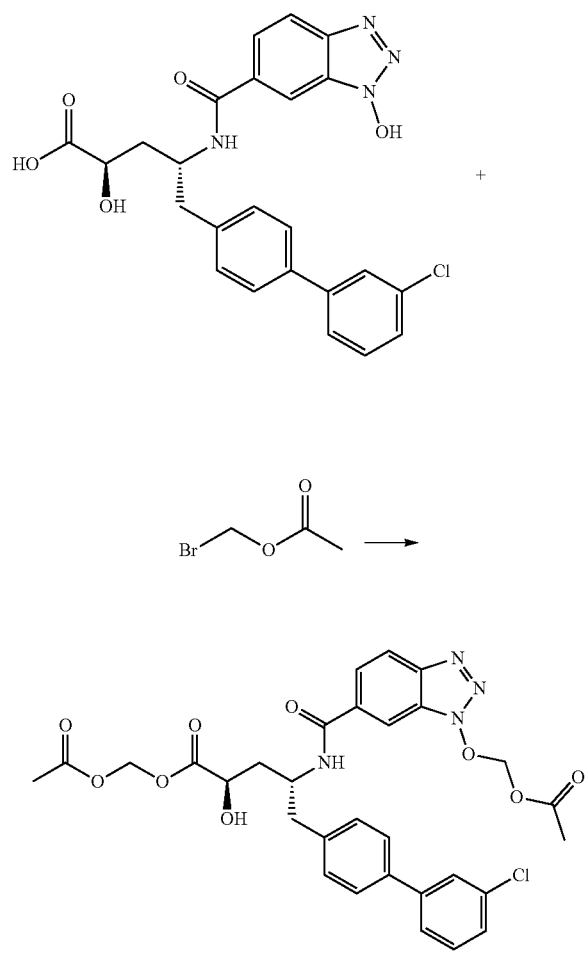

Et$_3$N (7.0 μL, 50 μmol) was added to a solution of [(2R,4R)-5-(3'-chlorobiphenyl-4-yl)-2-hydroxy-4-[(3-hydroxy-3H-benzotriazole-5-carbonyl)amino]pentanoic acid (20.0 mg, 42 μmol) and bromomethyl acetate (6.52 μL, 67 μmol) in acetone (1.3 mL, 17.2 mmol), and the resulting mixture was stirred in a sealed vial at 65° C. for 5 hours. 1:1 TFA/DCM (0.50 mL, 3.1 mmol) was added, and the mixture was stirred at room temperature for 30 minutes and concentrated to yield a clear yellow liquid. The crude liquid was purified by preparative HPLC (C18 column chromatography, small column, using 30-90% MeCN in water with 0.05% TFA) to yield the title compound (5.2 mg, purity 100%). MS m/z [M+H]+ calc'd for $C_{30}H_{29}ClN_4O_9$, 625.16; found 625.1.

Example 1I (2R,4R)-4-[(3-Benzyloxy-3H-benzotriazole-5-carbonyl)amino]-5-(3'-chlorobiphenyl-4-yl)-2-hydroxypentanoic Acid

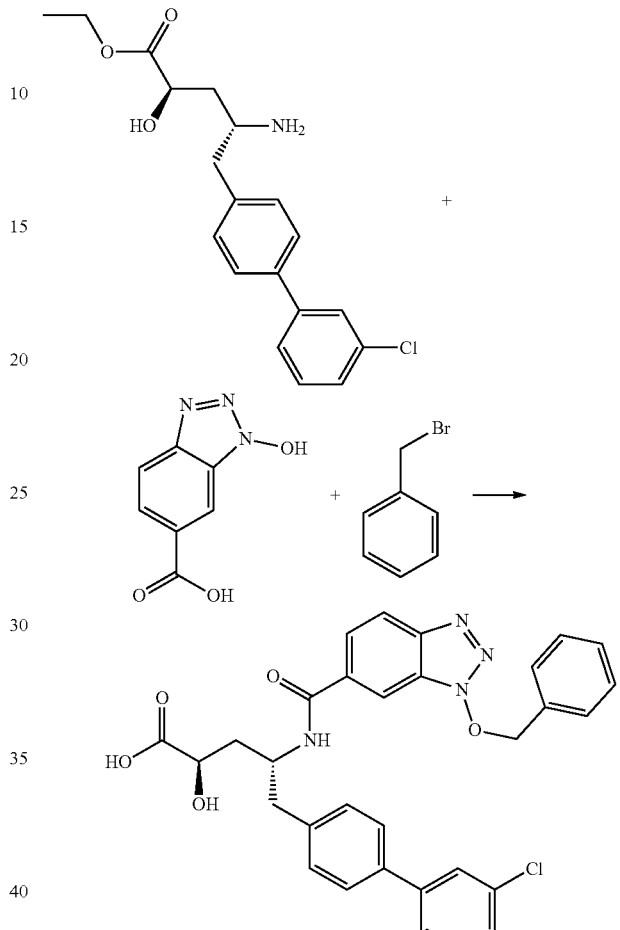

HATU (246 mg, 647 μmol) was added to a solution of 1-hydroxy-1H-1,2,3-benzotriazole-6-carboxylic acid (116 mg, 647 μmol) in DMF (2.0 mL, 25.8 mmol) and the resulting mixture was stirred at room temperature for 10 minutes. DIPEA (225 μL, 1.3 mmol) was added to the mixture, followed by (2R,4R)-4-amino-5-(3'-chlorobiphenyl-4-yl)-2-hydroxypentanoic acid ethyl ester (150 mg, 431 μmol) and the mixture was stirred at room temperature for 1 hour. 3.0 M LiOH in water (1.7 mL, 5.2 mmol) was added to the mixture and stirred at room temperature for 30 minutes. The mixture was then purified (C18 column chromatography, 55 g column, using 40-90% MeCN in water with 0.05% TFA) to yield a white solid. Benzyl bromide (41 μL, 345 μmol) was added to a solution of this solid in acetone (3.0 mL, 40.8 mmol). Et$_3$N (54 μL, 388 μmol) was added and the resulting mixture was stirred at 50° C. for 2 hours. The mixture was concentrated in vacuo and the resulting crude clear yellow liquid was purified (C18 column chromatography, 55 g column, using 40-90% MeCN in water with 0.05% TFA) to yield the title compound (201 mg, purity 100%) as a white solid. MS m/z [M+H]+ calc'd for $C_{31}H_{27}ClN_4O_5$, 571.17; found 571.

Example 1J: (2R,4R)-5-(3'-Chlorobiphenyl-4-yl)-2-hydroxy-4-[(3-hydroxy-3H-benzotriazole-5-carbonyl)amino]pentanoic Acid Benzyl Ester

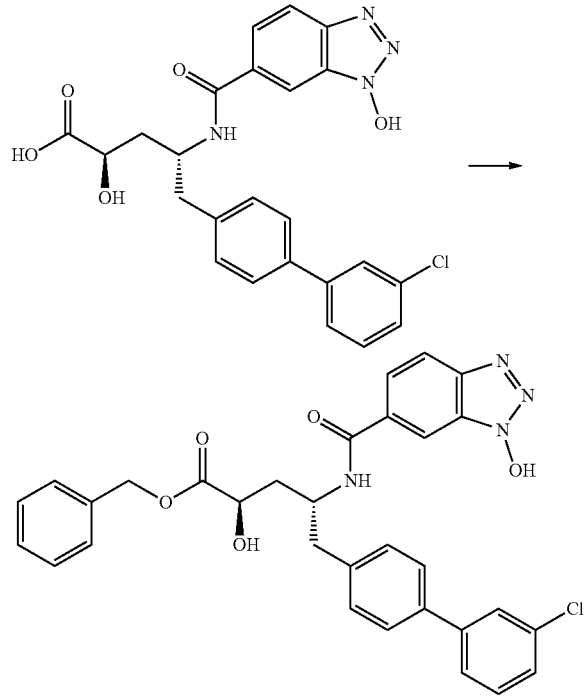

4.0 M HCl in 1,4-dioxane (270 μL, 1.0 mmol) was added to a solution of (2R,4R)-5-(3'-chlorobiphenyl-4-yl)-2-hydroxy-4-[(3-hydroxy-3H-benzotriazole-5-carbonyl)amino]pentanoic acid (130 mg, 270 μmol) in benzyl alcohol (559 μL, 5.4 mmol), and the resulting mixture was stirred at 60° C. for 15 minutes. The mixture was purified by preparative HPLC (C18 column chromatography using 30-90% MeCN in water with 0.05% TFA) to yield the title compound as an off-white solid (16.0 mg, purity 99.2%). MS m/z [M+H]+ calc'd for $C_{31}H_{27}ClN_4O_5$, 571.17; found 571.1.

Example 1K: (2R,4R)-5-(3'-Chlorobiphenyl-4-yl)-2-hydroxy-4-[(3-hydroxy-3H-benzotriazole-5-carbonyl)amino]pentanoic Acid Acetoxymethyl Ester

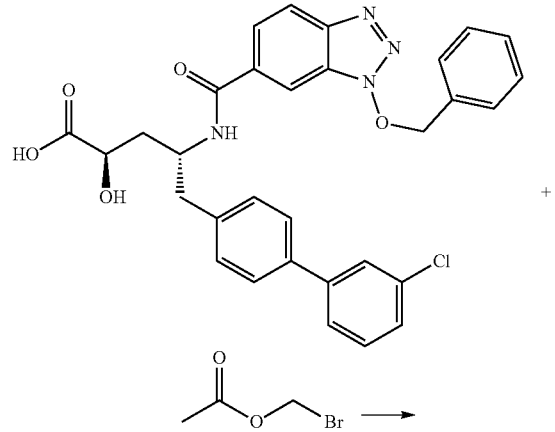

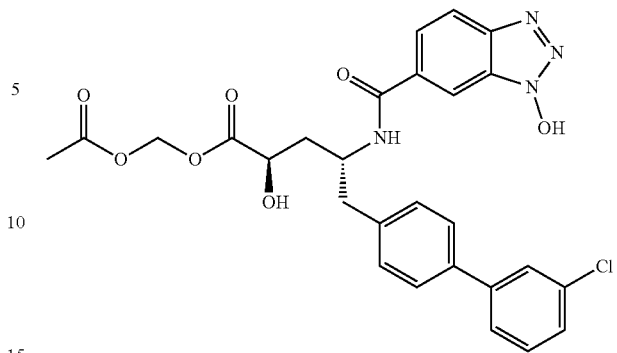

Bromomethyl acetate (6.7 μL, 68.3 μmol) and Et₂O (11.7 μL, 84 μmol) were added to a solution of (2R,4R)-4-[(3-benzyloxy-3H-benzotriazole-5-carbonyl)amino]-5-(3'-chlorobiphenyl-4-yl)-2-hydroxypentanoic acid (30.0 mg, 52.5 μmol) in acetone (1.0 mL, 13.6 mmol) and the resulting mixture was stirred at 45° C. for 1 hour. A drop of AcOH was added to neutralize the reaction and the mixture was concentrated to yield a clear yellow liquid. The crude liquid was purified (C18 column chromatography, 55 g column, using 40-90% MeCN in water with 0.05% TFA) to yield a white solid. The solid was dissolved in THF (1.0 mL, 12.3 mmol) and 10% Pd/C, 50% wet (0.45 mmol/g loading; 5.8 mg, 2.6 μmol) was added to the solution, which was stirred under hydrogen for 1 hour. The mixture was filtered and the filtrate was concentrated to yield a clear colorless liquid. The crude liquid was purified (preparative scale C18 column chromatography, small column, using 30-90% MeCN in water with 0.05% TFA) to yield the title compound as a white solid (10.0 mg, purity 99%). MS m/z [M+H]+ calc'd for $C_{27}H_{25}ClN_4O_7$, 553.14; found 553.1.

Example 1L: (2R,4R)-4-{[3-((R)-2-Amino-3-methylbutyryloxymethoxy)-3H-benzotriazole-5-carbonyl]amino}-5-(3'-chlorobiphenyl-4-yl)-2-hydroxy-pentanoic Acid

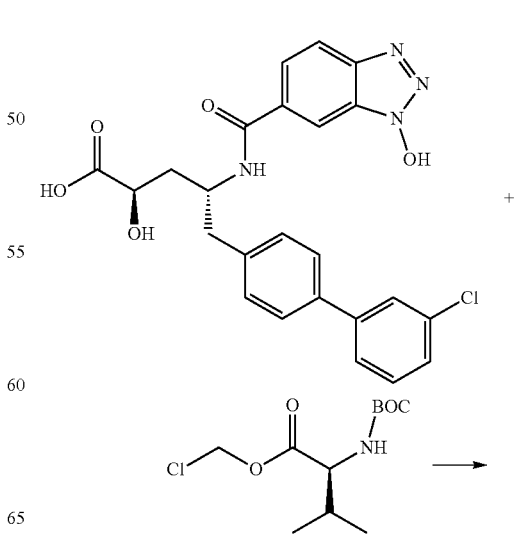

-continued

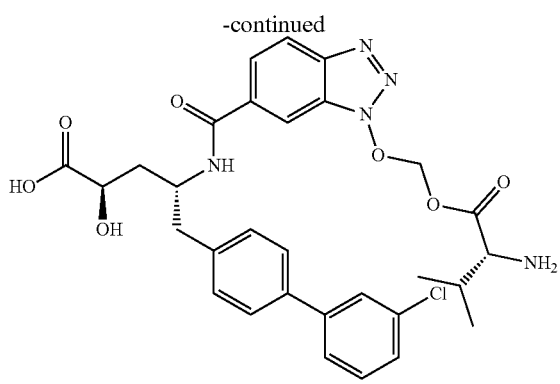

Et₃N (7.0 μL, 50 μmol) was added to a solution of [(2R,4R)-5-(3'-chlorobiphenyl-4-yl)-2-hydroxy-4-[(3-hydroxy-3H-benzotriazole-5-carbonyl)amino]pentanoic acid (20.0 mg, 42 μmol) and (S)-2-t-butoxycarbonylamino-3-methylbutyric acid chloromethyl ester (17.7 mg, 67 μmol) in acetone (1.3 mL, 17.2 mmol), and the resulting mixture was stirred in a sealed vial at 65° C. for 5 hours. 1:1 TFA/DCM (0.50 mL, 3.1 mmol) was added, and the mixture was stirred at room temperature for 30 minutes and concentrated to yield a clear yellow liquid. The crude liquid was purified by preparative HPLC (C18 column chromatography, small column, using 30-90% MeCN in water with 0.05% TFA) to yield the title compound as a white solid HCl salt (6.2 mg, purity 96%). MS m/z [M+H]⁺ calc'd for $C_{30}H_{32}ClN_5O_7$, 610.20; found 610.1.

Example 1M: (2R,4R)-4-[(3-Butyryloxymethoxy-3H-benzotriazole-5-carbonyl)amino]-5-(3'-chlorobiphenyl-4-yl)-2-hydroxypentanoic Acid

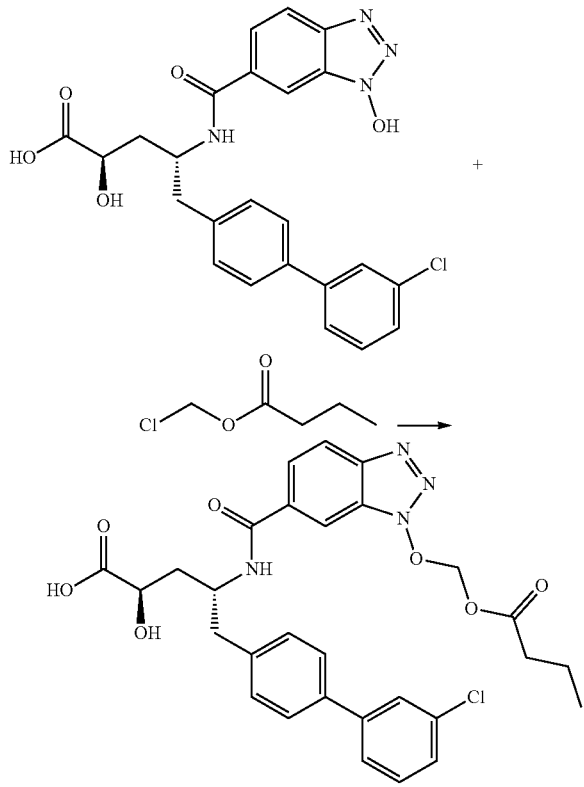

Et₃N (7.0 μL, 50 μmol) was added to a solution of [(2R,4R)-5-(3'-chlorobiphenyl-4-yl)-2-hydroxy-4-[(3-hydroxy-3H-benzotriazole-5-carbonyl)amino]pentanoic acid (20.0 mg, 42 μmol) and chloromethyl butyrate (8.3 μL, 67 μmol) in acetone (1.3 mL, 17.2 mmol), and the resulting mixture was stirred in a sealed vial at 65° C. for 5 hours. The mixture was then concentrated to yield a yellow liquid. The crude liquid was purified by preparative HPLC (C18 column chromatography, small column, using 30-90% MeCN in water with 0.05% TFA) to yield the title compound as a white solid (3.3 mg, purity 94%). MS m/z [M+H]⁺ calc'd for $C_{29}H_{29}ClN_4O_7$, 581.17; found 581.1.

Example 1N: (2R,4R)-5-(3'-Chlorobiphenyl-4-yl)-2-hydroxy-4-[(3-hydroxy-3H-benzotriazole-5-carbonyl)amino]pentanoic Acid (R)-2-Methoxycarbonylamino-3-methylbutyryloxymethyl Ester

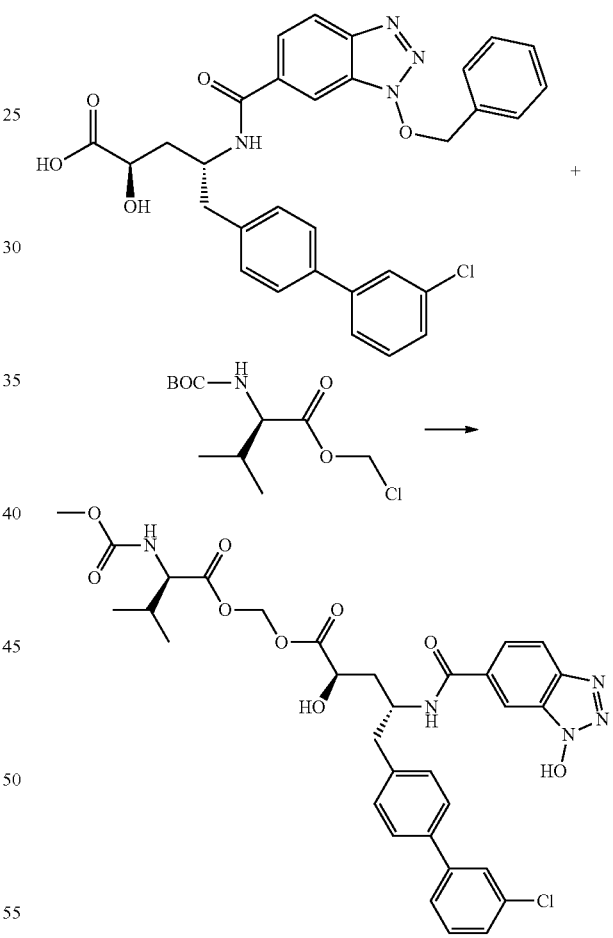

(S)-2-t-Butoxycarbonylamino-3-methyl-butyric acid chloromethyl ester (18.1 mg, 68.3 μmol) and Et₃N (11.7 μL, 84 μmol) were added to a solution of (2R,4R)-4-[(3-benzyloxy-3H-benzotriazole-5-carbonyl)amino]-5-(3'-chlorobiphenyl-4-yl)-2-hydroxypentanoic acid (30.0 mg, 52.5 μmol) in acetone (1.00 mL, 13.6 mmol) and stirred at 60° C. for 3 hours. The mixture was concentrated to yield a yellow liquid, which was combined with 1:1 TFA/DCM (1.0 mL, 6.2 mmol) and stirred at room temperature for 1 hour. The mixture was concentrated in vacuo and the resulting crude liquid was purified (C18 column chromatography, 55 g column, using 30-90% MeCN in water with 0.05% TFA) to yield a white solid. The solid was dissolved in DCM (0.5 mL, 7.8 mmol) at 0° C. Methyl chloroformate (6.1 μL, 78.8 μmol) was added followed by Et$_3$N (18.3 μL, 131 μmol) and the resulting mixture was stirred at room temperature for 30 minutes. A drop of AcOH was added to neutralize the reaction and the mixture was concentrated to yield a clear yellow liquid. The crude liquid was combined with 10% Pd/C, 50% wet (0.45 mmol/g loading; 5.8 mg, 2.6 μmol) and stirred under hydrogen for 1 hour. The mixture was filtered and the filtrate was concentrated to yield a clear yellow liquid. The crude liquid was purified (preparative scale C18 column chromatography, small column, using 30-90% MeCN in water with 0.05% TFA) to yield the title compound as a white solid TFA salt (7.5 mg, 99% purity,). MS m/z [M+H]$^+$ calc'd for $C_{32}H_{34}ClN_5O_9$, 668.20; found 668.1.

Example 1O: (2R,4R)-5-(3'-Chlorobiphenyl-4-yl)-2-hydroxy-4-{[3-((S)-2-methoxycarbonylamino-3-methylbutyryloxymethoxy)-3H-benzotriazole-5-carbonyl]amino}pentanoic Acid

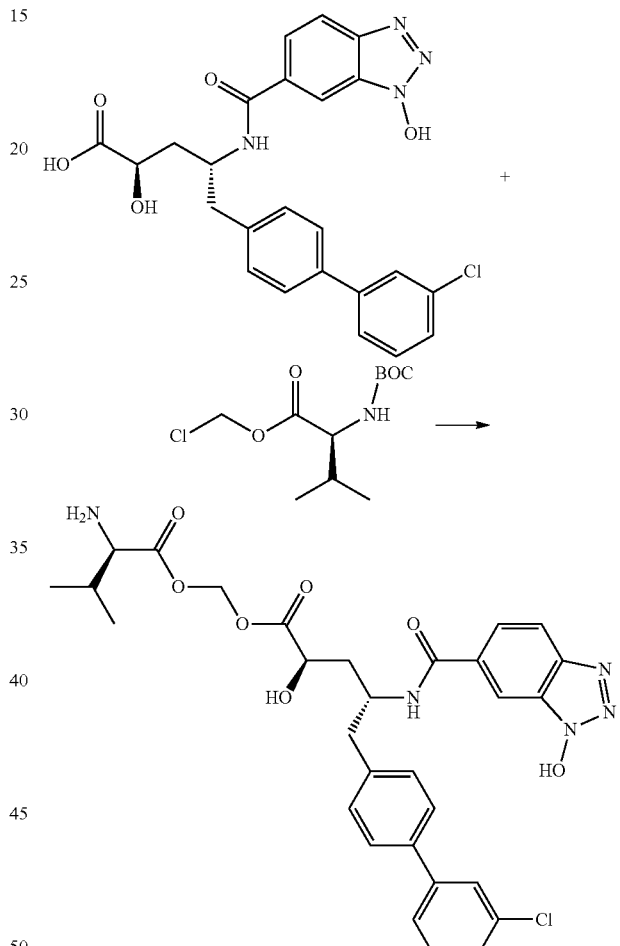

Et$_3$N (7.0 μL, 50 μmol) was added to a solution of [(2R,4R)-5-(3'-chlorobiphenyl-4-yl)-2-hydroxy-4-[(3-hydroxy-3H-benzotriazole-5-carbonyl)amino]pentanoic acid (20.0 mg, 42 μmol) and chloromethyl butyrate (8.3 μL, 67 μmol) in acetone (1.3 mL, 17.2 mmol), and the resulting mixture was stirred in a sealed vial at 65° C. for 5 hours. The mixture was then concentrated to yield a yellow liquid. The crude liquid was purified by preparative HPLC (C18 column chromatography, small column, using 30-90% MeCN in water with 0.05% TFA) to yield the title compound as a white solid (3.3 mg, purity 94%). MS m/z [M+H]$^+$ calc'd for $C_{29}H_{29}ClN_4O_7$, 581.17; found 581.1.

Example 1P: (2R,4R)-5-(3'-Chlorobiphenyl-4-yl)-2-hydroxy-4-[(3-hydroxy-3H-benzotriazole-5-carbonyl)amino]pentanoic Acid (R)-2-amino-3-methylbutyryloxymethyl Ester

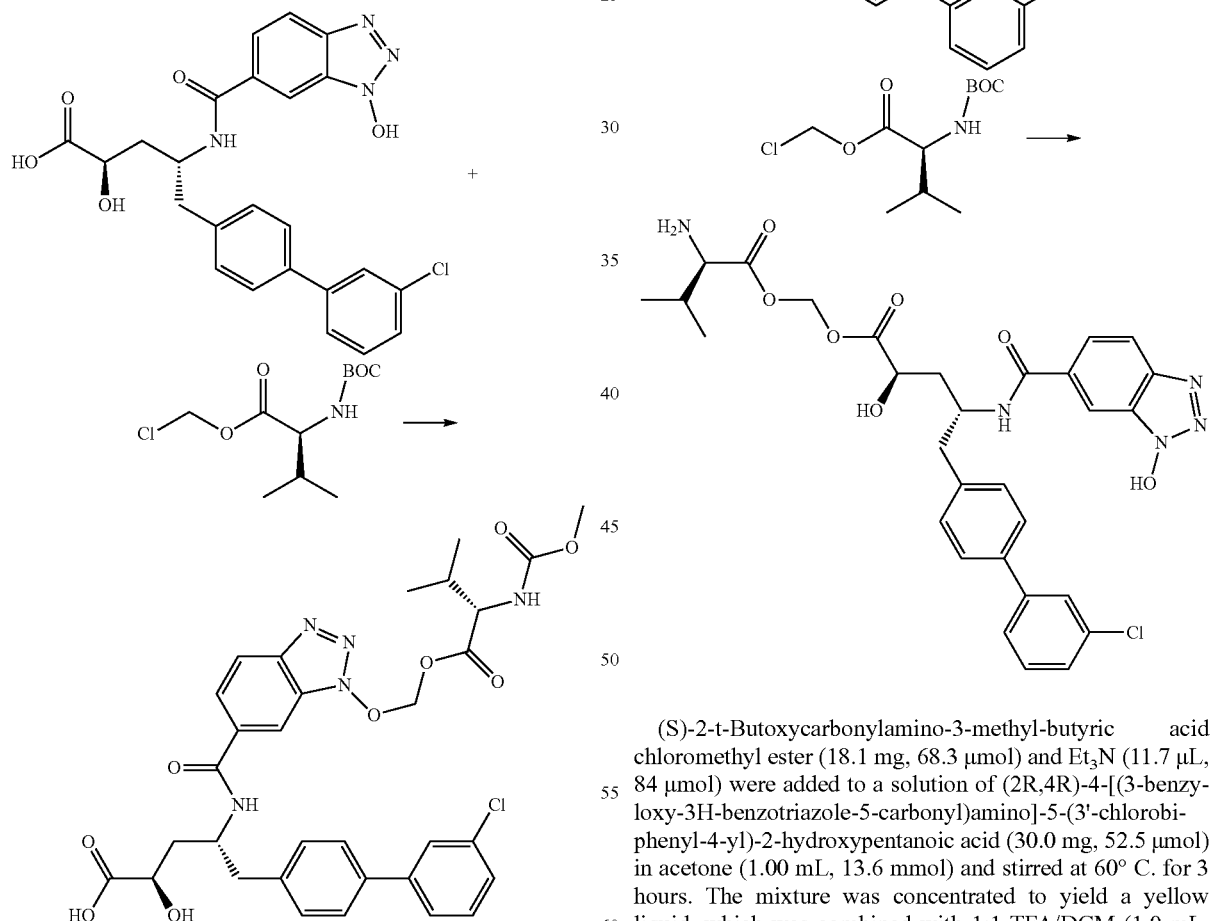

(S)-2-t-Butoxycarbonylamino-3-methyl-butyric acid chloromethyl ester (18.1 mg, 68.3 μmol) and Et$_3$N (11.7 μL, 84 μmol) were added to a solution of (2R,4R)-4-[(3-benzyloxy-3H-benzotriazole-5-carbonyl)amino]-5-(3'-chlorobiphenyl-4-yl)-2-hydroxypentanoic acid (30.0 mg, 52.5 μmol) in acetone (1.00 mL, 13.6 mmol) and stirred at 60° C. for 3 hours. The mixture was concentrated to yield a yellow liquid, which was combined with 1:1 TFA/DCM (1.0 mL, 6.2 mmol) and stirred at room temperature for 1 hour. The mixture was concentrated in vacuo and the resulting crude liquid was purified (C18 column chromatography, 55 g column, using 30-90% MeCN in water with 0.05% TFA) to yield a white solid. The solid was dissolved in THF (1.0 mL) and 10% Pd/C, 50% wet (0.45 mmol/g loading; 5.8 mg, 2.6 μmol) was added to the solution, which was stirred under hydrogen for 1 hour. The mixture was filtered and the filtrate was concentrated to yield a clear yellow liquid. The crude liquid was purified (preparative scale C18 column chromatography, small column, using 30-90% MeCN in water with 0.05% TFA) to yield the title compound as a white solid TFA salt (6.5 mg, purity 98%). MS m/z [M+H]$^+$ calc'd for $C_{30}H_{32}ClN_5O_7$, 610.20; found 610.1.

Example 2A: (2R,4R)-5-(3'-Chlorobiphenyl-4-yl)-2-hydroxy-4-[(5-hydroxy-1-methyl-1H-pyrazole-3-carbonyl)amino]pentanoic Acid

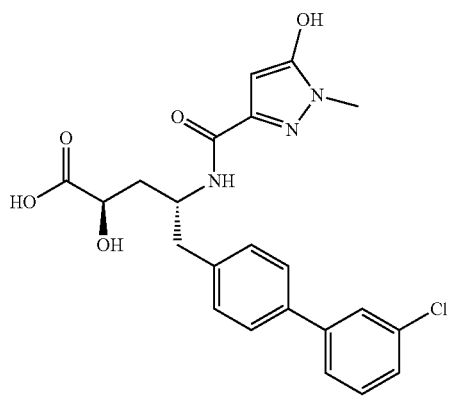 [SMILES: Cn1nc(C(=O)N[C@H](Cc2ccc(-c3cccc(Cl)c3)cc2)C[C@@H](O)C(=O)O)cc1O]

5-Hydroxy-1-methyl-1H-pyrazole-3-carboxylic acid (19.6 mg, 138 μmol) was combined with HCTU (56.9 mg, 138 μmol) in DMF. The mixture was stirred for 10 minutes at room temperature before adding DIPEA (72 μL, 413 μmol) and (2R,4R)-4-amino-5-(3'-chlorobiphenyl-4-yl)-2-hydroxypentanoic acid ethyl ester (50 mg, 0.1 mmol). The resulting mixture was stirred overnight at room temperature. EtOH (402 μL, 6.9 mmol) and 1 M LiOH in water (1.1 mL, 1.1 mmol) was added and the mixture was stirred at room temperature for 1 hour. The mixture was evaporated under reduced pressure and purified by preparative HPLC to yield the title compound (6.4 mg). MS m/z [M+H]$^+$ calc'd for $C_{22}H_{22}ClN_3O_5$, 444.12; found 444.4.

Example 2B: (2R,4R)-5-(3'-Chlorobiphenyl-4-yl)-2-hydroxy-4-[(5-hydroxy-1-methyl-1H-pyrazole-3-carbonyl)amino]pentanoic Acid 5-Methyl-2-oxo-[1,3]dioxol-4-ylmethyl Ester

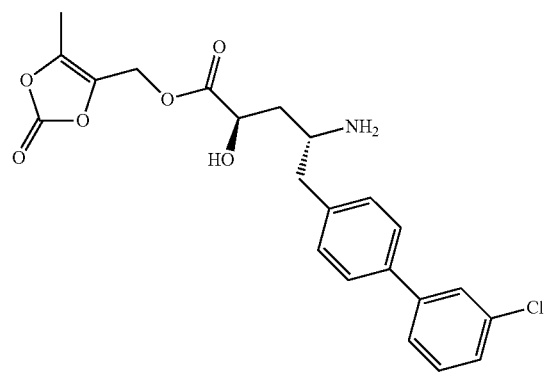

+

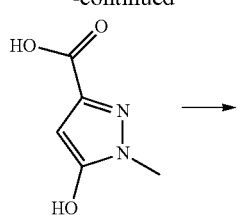

-continued

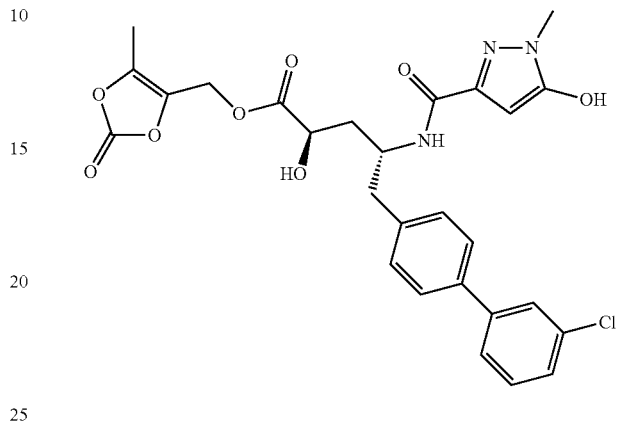

5-Hydroxy-1-methyl-1H-pyrazole-3-carboxylic acid (5.6 mg, 39 μmol) and HCTU (16.2 mg, 39 μmol) were combined in DMF (166 μL, 2.1 mmol) and stirred at room temperature for 15 minutes. DIPEA (19 μL, 0.1 mmol) and (2R,4R)-4-amino-5-(3'-chlorobiphenyl-4-yl)-2-hydroxypentanoic acid 5-methyl-2-oxo[1,3]dioxol-4-ylmethyl ester (15.4 mg, 36 μmol) were added, and the resulting mixture was stirred at room temperature for 30 minutes. The solvent was removed in vacuo and the crude product was purified by preparative HPLC to yield the title compound (7 mg). MS m/z [M+H]$^+$ calc'd for $C_{27}H_{26}ClN_3O_8$, 556.14; found 556.1.

Example 2C: (2R,4R)-5-(3'-Chlorobiphenyl-4-yl)-2-hydroxy-4-[(5-hydroxy-1-methyl-1H-pyrazole-3-carbonyl)amino]pentanoic Acid Ethyl Ester

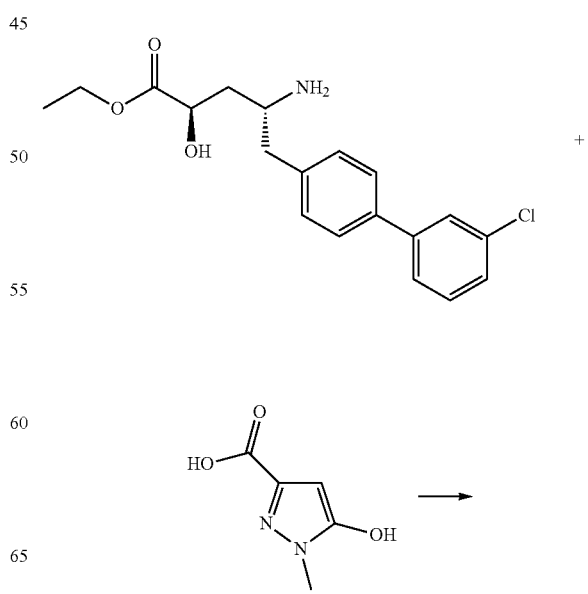

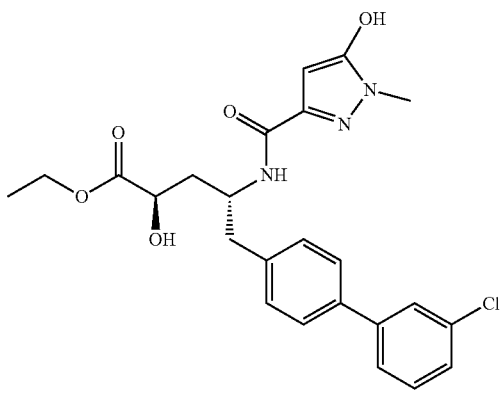

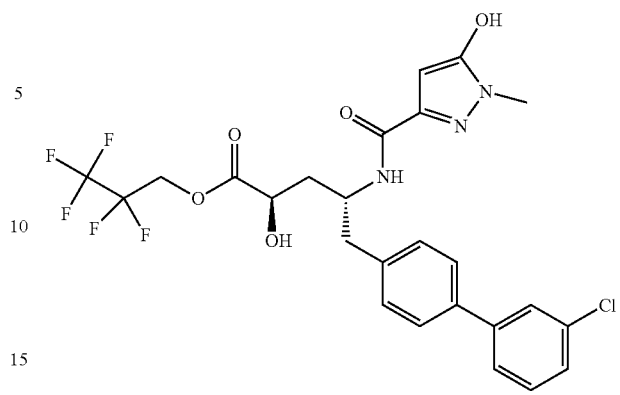

5-Hydroxy-1-methyl-1h-pyrazole-3-carboxylic acid (122 mg, 862 μmol) and HATU (361 mg, 949 μmol) were combined in DMF (1.0 mL, 13 mmol) and stirred for 10 minutes. (2R,4R)-4-amino-5-(3'-chlorobiphenyl-4-yl)-2-hydroxypentanoic acid ethyl ester (30.0 mg, 86 μmol) and DIPEA (165 μL, 949 μmol) were added, and the resulting mixture was stirred at room temperature overnight. The mixture was then concentrated under reduced pressure and the residue was dissolved in 50% AcOH-water (1.5 mL), filtered, purified by reverse phase preparative HPLC, and lyophilized to yield the title compound (11.1 mg). MS m/z [M+H]+ calc'd for $C_{24}H_{26}ClN_3O_5$, 472.16; found 472.2.

Example 2D: (2R,4R)-5-(3'-Chlorobiphenyl-4-yl)-2-hydroxy-4-[(5-hydroxy-1-methyl-1H-pyrazole-3-carbonyl)amino]pentanoic Acid 2,2,3,3,3-Pentafluoropropyl Ester (2R,4R)-5-(3'-Chlorobiphenyl-4-yl)-2-hydroxy-4-{[5-(4-methoxybenzyloxy)-1-methyl-1H-pyrazole-3-carbonyl]amino}pentanoic acid (28.0 mg, 49.6 μmol) was combined with HOBt (40.2 mg, 298 μmol) and EDC (53 μL, 0.3 mmol) in DCM (0.4 mL, 6 mmol). The resulting solution was stirred for 15 minutes before the addition of 2,2,3,3,3-pentafluoro-1-propanol (39.6 μL, 397 μmol). The mixture was stirred at room temperature and the reaction monitored for completion. After 4 hours, the mixture was concentrated by rotary evaporation and the reside was purified (reverse phase column).

The residue was dissolved in EtOAc (842 μL, 8.6 mmol) and 10% Pd/C, 50% wet (0.45 mmol/g loading; 31.9 mg, 14 μmol) was added. The resulting mixture was stirred under hydrogen for 1 hour. The solvent was removed in vacuo and the residue was purified by preparative HPLC to yield the title compound (4.9 mg, purity 100%). MS m/z [M+H]+ calc'd for $C_{25}H_{23}ClF_5N_3O_5$, 576.12; found 576.1.

Example 2E: (2R,4R)-5-(3'-Chlorobiphenyl-4-yl)-2-hydroxy-4-[(5-hydroxy-1-methyl-1H-pyrazole-3-carbonyl)amino]pentanoic Acid 1-Trifluoromethylpropyl Ester

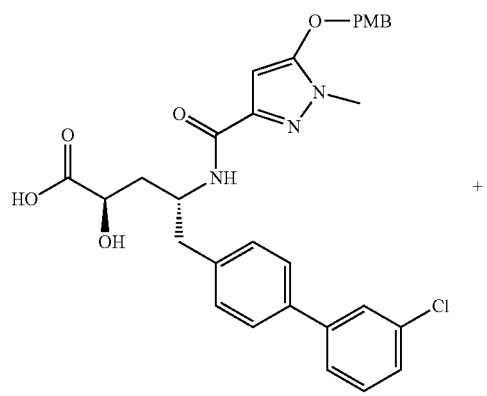

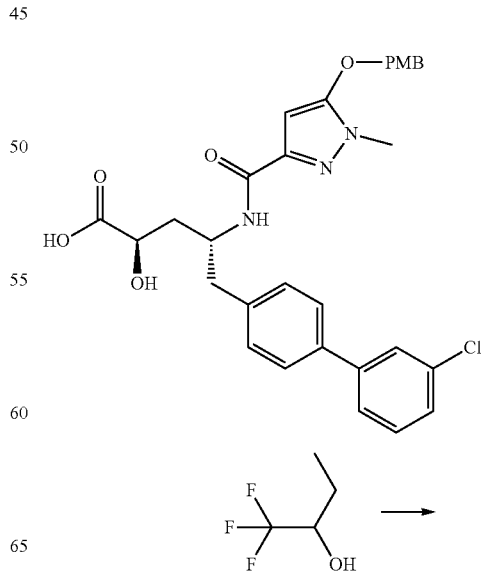

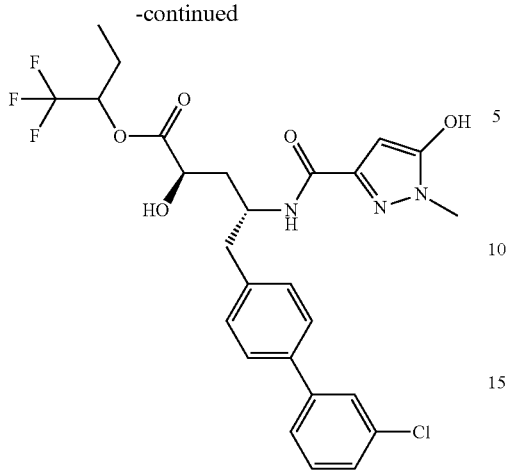

(2R,4R)-5-(3'-Chlorobiphenyl-4-yl)-2-hydroxy-4-{[5-(4-methoxybenzyloxy)-1-methyl-1H-pyrazole-3-carbonyl]amino}pentanoic acid (28.0 mg, 49.6 μmol) was combined with HOBt (40.2 mg, 298 μmol) and EDC (53 μL, 0.3 mmol) in DCM (0.4 mL, 6 mmol). The resulting solution was stirred for 15 minutes before the addition of 1,1,1-trifluoro-2-butanol (50.9 mg, 397 μmol). The mixture was stirred at room temperature and the reaction monitored for completion. After 4 hours, the mixture was concentrated by rotary evaporation and the reside was purified (reverse phase column).

The residue was dissolved in EtOAc (842 μL, 8.6 mmol), and 10% Pd/C, 50% wet (0.45 mmol/g loading; 31.9 mg, 14 μmol) was added. The resulting mixture was stirred under hydrogen for 1 hour. The solvent was removed in vacuo and the residue was purified by preparative HPLC to yield the title compound (1.3 mg, purity 99%). MS m/z [M+H]+ calc'd for $C_{26}H_{27}ClF_3N_3O_5$, 554.16; found 554.1.

Example 2F: (2R,4R)-5-(3'-Chlorobiphenyl-4-yl)-2-hydroxy-4-[(5-hydroxy-1-methyl-1H-pyrazole-3-carbonyl)amino]pentanoic Acid 2,2,3,3,3-Pentafluoro-1-Methylpropyl Ester

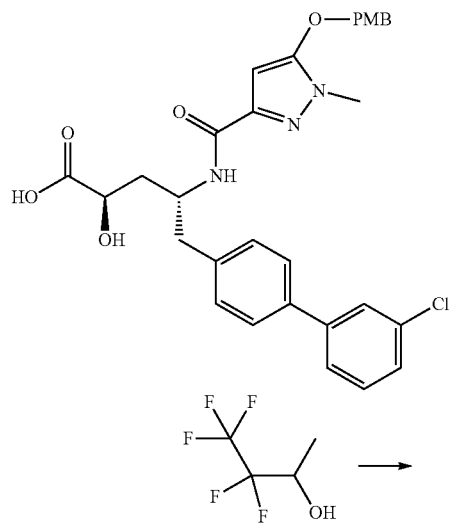

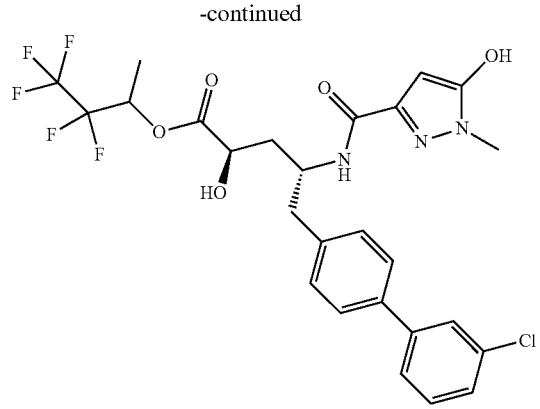

(2R,4R)-5-(3'-Chlorobiphenyl-4-yl)-2-hydroxy-4-{[5-(4-methoxybenzyloxy)-1-methyl-1H-pyrazole-3-carbonyl]amino}pentanoic acid (28.0 mg, 49.6 μmol) was combined with HOBt (40.2 mg, 298 μmol) and EDC (53 μL, 0.3 mmol) in DCM (0.4 mL, 6 mmol). The resulting solution was stirred for 15 minutes before the addition of 3,3,4,4,4-pentafluoro-2-butanol (65.2 mg, 397 μmol). The mixture was stirred at room temperature and the reaction monitored for completion. After 4 hours, the mixture was concentrated by rotary evaporation and the reside was purified (reverse phase column).

The residue was dissolved in EtOAc (842 μL, 8.6 mmol), and 10% Pd/C, 50% wet (0.45 mmol/g loading; 31.9 mg, 14 μmol) was added. The resulting mixture was stirred under hydrogen for 1 hour. The solvent was removed in vacuo and the residue was purified by preparative HPLC to yield the title compound (1.8 mg, purity 98%). MS m/z [M+H]+ calc'd for $C_{26}H_{25}ClF_5N_3O_5$, 590.14; found 590.1.

Example 2G: (2R,4R)-5-(3'-Chlorobiphenyl-4-yl)-2-hydroxy-4-[(5-hydroxy-1-methyl-1H-pyrazole-3-carbonyl)amino]pentanoic Acid Benzyl Ester

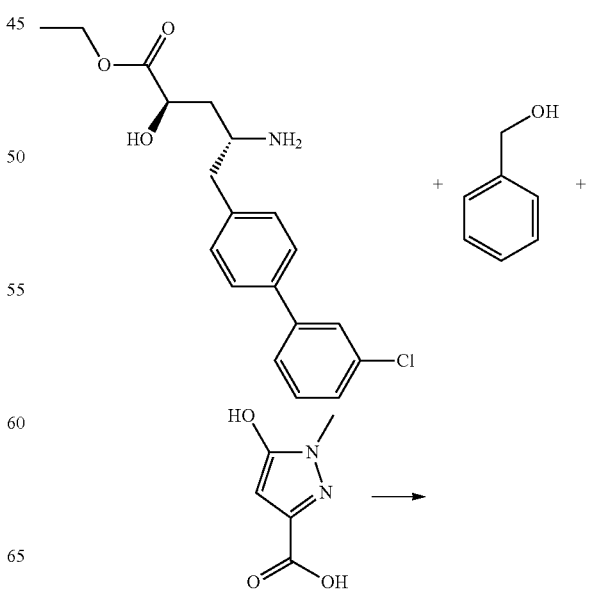

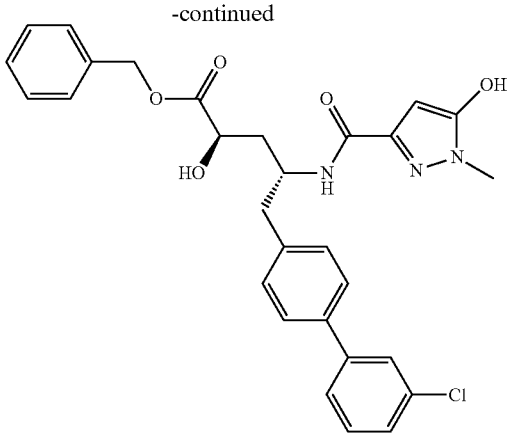

A mixture of (2R,4R)-4-amino-5-(3'-chlorobiphenyl-4-yl)-2-hydroxypentanoic acid ethyl ester (150.0 mg, 431 µmol), benzyl alcohol (446.2 µL, 4.3 mmol), and 4.0 M HCl in 1,4-dioxane (431 µL, 1.7 mmol) was stirred at room temperature overnight, then at 50° C. for 1 hour. The mixture was then concentrated under reduced pressure. 5-Hydroxy-1-methyl-1H-pyrazole-3-carboxylic acid (30.6 mg, 216 µmol) and HATU (98.4 mg, 259 µmol) were stirred in DMF (0.5 mL, 5 mmol) for 10 minutes, then added to the concentrated mixture, along with DIPEA (113 µL, 647 µmol). The resulting mixture was stirred at room temperature for 2 hours and concentrated under reduced pressure. The residue was dissolved in 50% AcOH-water (5 mL), filtered, and purified by reverse phase preparative HPLC to yield the title compound (81.4 mg).

Example 2H: (2R,4R)-5-(3'-Chlorobiphenyl-4-yl)-2-hydroxy-4-[(5-hydroxy-1-methyl-1H-pyrazole-3-carbonyl)amino]pentanoic Acid Butyryloxymethyl Ester

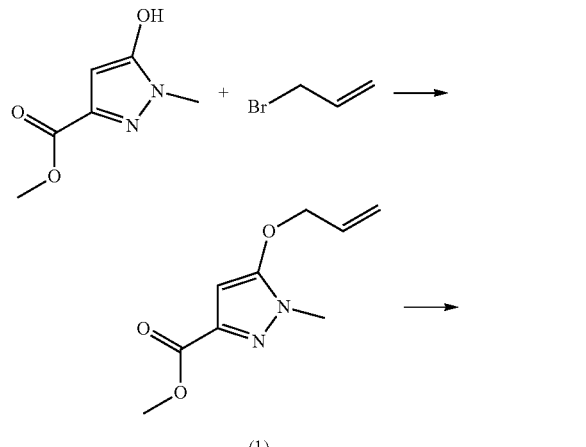

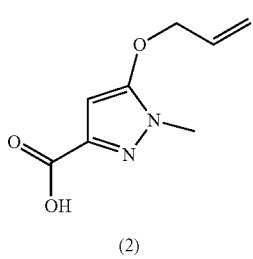

To a solution of 5-hydroxy-1-methyl-1H-pyrazole-3-carboxylic acid methyl ester (3 g, 19.2 mmol) in DMF (15 mL) was added $K_2CO_3$ (2.7 g, 19.2 mmol) at room temperature. After 10 min, allyl bromide (2.3 g, 19.2 mmol) was added, and the resulting mixture was stirred at room temperature for 2 hours. Water (150 mL) was added, the mixture was extracted with EtOAc (3×50 mL), and the combined organic layers were washed with saturated aqueous NaCl (50 mL) and dried over anhydrous $Na_2SO_4$. The solution was then evaporated and the residue was purified by silica gel chromatography (silica gel: 200-300 mesh, eluted with PE:EtOAc=10:1 to 5:1 to 1:1) to yield Compound 1 as a white solid (3 g). LC-MS: 197 [M+H]$^+$.

To a solution of Compound 1 (3 g, 15 mmol) in THF (30 mL) was added a solution of LiOH (550 mg, 23 mmol) in water (15 mL). The mixture was stirred at room temperature for 1 hour, then concentrated in vacuo. Water was added (20 mL) to the residue and the mixture was washed with EtOAc (20 mL). The aqueous layer was acidified with 1N aqueous HCl to pH=3 and extracted with EtOAc (3×30 mL). The combined organic layers were washed with saturated aqueous NaCl (30 mL), and dried over anhydrous $Na_2SO_4$. The solution was then evaporated to yield Compound 2 as a white solid (2.3 g). LC-MS: 183 [M+H]$^+$.

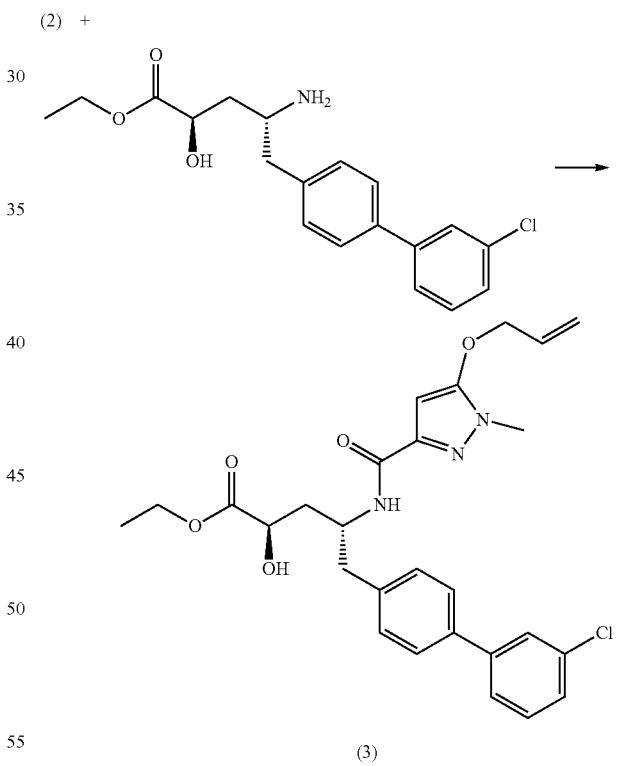

To a solution of (2R,4R)-4-amino-2-hydroxy-5-(3'-methylbiphenyl-4-yl)pentanoic acid ethyl ester (13 g, 7.1 mmol) and Compound 2 (2.7 g, 7.1 mmol) in DMF (30 mL) were added PyBOP (3.7 g, 7.1 mmol) and DIPEA (1.8 g, 14.2 mmol) at 0° C. The mixture was stirred at room temperature for 2 hours. Water was added (200 mL), the mixture was extracted with EtOAc (3×100 mL), and the combined organic layers were washed with saturated aqueous NaCl (100 mL) and dried over anhydrous $Na_2SO_4$. The mixture was concentrated and the residue was purified by silica gel chromatography (silica gel: 200-300 mesh; eluted with PE:EtOAc=10:1 to 5:1 to 1:1) to yield Compound 3 as a light yellow solid (2.4 g). LC-MS: 512 [M+H]+.

(3) →

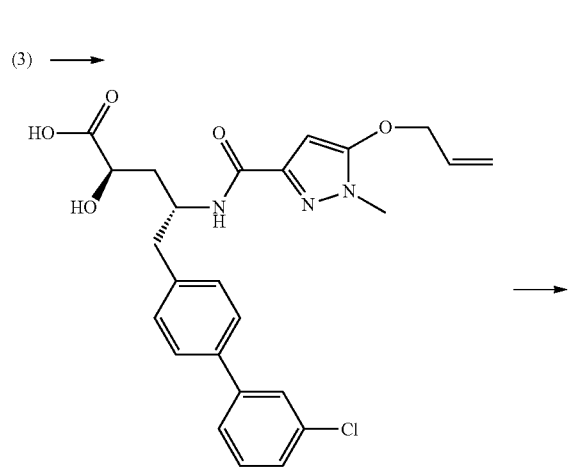

(4)

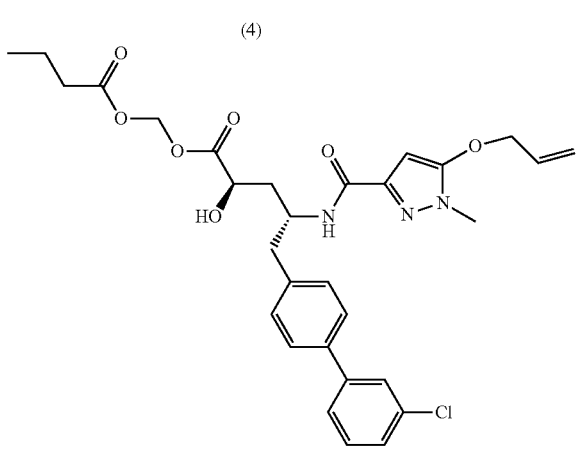

(5)

To a solution of Compound 3 (2.4 g, 4.7 mmol) in THF (20 mL) and water (10 mL) was added LiOH (169 mg, 7 mmol) at room temperature. The resulting mixture was stirred at room temperature for 1 hour. The mixture was concentrated, water was added (50 mL) and the mixture was washed with EtOAc (2×20 mL). The aqueous layer was acidified with 1N aqueous HCl to pH=3 and extracted with EtOAc (3×50 mL). The combined organic layers were washed with saturated aqueous NaCl (50 mL) and dried over anhydrous Na₂SO₄. The solution was then evaporated to yield Compound 4 as a yellow solid (2 g). LC-MS: 484 [M+H]+.

A suspension of Compound 4 (400 mg, 830 μmol), NaI (248 mg, 1.7 mmol) and lutidine (173 mg, 1.7 mmol) in chloromethyl butyrate (2 mL) was stirred at 50° C. for 5 hours. After cooling to room temperature, the mixture was diluted with water (20 mL) and extracted with EtOAc (2×20 mL). The combined organic layers were washed with saturated aqueous NaCl (40 mL), dried over anhydrous Na₂SO₄, concentrated, and purified by silica gel chromatography (silica gel: 200-300 mesh; elute with PE:EtOAc from 5:1 to 2:1) to yield Compound 5 as a light yellow solid (200 mg). LC-MS: 584 [M+H]+.

(5) →

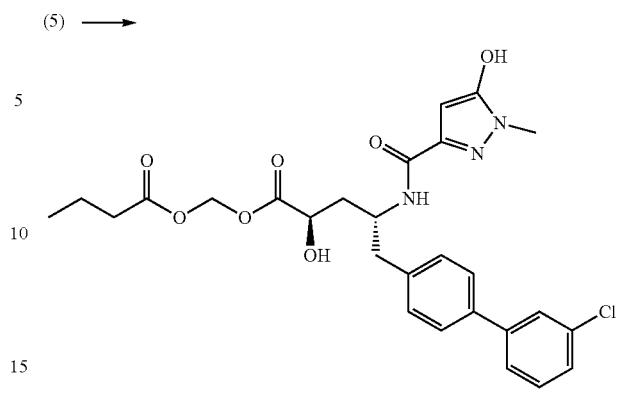

To a solution of Compound 5 (140 mg, 240 μmol) in DCM (5 mL) was added Pd(PPh₃)₄ (83 mg, 70 μmol), Et₃SiH (83 mg, 720 μmol) and AcOH (43 mg, 720 μmol). The mixture was stirred at room temperature for 4 hours and concentrated. The residue was purified by preparative HPLC [Daisogel-C18, 150×21.2 mm, 5μ; MeCN—H₂O (0.1% TFA) from 60% to 80%] to yield the title compound as a yellow oil (20 mg). LC-MS: 544 [M+H]+. ¹H-NMR (CD₃OD, 400 Hz): δ 0.93 (t, 3H), 1.62 (q, 2H), 2.06-2.13 (m, 2H), 2.31 (t, 2H), 2.97-2.99 (m, 2H), 3.65 (s, 3H), 4.32 (m, 1H), 4.51 (m, 1H), 5.75 (dd, 2H), 7.35-7.41 (m, 4H), 7.53-7.60 (m, 4H).

Example 2I: (2R,4R)-5-(3'-Chlorobiphenyl-4-yl)-2-hydroxy-4-[(5-hydroxy-1-methyl-1H-pyrazole-3-carbonyl)amino]pentanoic Acid (S)-2-Amino-3-methylbutyryloxymethyl Ester

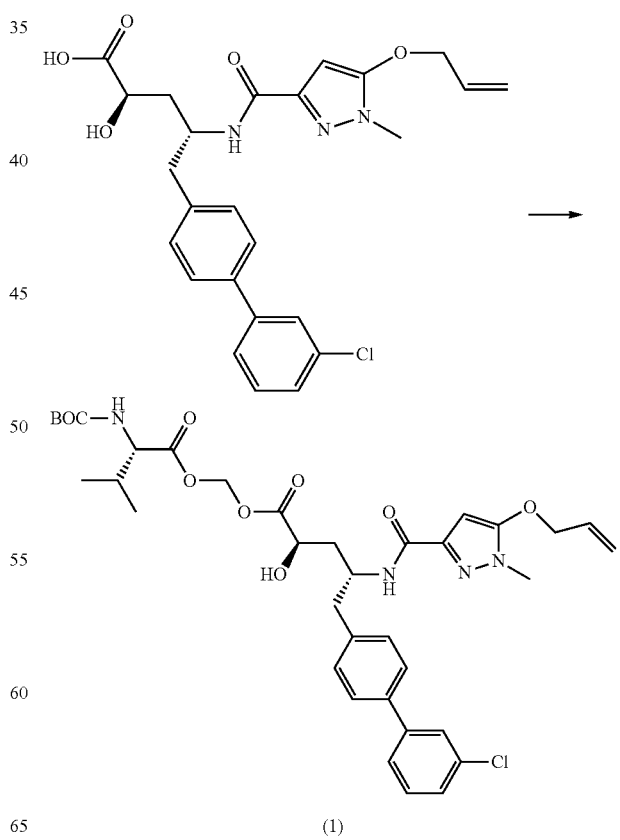

(1)

A suspension of (2R,4R)-4-[(5-allyloxy-1-methyl-1H-pyrazole-3-carbonyl)amino]-5-(3'-chlorobiphenyl-4-yl)-2-hydroxy-pentanoic acid (400 mg, 830 μmol), NaI (248 mg, 1.7 mmol) and lutidine (173 mg, 1.7 mmol) in (S)-2-t-butoxycarbonylamino-3-methylbutyric acid chloromethyl ester (2 mL) was stirred at 50° C. for 2 hours. After cooling to room temperature, the mixture was diluted with water (20 mL) and extracted with EtOAc (2×20 mL). The combined organic layers were washed with saturated aqueous NaCl (40 mL), dried over anhydrous Na$_2$SO$_4$, concentrated, and purified by silica gel chromatography (silica gel: 200-300 mesh; elute with PE:EtOAc from 5:1 to 2:1) to yield Compound 1 as a light yellow solid (290 mg). LC-MS: 713 [M+H]$^+$.

(1) ⟶

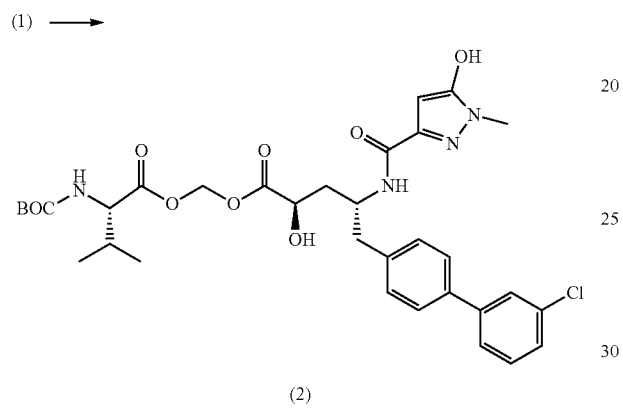

(2)

To a solution of Compound 1 (290 mg, 0.4 mmol) in THF (5 mL) was added Pd(PPh$_3$)$_4$ (70 mg, 60 μmol) and 1,3-dimethylbarbituric acid (312 mg, 2 mmol). The mixture was stirred at room temperature for 2 hours and concentrated. The residue was dissolved in EtOAc (30 mL), washed with 5% NaHCO$_3$ (2×15 mL), dried over anhydrous Na$_2$SO$_4$, and concentrated to yield crude Compound 2 as a brown solid (220 mg). LC-MS: 673 [M+H]$^+$.

(2) ⟶

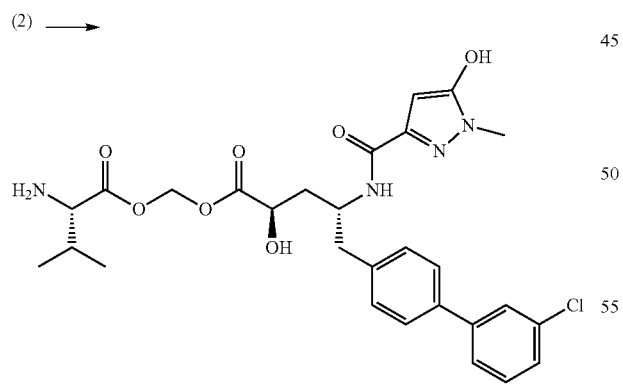

To a 1 M solution of HCl (g) in dioxane (5 mL) was added Compound 2 (220 mg, 330 μmol). The mixture was stirred at room temperature for 1 hour and concentrated. The residue was purified by preparative HPLC [Daisogel-C18, 150×21.2 mm, 5μ; MeCN—H$_2$O (0.1% TFA) from 35% to 45%] to yield the title compound as a yellow solid (100 mg). LC-MS: 573 [M+H]$^+$. $^1$H-NMR (DMSO-d6, 400 Hz): δ 0.97 (d, 6H), 1.82-1.85 (m, 1H), 1.98-2.01 (m, 1H), 2.16-2.19 (m, 1H), 2.85-2.88 (m, 2H), 3.58 (s, 3H), 3.99-4.01 (m, 1H), 4.18-4.20 (m, 1H), 4.23-4.25 (m, 1H), 5.84 (dd, 2H), 7.28-7.47 (m, 4H), 7.60-7.69 (m, 4H), 8.01 (s, 1H), 8.55 (br, 2H).

Example 3A: (2R,4R)-5-(3'-Chlorobiphenyl-4-yl)-2-hydroxy-4-[(5-hydroxy-1-pyridin-2-yl-1H-pyrazole-3-carbonyl)amino]pentanoic Acid

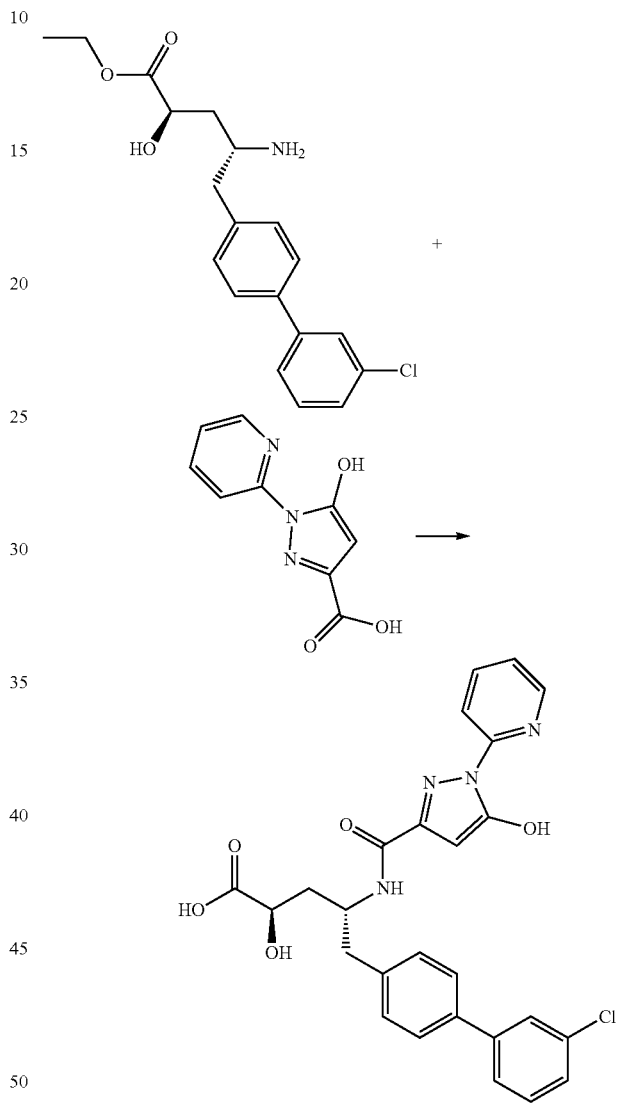

5-Hydroxy-1-pyridin-2-yl-1H-pyrazole-3-carboxylic acid (59.0 mg, 287 μmol) and HCTU (131 mg, 316 μmol) were combined in DMF (1.3 mL, 17.2 mmol), and stirred at room temperature for 15 minutes. (2R,4R)-4-amino-5-(3'-chloro-biphenyl-4-yl)-2-hydroxypentanoic acid 5-methyl-2-oxo[1,3]dioxol-4-ylmethyl ester (100 mg, 0.3 mmol) and DIPEA (150 μL, 862 μmol) were added, and the resulting mixture was stirred at room temperature for 15 minutes. The reaction was evaporated under reduced pressure. The residue was dissolved in EtOH and a solution of 1 M LiOH in water (1.4 mL, 1.4 mmol) was added. The resulting mixture was stirred at room temperature for 1 hour, then evaporated under reduced pressure. The residue was purified by preparative HPLC to yield the title compound (85 mg). MS m/z [M+H]$^+$ calc'd for C$_{26}$H$_{23}$ClN$_4$O$_5$, 507.14; found 507.1.

Example 3B: (2R,4R)-5-(3'-Chlorobiphenyl-4-yl)-2-hydroxy-4-[(5-hydroxy-1-pyridin-2-yl-1H-pyrazole-3-carbonyl)amino]pentanoic Acid 5-Methyl-2-oxo-[1,3]dioxol-4-ylmethyl Ester

Example 3C: (2R,4R)-5-(3'-Chlorobiphenyl-4-yl)-2-hydroxy-4-[(5-hydroxy-1-pyridin-2-yl-1H-pyrazole-3-carbonyl)amino]pentanoic Acid Ethyl Ester

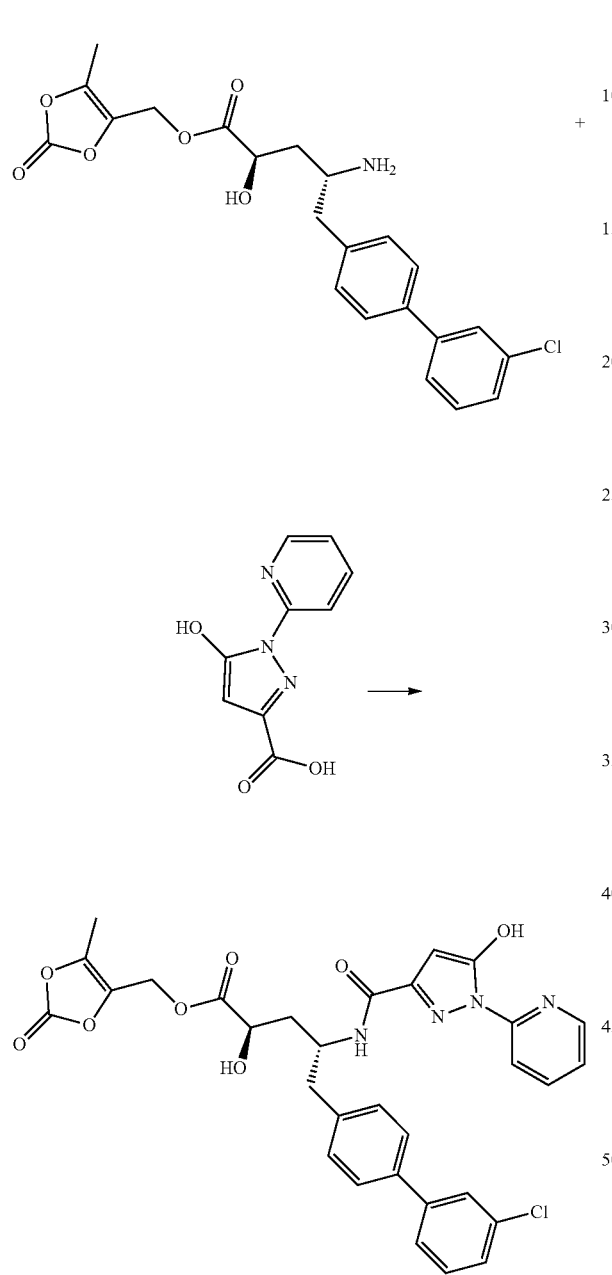

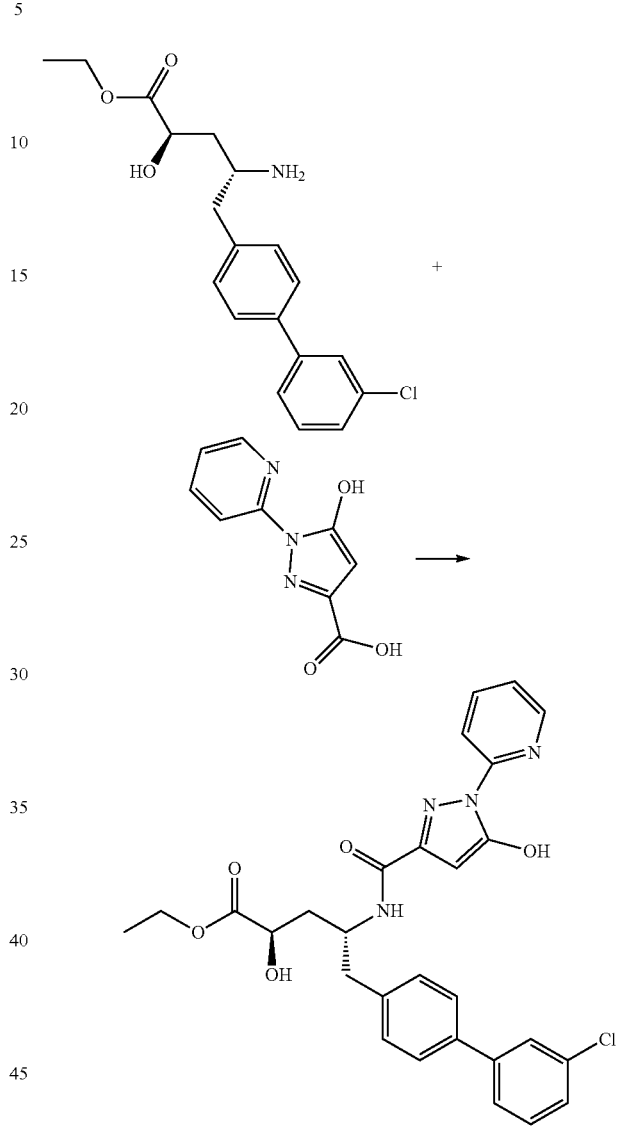

5-Hydroxy-1-pyridin-2-yl-1H-pyrazole-3-carboxylic acid (8.1 mg, 39 µmol) and HCTU (16.2 mg, 39 µmol) were combined in DMF (166 µL, 2.1 mmol) and stirred at room temperature for 15 minutes. DIPEA (19 µL, 0.1 mmol) and (2R,4R)-4-amino-5-(3'-chlorobiphenyl-4-yl)-2-hydroxypentanoic acid 5-methyl-2-oxo[1,3]dioxol-4-ylmethyl ester (15.4 mg, 36 µmol) were added, and the resulting mixture was stirred at room temperature for 30 minutes. The solvent was removed in vacuo and the crude product was purified by preparative HPLC to yield the title compound (18 mg). MS m/z [M+H]$^+$ calc'd for $C_{31}H_{27}ClN_4O_8$, 619.15; found 619.1.

5-Hydroxy-1-pyridin-2-yl-1H-pyrazole-3-carboxylic acid (23.6 mg, 115 µmol) and HATU (52.5 mg, 138 µmol) were stirred in N,N-dimethylacetamide (1.0 mL, 11 mmol) for 10 minutes. (2R,4R)-4-Amino-5-(3'-chlorobiphenyl-4-yl)-2-hydroxypentanoic acid ethyl ester (40.0 mg, 115 µmol) and DIPEA (60.1 µL, 345 µmol) were added, and resulting mixture was stirred at room temperature for 2 hours. The mixture was then concentrated under reduced pressure, the residue was dissolved in EtOAc (20 mL), and the organic layer was washed with water (2×5 mL), dried over MgSO$_4$, and concentrated. One half of the residue was dissolved in 50% AcOH-water (1.5 mL), filtered, and purified by reverse phase preparative HPLC to yield the title compound as a TFA salt (6.1 mg). MS m/z [M+H]$^+$ calc'd for $C_{28}H_{27}ClN_4O_5$, 535.17; found 535.4.

Example 3D: (2R,4R)-5-(3'-Chlorobiphenyl-4-yl)-2-hydroxy-4-[(5-hydroxy-1-pyridin-2-yl-1H-pyrazole-3-carbonyl)amino]pentanoic Acid Isobutyl Ester

Example 3E: (2R,4R)-5-(3'-Chlorobiphenyl-4-yl)-2-hydroxy-4-[(5-hydroxy-1-pyridin-2-yl-1H-pyrazole-3-carbonyl)amino]pentanoic Acid Benzyl Ester

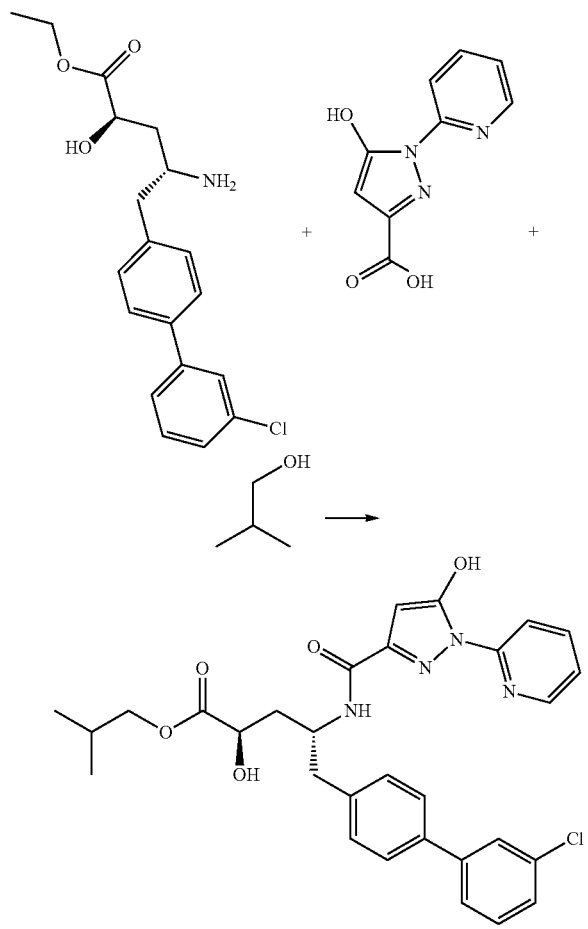

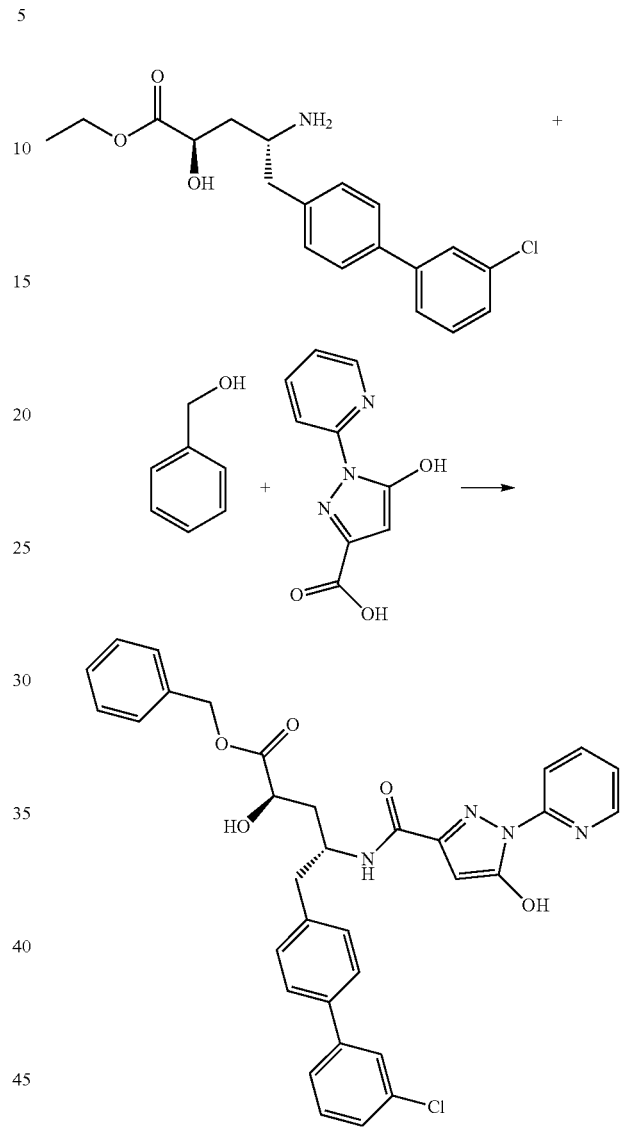

5-Hydroxy-1-pyridin-2-yl-1H-pyrazole-3-carboxylic acid (23.6 mg, 115 µmol) and HATU (52.5 mg, 138 µmol) were stirred in N,N-dimethylacetamide (1.0 mL, 11 mmol) for 10 minutes. (2R,4R)-4-Amino-5-(3'-chlorobiphenyl-4-yl)-2-hydroxypentanoic acid ethyl ester (40.0 mg, 115 µmol) and DIPEA (60.1 µL, 345 µmol) were added, and resulting mixture was stirred at room temperature for 2 hours. The mixture was then concentrated under reduced pressure, the residue was dissolved in EtOAc (20 mL), and the organic layer was washed with water (2×5 mL), dried over MgSO$_4$, and concentrated. One half of the residue was combined with isobutyl alcohol (0.5 mL, 5 mmol), and 4.0 M HCl in 1,4-dioxane (115 µL, 460 µmol). The mixture was stirred at room temperature overnight, concentrated under reduced pressure, the residue dissolved in 50% AcOH-water (1.5 ml), filtered, and purification by reverse phase preparative HPLC to yield the title compound as a TFA salt (9.1 mg). MS m/z [M+H]$^+$ calc'd for C$_{30}$H$_{31}$ClN$_4$O$_5$, 563.20; found 563.4.

A mixture of (2R,4R)-4-amino-5-(3'-chlorobiphenyl-4-yl)-2-hydroxypentanoic acid ethyl ester (150.0 mg, 431 µmol), benzyl alcohol (446.2 µL, 4.3 mmol), and 4.0 M HCl in 1,4-dioxane (431 µL, 1.7 mmol) was stirred at room temperature overnight, then at 50° C. for 1 hour. The mixture was then concentrated under reduced pressure. 5-Hydroxy-1-pyridin-2-yl-1H-pyrazole-3-carboxylic acid (44.2 mg, 216 µmol) and HATU (98.4 mg, 259 µmol) were stirred in DMF (0.5 mL, 5 mmol) for 10 minutes, then added to the concentrated mixture, along with DIPEA (113 µL, 647 µmol). The resulting mixture was stirred at room temperature for 2 hours and concentrated under reduced pressure. The residue was dissolved in 50% AcOH-water (5 mL), filtered, and purified by reverse phase preparative HPLC to yield the title compound (19.5 mg).

Example 3F: (2R,4R)-2-((S)-2-Amino-3-methylbutyryloxy)-5-(3'-chlorobiphenyl-4-yl)-4-[(5-hydroxy-1-pyridin-2-yl-1H-pyrazole-3-carbonyl)amino]pentanoic Acid

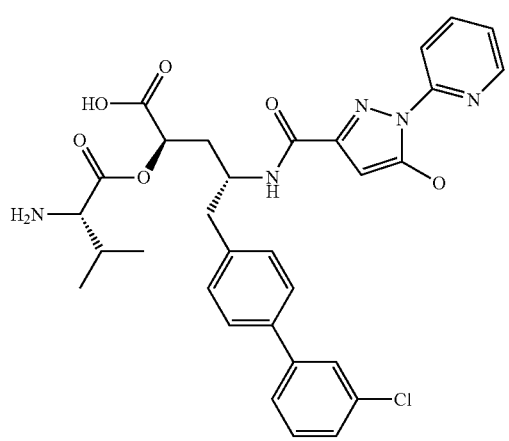 [SMILES: CC(C)[C@H](N)C(=O)O[C@H](C[C@@H](Cc1ccc(-c2cccc(Cl)c2)cc1)NC(=O)c1cc(O)n(-c2ccccn2)n1)C(=O)O]

Using the procedures described herein, the title compound can also be prepared.

Example 3G: (2R,4R)-4-{[5-((S)-2-Amino-3-methylbutyryloxymethoxy)-1-pyridin-2-yl-1H-pyrazole-3-carbonyl]amino}-5-(3'-chloro-biphenyl-4-yl)-2-hydroxypentanoic Acid

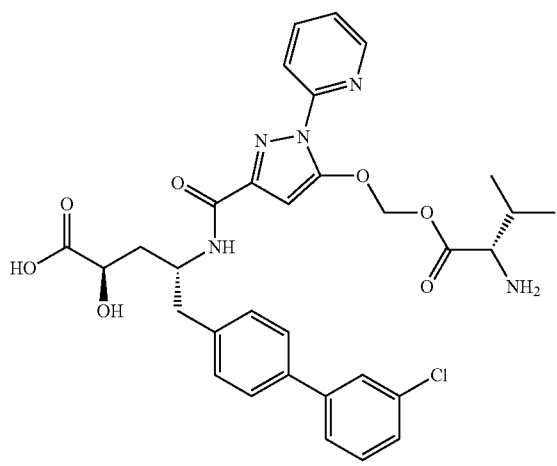 [SMILES: CC(C)[C@H](N)C(=O)OCOc1cc(C(=O)N[C@H](Cc2ccc(-c3cccc(Cl)c3)cc2)C[C@@H](O)C(=O)O)nn1-c1ccccn1]

Using the procedures described herein, the title compound can also be prepared.

Example 3H: (2R,4R)-5-(3'-Chlorobiphenyl-4-yl)-2-hydroxy-4-[(5-hydroxy-1-pyridin-2-yl-1H-pyrazole-3-carbonyl)amino]pentanoic Acid (S)-2-methoxycarbonylamino-3-methylbutyryloxymethyl Ester

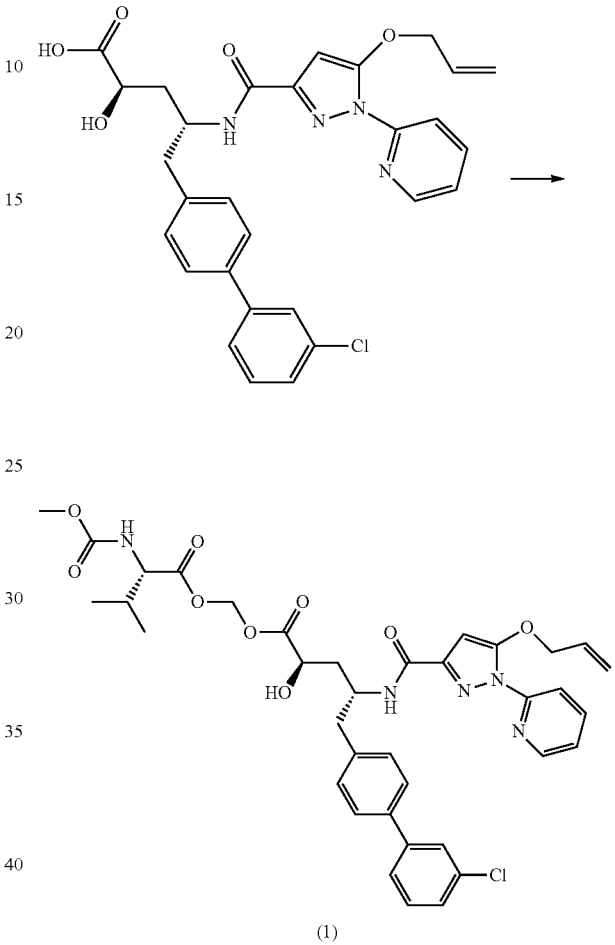

(1)

To a solution of (2R,4R)-4-[(5-allyloxy-1-pyridin-2-yl-1H-pyrazole-3-carbonyl)-amino]-5-(3'-chlorobiphenyl-4-yl)-2-hydroxypentanoic acid (220 mg, 0.4 mmol) and ((S)-2-methoxycarbonylamino-3-methylbutyric acid chloromethyl ester (180 mg, 0.8 mmol) in DMF (2 mL) was added 2,6-lutidine (130 mg, 1.2 mmol) and NaI (60 mg, 0.4 mmol). After stirring at room temperature for 24 hours, the mixture was diluted with water (20 mL) and extracted with EtOAc (2×20 mL). The combined organic layers were washed with saturated aqueous NaCl (2×70 mL), dried over anhydrous Na$_2$SO$_4$, filtered, concentrated and purified by preparative TLC (PE:EtOAc=1:1) to yield Compound 1 as a yellow solid (160 mg). LC-MS: 734 [M+H]$^+$.

(1) ⟶

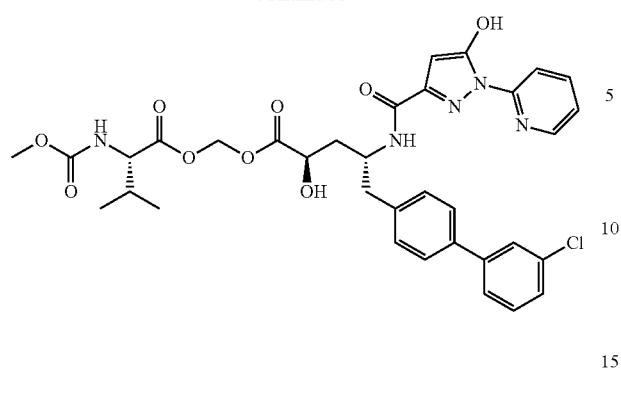

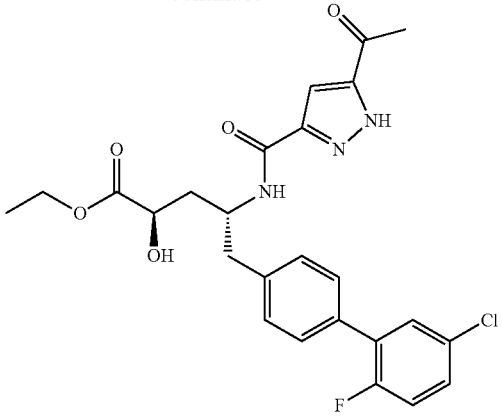

A mixture of Compound 1 (140 mg, 190 μmol), Et₃SiH (88 mg, 760 μmol), Pd(PPh₃)₄ (22 mg, 20 μmol), and AcOH (22 mg, 0.38 mmol) in DCM (2 mL) was stirred at room temperature for 4 hours. The solvent was removed and the residue was purified by preparative HPLC (Gemini-C18 150×21.2 mm, 5p; MeCN—H₂O (0.1% TFA); from 50% to 70%) to yield the title compound as a white solid (15 mg). LC-MS: 694 [M+H]⁺. ¹H NMR (400 MHz, CD₃OD) δ 8.47 (d, J=5.0 Hz, 1H), 8.06 (d, J=8.5 Hz, 2H), 7.55 (dd, J=19.3, 11.4 Hz, 4H), 7.37 (dt, J=28.2, 6.2 Hz, 5H), 5.85 (d, J=5.7 Hz, 1H), 5.75 (d, J=5.7 Hz, 1H), 4.58 (m, 1H), 4.36 (t, J=5.8 Hz, 1H), 4.04 (d, J=5.9 Hz, 1H), 3.65 (s, 3H), 3.04 (d, J=6.8 Hz, 2H), 2.20 (dd, J=12.5, 7.1 Hz, 1H), 2.08 (m, 2H), 0.90 (dd, J=10.8, 6.9 Hz, 6H).

Example 4A: (2R,4R)-4-[(5-Acetyl-1H-pyrazole-3-carbonyl)amino]-5-(5'-chloro-2'-fluorobiphenyl-4-yl)-2-hydroxypentanoic Acid Ethyl Ester

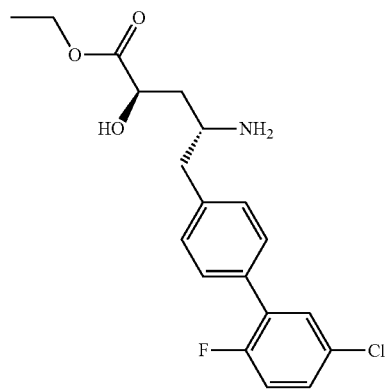

To a stirred solution of 3-acetyl-1H-pyrazole-5-carboxylic acid (50.9 mg, 330 μmol), HATU (125 mg, 330 μmol), and DIPEA (104 μL, 0.6 mmol) in DMF (0.6 mL, 7.7 mmol), was added (2R,4R)-4-amino-5-(5'-chloro-2'-fluorobiphenyl-4-yl)-2-hydroxypentanoic acid ethyl ester (110 mg, 300 μmol). The resulting mixture was stirred at room temperature until the reaction was complete. The mixture was diluted with DCM and washed with saturated aqueous NaHCO₃. The organics were dried over Na₂SO₄, and the solvent removed. Half of material was then purified by preparative HPLC to yield the title compound (22 mg) as a TFA salt. MS m/z [M+H]⁺ calc'd for C₂₅H₂₅ClFN₃O₅, 502.15; found 502.1.

Example 4B: (2R,4R)-4-[(5-Acetyl-1H-pyrazole-3-carbonyl)amino]-5-(5'-chloro-2'-fluorobiphenyl-4-yl)-2-hydroxypentanoic Acid

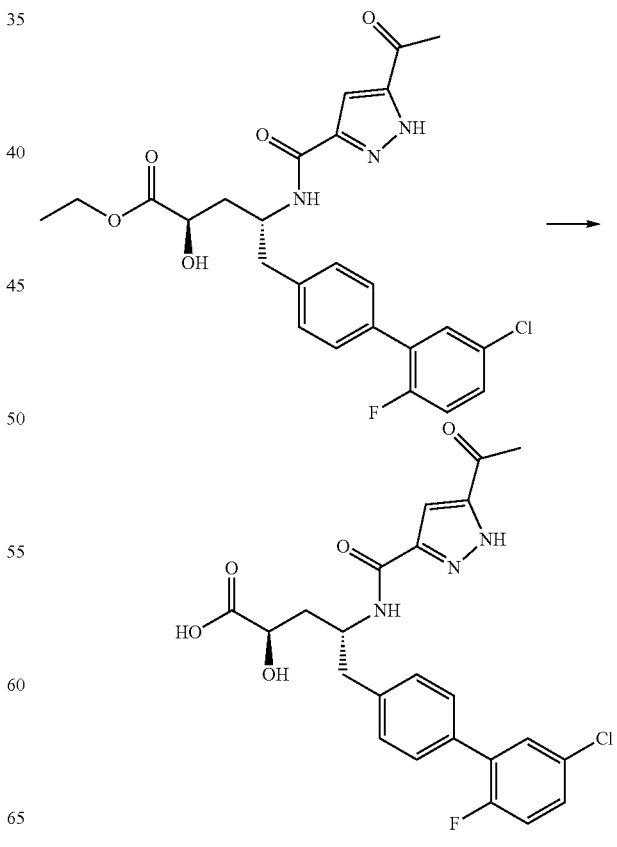

(2R,4R)-4-[(5-Acetyl-1H-pyrazole-3-carbonyl)amino]-5-(5'-chloro-2'-fluorobiphenyl-4-yl)-2-hydroxypentanoic acid ethyl ester (75 mg, 150 μmol) was stirred at room temperature with LiOH (10.8 mg, 450 μmol) in water (450 μL, 25 mmol) and EtOH (450 μL, 7.7 mmol), overnight. The solvent was removed and the remaining material was purified by preparative HPLC to yield the title compound (11.6 mg) as a TFA salt.

Example 5A: (2R,4R)-4-[(5-Acetyl-1H-pyrazole-3-carbonyl)amino]-5-(3'-chlorobiphenyl-4-yl)-2-hydroxypentanoic Acid Ethyl Ester

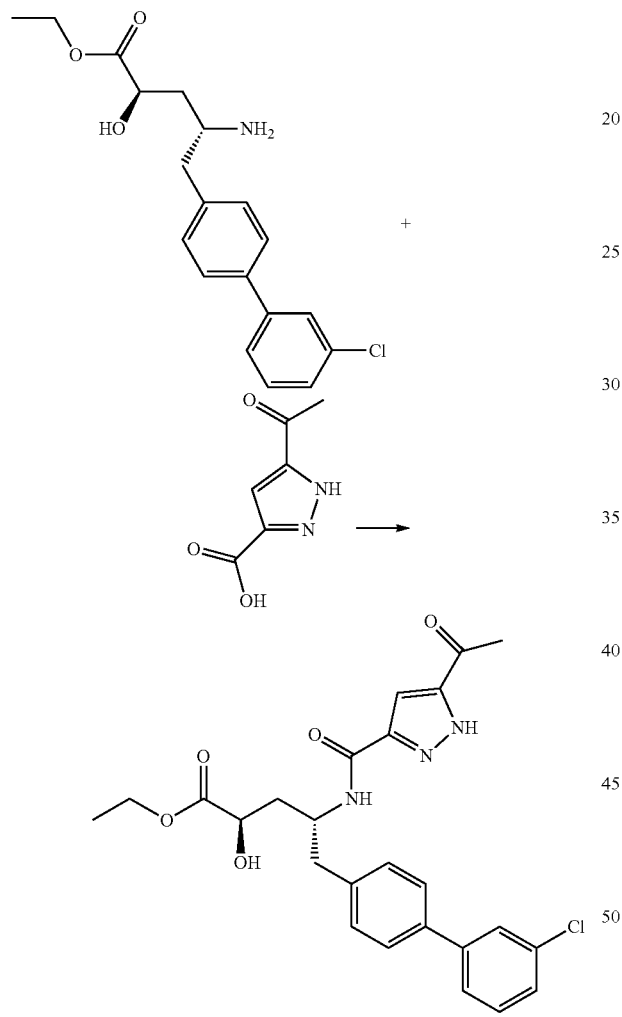

To a stirred solution of 3-acetyl-1H-pyrazole-5-carboxylic acid (50.9 mg, 330 pimp, HATU (125 mg, 330 pimp, and DIPEA (104 μL, 0.6 mmol) in DMF (0.6 mL, 7.7 mmol), was added (2R,4R)-4-amino-5-(3'-chlorobiphenyl-4-yl)-2-hydroxypentanoic acid ethyl ester (104 mg, 300 pimp. The resulting mixture was stirred at room temperature until the reaction was complete. The mixture was diluted with DCM and washed with saturated aqueous NaHCO₃. The organics were dried over Na₂SO₄, and the solvent removed. Half of material was then purified by preparative HPLC to yield the title compound (20 mg) as a TFA salt. MS m/z [M+H]⁺ calc'd for $C_{25}H_{26}ClN_3O_5$, 484.16; found 484.1.

Example 5B: (2R,4R)-4-[(5-Acetyl-1H-pyrazole-3-carbonyl)amino]-5-(3'-chlorobiphenyl-4-yl)-2-hydroxypentanoic Acid

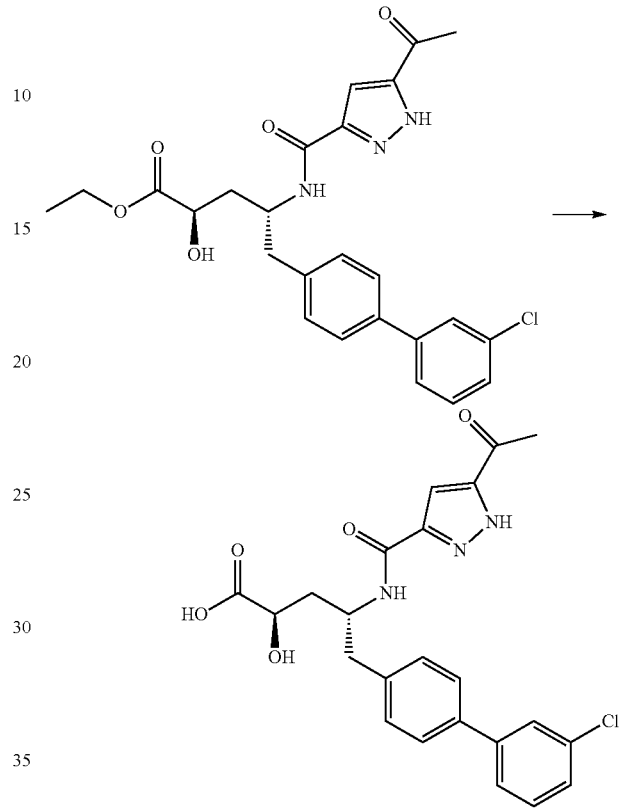

(2R,4R)-4-[(5-Acetyl-1H-pyrazole-3-carbonyl)amino]-5-(3'-chlorobiphenyl-4-yl)-2-hydroxy-pentanoic acid ethyl ester (72 mg, 150 μmol) was stirred at room temperature with LiOH (10.8 mg, 450 μmol) in water (450 μL, 25 mmol) and EtOH (450 μL, 7.7 mmol), overnight. The solvent was removed and the remaining material was purified by preparative HPLC to yield the title compound (11.5 mg) as a TFA salt.

Example 6A: (2R,4R)-5-(3'-Chlorobiphenyl-4-yl)-4-{[3-(2-fluorophenyl)isoxazole-5-carbonyl]amino}-2-hydroxypentanoic Acid

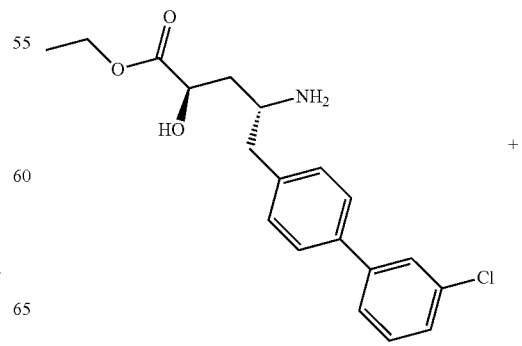

113

-continued

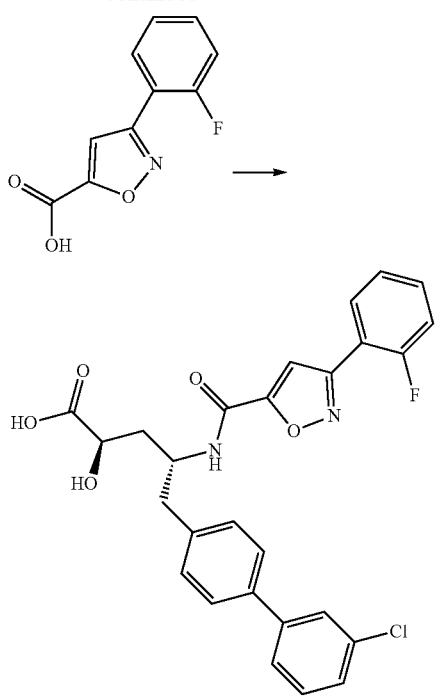

To a mixture of 3-(2-fluorophenyl)isoxazole-5-carboxylic acid (14.3 mg, 69 μmol) and HATU (26.2 mg, 69 μmol) in DMF (0.5 mL, 6 mmol) at room temperature, was added (2R,4R)-4-amino-5-(3'-chlorobiphenyl-4-yl)-2-hydroxypentanoic acid ethyl ester (20.0 mg, 58 μmol) and DIPEA (20.0 μL, 115 μmol). The mixture was stirred at room temperature overnight. MeOH (2.0 mL, 49 mmol), water (1.0 mL, 56 mmol), and LiOH monohydrate (9.7 mg, 230 pimp was added, and the resulting mixture was stirred at room temperature for 1 hour. The resulting solids were filtered and rinsed with MeCN and water to yield the title compound (17.1 mg). MS m/z [M+H]$^+$ calc'd for $C_{27}H_{22}ClFN_2O_5$, 509.12; found 509.

Example 6B: (2R,4R)-5-(3'-Chlorobiphenyl-4-yl)-4-{[3-(2-fluorophenyl)isoxazole-5-carbonyl]amino}-2-hydroxypentanoic Acid Ethoxycarbonyloxymethyl Ester

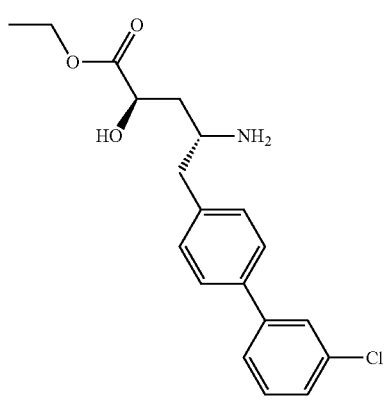

+

114

-continued

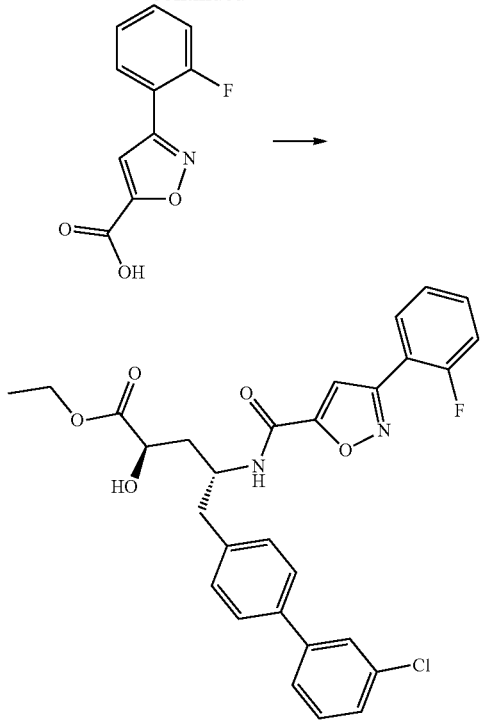

(1)

A solution of (2R,4R)-4-amino-5-(3'-chlorobiphenyl-4-yl)-2-hydroxypentanoic acid ethyl ester (HCl salt; 1.5 g, 4 mmol), 3-(2-fluorophenyl)isoxazole-5-carboxylic acid (814 mg, 4 mmol), HOBt (1.1 g, 8 mmol), EDC (1.5 g, 8 mmol) and DIPEA (1.6 g, 12 mmol) in DMF (50 ml) was stirred for 15 hours at room temperature. The reaction was quenched with water (50 mL) and extracted with EtOAc (3×60 mL), and organic layers were collected and concentrated. The residue was purified by column chromatography (petroleum ether/EtOAc=5:1) to yield Compound 1 (1.1 g). LC-MS: 537 [M+H]$^+$.

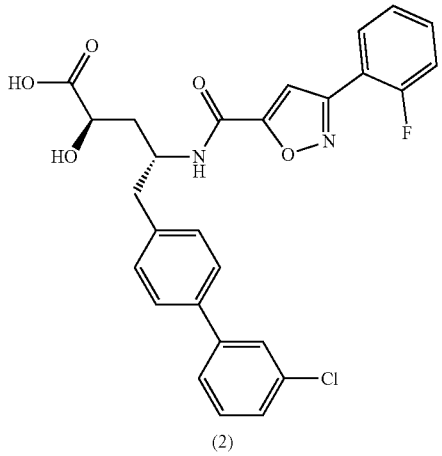

(1) →

(2)

A suspension of Compound 1 (200 mg, 0.37 mmol) and LiOH monohydrate (78 mg, 1.9 mmol) in THF/MeOH/H$_2$O (2:2:1 20 mL) was stirred for 3 hours at room temperature. The mixture was concentrated to remove the organic solvents, and the residue was adjusted to pH 6 with aq. HCl (1 M). The mixture was filtered to yield Compound 2 as white solid (120 mg). LC-MS: 509 [M+H]+.

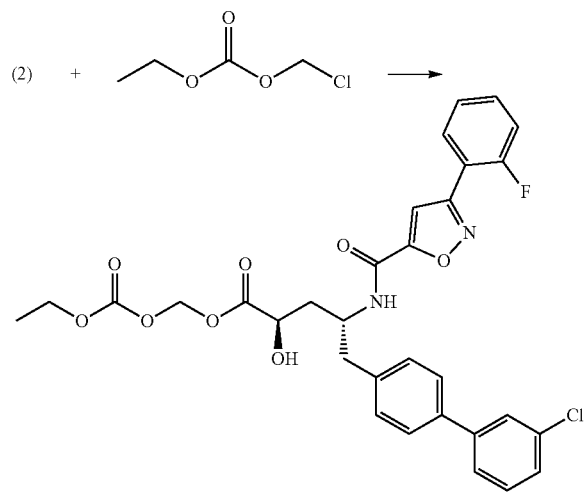

A suspension Compound 2 (150 mg, 0.3 mmol), chloromethyl ethyl carbonate (84 mg, 0.6 mmol), NaI (15 mg, 0.6 mmol), and pyridine (96 mg, 1.2 mmol) in DMF (20 mL) was stirred for 15 hours at 30° C. The reaction was quenched with water (15 mL) and extracted with EtOAc (3×30 mL). The combined organic layers were concentrated in vacuo and purified by column chromatography (petroleum ether/EtOAc=3:1) to yield the title compound as an off-white solid (10 mg). LC-MS: 611 [M+H]+. 1H NMR (400 MHz, CDCl3): δ 1.33 (t, J=7.2 Hz, 3H), 2.03-2.08 (m, 1H), 2.30-2.34 (m, 1H), 3.05 (d, J=6.4 Hz 2H), 4.26 (q, J=7.2 Hz, 2H), 4.48 (br, 1H), 4.75 (br, 1H), 5.68-5.70 (m, 1H), 5.81-5.83 (m, 1H), 6.88 (d, J=8.8 Hz, 1H), 7.28-7.34 (m, 7H), 7.42-7.53 (m, 4H), 7.96-7.99 (t, J=6.8 Hz, 1H).

Example 6C: (2R,4R)-5-(3'-Chlorobiphenyl-4-yl)-4-{[3-(2-fluorophenyl)isoxazole-5-carbonyl]amino}-2-hydroxypentanoic Acid Isopropoxycarbonyloxymethyl Ester

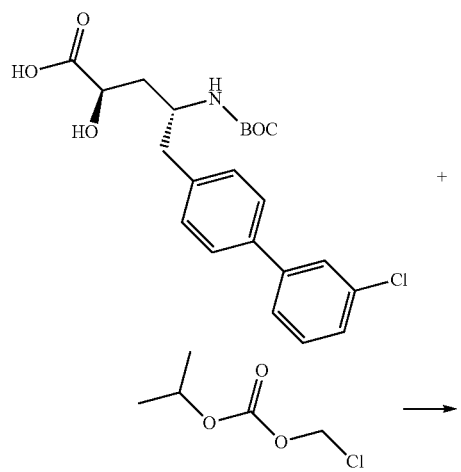

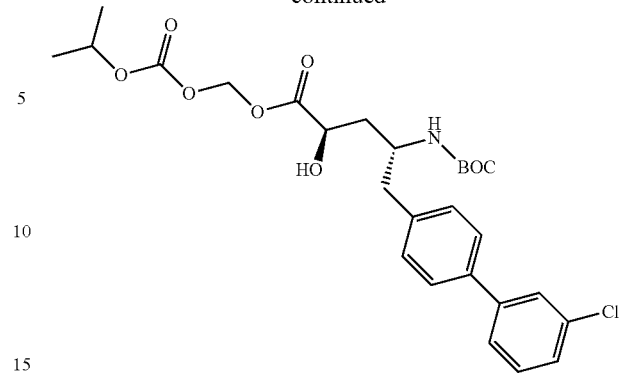

To a stirred solution of (2R,4R)-4-(t-butoxycarbonylamino)-5-(3'-chlorobiphenyl-4-yl)-2-hydroxypentanoic acid (2.4 g, 5.7 mmol) in DMF (50 mL) was added chloromethyl isopropyl carbonate (1.3 g, 8.6 mmol). To this mixture, NaI (1.71 g, 11.4 mmol) and DIPEA (2.2 g, 17.1 mmol) were added and the resulting mixture was stirred at room temperature overnight. Water (100 mL) was added and the mixture was extracted with EtOAc (3×80 mL). The combined organic layers were washed with saturated aqueous NaCl (2×100 mL) and water (2×100 mL), dried over anhydrous Na2SO4, and concentrated in vacuo. The product was purified by column chromatography (petroleum ether/EtOAc, 15:16:1) to yield Compound 1 as a white solid (574 mg). LC-MS: 558 [M+Na]+.

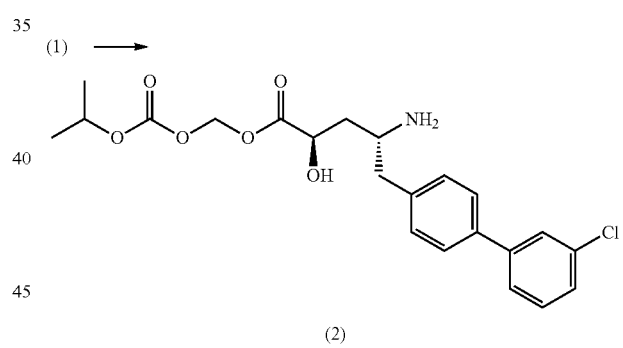

Compound 1 (574 mg, 1.1 mmol) was dissolved in an HCl-dioxane solution (1.4 M, 50 mL) at 0° C., and the resulting mixture was stirred at room temperature for 8 hours. After removal of the solvent, the residue was dispersed in EtOAc (10 mL). The precipitate was collected by filtration to yield Compound 2 as a white solid HCl salt (300 mg). LC-MS: 436 [M+H]+.

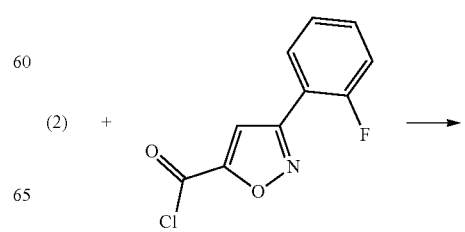

-continued

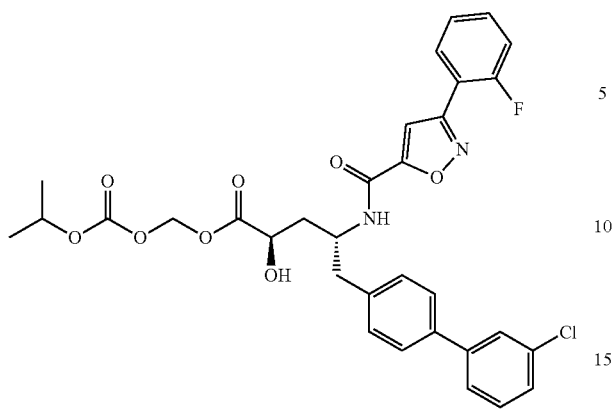

-continued

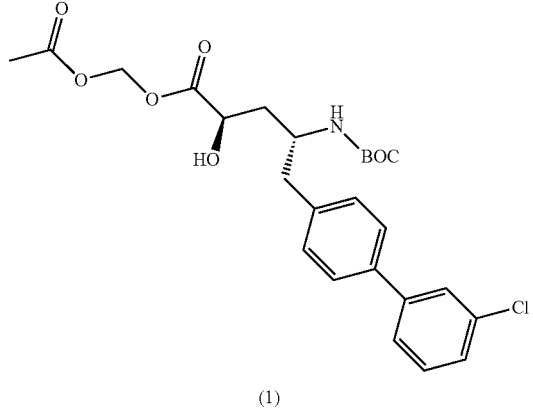

(1)

To a stirred solution of bromomethyl acetate (977 mg, 6.4 mmol) in DMF (10 mL) was added dropwise a solution of (2R,4R)-4-(t-butoxycarbonylamino)-5-(3'-chlorobiphenyl-4-yl)-2-hydroxypentanoic acid (1.8 g, 4.3 mmol) in DMF (10 mL) at room temperature. Pyridine (1.5 g, 19.2 mmol) was then added dropwise and the resulting mixture was stirred at room temperature overnight. Water (150 mL) was added and the mixture was extracted with EtOAc (3×100 mL). The combined organic layers were washed with saturated aqueous NaCl (2×100 mL) and water (3×100 mL), dried over anhydrous $Na_2SO_4$, and concentrated in vacuo. The crude product was purified by column chromatography (petroleum ether/EtOAc=6:1) to yield Compound 1 as a white solid (570 mg. LC-MS: 436 [M-tBu+H]$^+$.

To a solution of Compound 2 (150 mg, 340 μmol) in DMF (10 mL) was added 3-(2-fluorophenyl)-isoxazole-5-carbonyl chloride (79 mg, 380 μmol) and DIPEA (120 μL, 680 μmol). The mixture was stirred at room temperature overnight. Water (50 mL) was added, and the mixture was then extracted with EtOAc (3×30 mL). The combined organic layers were washed with saturated aqueous NaCl (2×50 mL) and water (2×50 mL), dried over anhydrous $Na_2SO_4$, and concentrated in vacuo. The residue was then purified by preparative HPLC (CAN-$H_2O$ (0.1% TFA), 75-80) to yield the title compound as a white solid (60 mg). LC-MS: 625 [M+H]$^+$. $^1$H-NMR (400 MHz, DMSO-$d_6$): δ 1.22-1.23 (m, 6H), 2.01-2.07 (m, 2H), 2.89-2.96 (m, 2H), 4.37-4.38 (m, 2H), 4.80 (br, 1H), 5.67-5.69 (m, 2H), 5.71-5.78 (m, 1H), 7.31-7.33 (m, 7H), 7.42-7.43 (m, 5H), 7.61-7.63 (m, 1H), 8.95 (d, J=6.8 Hz, 1H).

(1) →

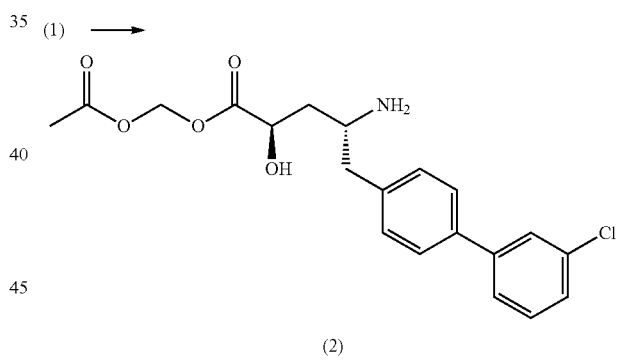

(2)

Compound 1 (570 mg, 1.2 mmol) was dissolved in an HCl-dioxane solution (1.4 mol/L, 50 mL) at 0° C. The resulting mixture was stirred at room temperature for 8 hours, then concentrated in vacuo. The residue was dispersed in EtOAc (10 mL). The precipitate was collected by filtration to yield Compound 2 as a white solid HCl salt (200 mg). LC-MS: 392 [M+H]$^+$.

Example 6D: (2R,4R)-5-(3'-Chlorobiphenyl-4-yl)-4-{[3-(2-fluorophenyl)isoxazole-5-carbonyl]amino}-2-hydroxypentanoic Acid Acetoxy methyl Ester

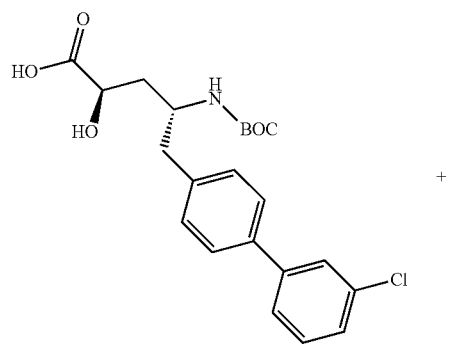

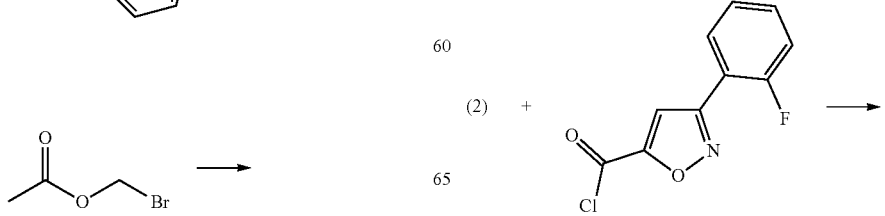

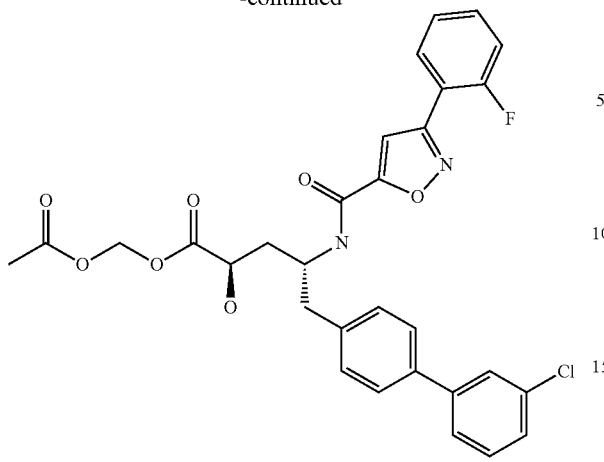
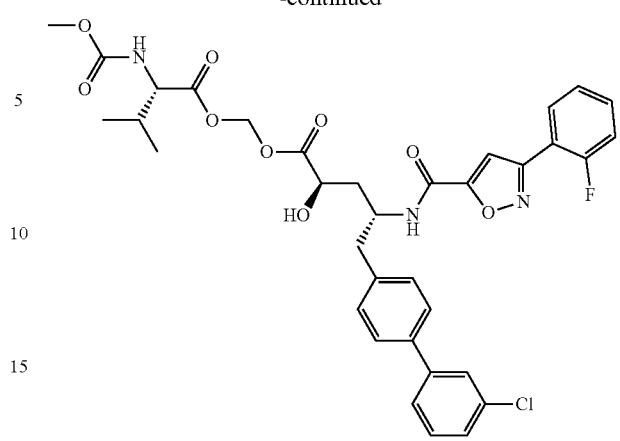

To a solution of Compound 2 (150 mg, 380 μmol) in THF (10 mL) was added 3-(2-fluorophenyl)-isoxazole-5-carbonyl chloride (79 mg, 380 μmol) and DIPEA (120 μL, 680 μmol). The mixture was stirred at room temperature overnight. Water (50 mL) was added, and the mixture was then extracted with EtOAc (3×20 mL). The organic layers were washed with saturated aqueous NaCl (2×30 mL) and water (2×30 mL), dried over anhydrous $Na_2SO_4$, and concentrated in vacuo. The residue was then purified by preparative HPLC (CAN-$H_2O$ (0.1% TFA), 75-80) to yield the title compound as a white solid (13 mg). LC-MS: 581 [M+H]$^+$. $^1$H NMR (400 MHz, DMSO-$d_6$): δ 1.90-1.99 (m, 2H), 2.07 (s, 3H), 2.89-2.96 (m, 2H), 4.27-4.38 (m, 2H), 5.67-5.69 (m, 2H), 5.78 (br, 1H), 7.31-7.33 (m, 7H), 7.42-7.43 (m, 5H), 7.61-7.63 (m, 1H), 8.95 (d, J=8.8 Hz, 1H).

Example 6E: (2R,4R)-5-(3'-Chlorobiphenyl-4-yl)-4-{[3-(2-fluorophenyl)isoxazole-5-carbonyl]amino}-2-hydroxypentanoic Acid (S)-2-Methoxycarbonylamino-3-methylbutyryloxymethyl Ester 2,6-Lutidine (96 mg, 0.9 mmol) was added to a solution of (2R,4R)-5-(3'-chlorobiphenyl-4-yl)-4-{[3-(2-fluorophenyl)isoxazole-5-carbonyl]amino}-2-hydroxypentanoic acid (150 mg, 0.3 mmol), (S)-2-methoxycarbonylamino-3-methylbutyric acid chloromethyl ester (134 mg, 0.6 mmol) and NaI (135 mg, 0.9 mmol) in DMF (10 mL). The mixture was stirred at 50° C. overnight. Water (20 mL) was added, and the mixture was extracted with ethyl ether (2×30 mL). The combined organic layers were dried over anhydrous $Na_2SO_4$ and concentrated in vacuo. The residue was purified by column chromatography (petroleum ether/EtOAc=4/11/2) to yield the title compound as an off-yellow solid (8 mg). LC-MS: 695.9 [M+H]$^+$. $^1$H-NMR (CD$_3$OD-$d_4$, 400 MHz) δ 0.92-0.95 (m, 6H), 2.03-2.08 (m, 3H), 3.00-3.10 (m, 2H), 4.09 (br, 1H), 4.27-4.28 (m, 1H), 4.87 (br, 1H), 5.75-5.85 (m, 2H), 7.26-7.37 (m, 6H), 7.51-7.53 (m, 6H), 7.93-7.95 (m, 1H).

Example 7A: (2R,4R)-5-(3'-Chlorobiphenyl-4-yl)-2-hydroxy-4-[(3-methoxyisoxazole-5-carbonyl)amino]pentanoic Acid

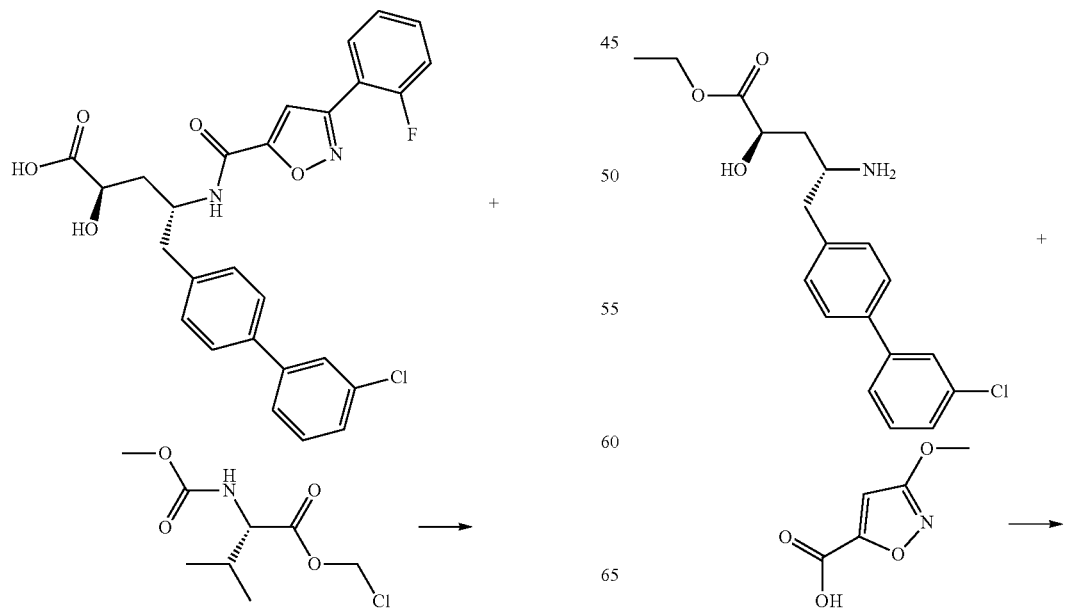

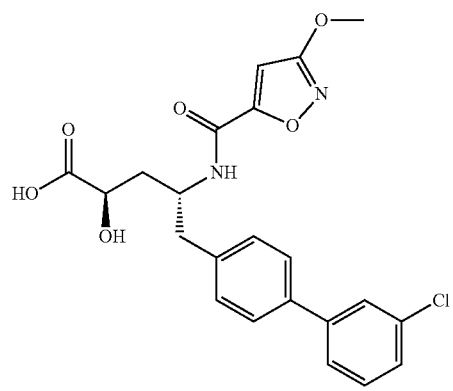

3-Methoxyisoxazole-5-carboxylic acid (39.4 mg, 275 µmol) and HCTU (128 mg, 310 µmol) were combined in DMF, and stirred for 10 minutes at room temperature. DIPEA (72 µL, 413 µmol) and (2R,4R)-4-amino-5-(3'-chlorobiphenyl-4-yl)-2-hydroxypentanoic acid ethyl ester (50 mg, 0.1 mmol) were added, and the resulting mixture was stirred at room temperature overnight. The mixture was combined with EtOH (402 µL, 6.9 mmol) and 1 M LiOH in water (1.1 mL, 1.1 mmol). The mixture was stirred at room temperature for 1 hour, evaporated under reduced pressure, and purified by preparative HPLC to yield the title compound. MS m/z [M+H]$^+$ calc'd for $C_{22}H_{21}ClN_2O_6$, 445.11; found 445.2.

Example 7B: (2R,4R)-5-(3'-Chlorobiphenyl-4-yl)-2-hydroxy-4-[(3-methoxyisoxazole-5-carbonyl)amino]pentanoic Acid 2-Methoxycarbonylamino-3-methyl-butyryloxymethyl Ester

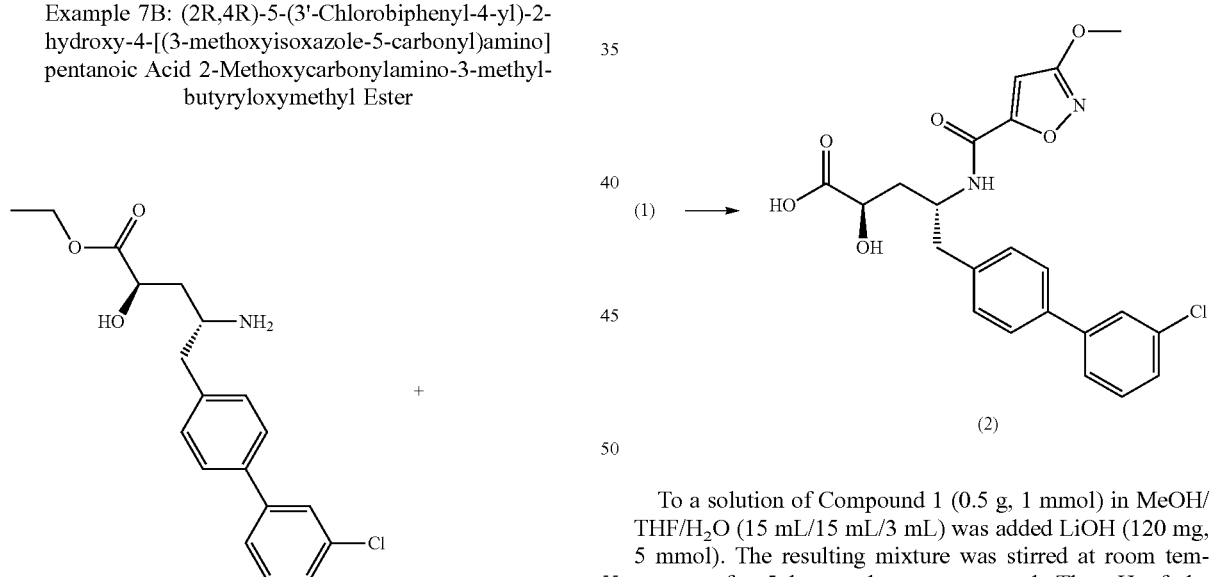

To a solution of (2R,4R)-4-amino-5-(3'-chlorobiphenyl-4-yl)-2-hydroxypentanoic acid ethyl ester (HCl salt, 1 g, 2.6 mmol) in THF (30 mL) was added a solution of 3-methoxy-isoxazole-5-carbonyl chloride (430 mg, 3 mmol) in THF (10 mL) and Et$_3$N (790 mg, 7.8 mmol) at 0° C. The resulting solution was stirred at room temperature for 6 hours, then concentrated in vacuo to yield a yellow solid which was purified by chromatography (PE:EtOAc=8:1) to yield Compound 1 as a white solid (0.9 g). LC-MS: 473 [M+H]$^+$.

To a solution of Compound 1 (0.5 g, 1 mmol) in MeOH/THF/H$_2$O (15 mL/15 mL/3 mL) was added LiOH (120 mg, 5 mmol). The resulting mixture was stirred at room temperature for 5 hours, then concentrated. The pH of the mixture was adjusted to pH 5 with HCl (1N, 20 mL). The solids were filtered to yield Compound 2 as a white solid (0.4 g). LC-MS: 445 [M+H]$^+$.

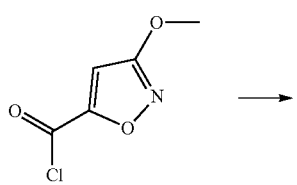

(2) + 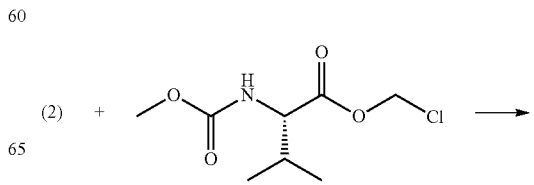

-continued

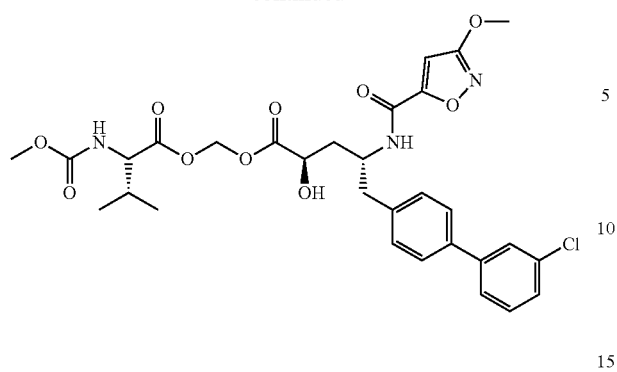

DIPEA (250 mg, 2 mmol) was added to a solution of Compound 2 (220 mg, 0.5 mmol), (S)-2-methoxycarbonylamino-3-methylbutyric acid chloromethyl ester (220 mg, 1 mmol) and NaI (300 mg, 2 mmol) in DMF (5 mL). The mixture was stirred at room temperature for 12 hours. The mixture was then poured into water (20 mL), extracted with EtOAc (3×15 mL), washed with saturated aqueous NaCl (30 mL), dried over anhydrous $Na_2SO_4$, and concentrated in vacuo. The residue was then purified by chromatography (petroleum ether:EtOAc=6:1) to yield the tile compound as a white solid (10 mg). LC-MS: 632 [M+H]$^+$. $^1$H NMR (400 MHz, DMSO-$d_6$): δ 0.86 (d, J=6.8 Hz, 6H), 1.97-2.02 (m, 3H), 2.92-2.94 (m, 2H), 3.92 (s, 3H), 4.36-4.21 (m, 2H), 5.70-5.79 (m, 2H), 6.72 (s, 1H), 7.29 (d, J=8.0 Hz, 2H), 7.46-7.61 (m, 2H), 7.60-7.69 (m, 4H), 8.73 (d, J=8.8 Hz, 1H).

Example 7C: (2R,4R)-5-(3'-Chlorobiphenyl-4-yl)-2-hydroxy-4-[(3-methoxy isoxazole-5-carbonyl)amino]pentanoic Acid Isopropoxycarbonyloxymethyl Ester

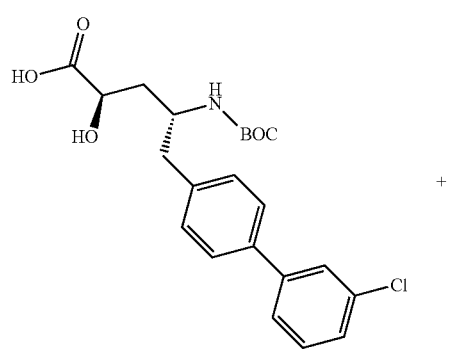

+

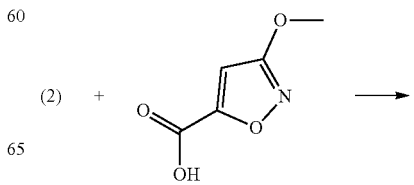

-continued

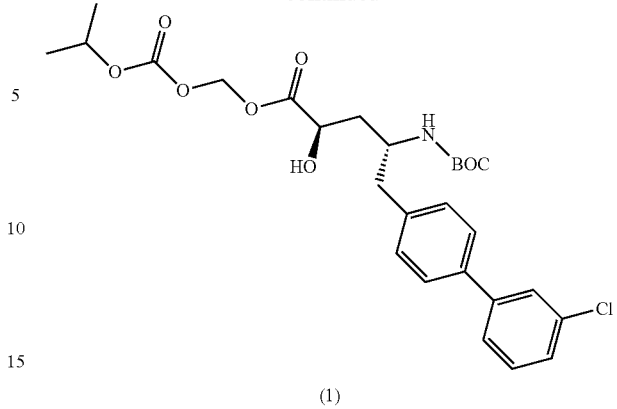

(1)

A mixture of (2R,4R)-4-(t-butoxycarbonylamino)-5-(3'-chlorobiphenyl-4-yl)-2-hydroxypentanoic acid (600 mg, 1.4 mmol), chloromethyl isopropyl carbonate (426 mg, 2.8 mmol), NaI (420 mg, 2.8 mmol) and DIPEA (546 mg, 4.2 mmol) in DMF (30.0 mL) was stirred at 25° C. overnight. The reaction mixture was poured into water (60 mL) and extracted with EtOAc (3×50 mL). The combined organic layers were washed with saturated aqueous NaCl (2×50 mL) and water (2×50 mL), dried over anhydrous $Na_2SO_4$, and concentrated in vacuo. The product was purified by column chromatography (petroleum ether:EtOAc=2:1) to yield Compound 1 as a colorless liquid (240 mg). LC-MS: 480 [M-tBu+H]$^+$.

(1) ⟶

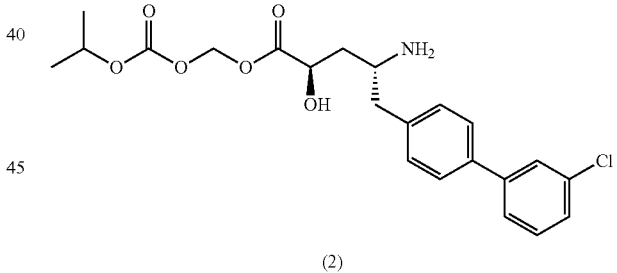

(2)

Compound 1 (240 mg, 0.45 mol) was dissolved in an HCl-dioxane solution (10.0 mL, 3.0 M) at 0° C., and the resulting mixture was stirred at room temperature overnight. The solvent was removed in vacuo. The residue was dispersed in EtOAc (10 mL). The precipitate was collected by filtration to yield Compound 2 as a white solid HCl salt (80 mg). LC-MS: 436 [M+H]$^+$.

(2) +  ⟶

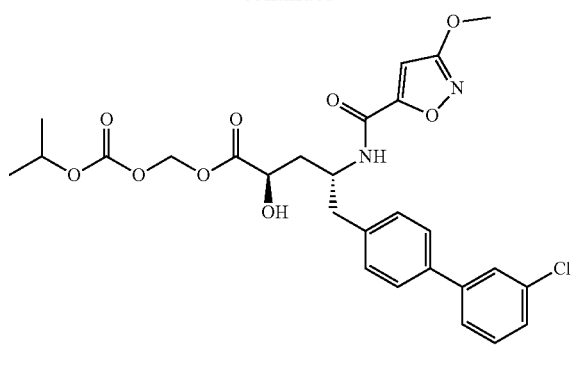

A mixture of Compound 2 (70 mg, 0.15 mmol), 3-methoxyisoxazole-5-carboxylic acid (43 mg, 0.3 mmol), HOBT (40 mg, 0.3 mmol), EDCI (57 mg, 0.3 mmol) and DIPEA (78 mg, 0.6 mmol) in DMF (10.0 mL) was stirred at room temperature overnight. The mixture was poured into water (30 mL) and extracted with EtOAc (3×30 mL). The organic layer was separated, washed with saturated aqueous NaCl (2×30 mL) and water (2×30 mL), dried over anhydrous $Na_2SO_4$, and concentrated in vacuo. The residue was purified by column chromatography (petroleum ether:EtOAc=2:1) to yield the title compound as a white solid (20 mg). LC-MS: 561 [M+H]$^+$. $^1$H NMR (400 MHz, CDCl$_3$) δ 1.30 (d, J=6.4 Hz, 6H), 2.04-2.05 (m, 1H), 2.25-2.29 (m, 1H), 2.99-3.01 (m, 2H), 3.48 (br, 1H), 4.00 (s, 3H), 4.46-4.48 (m, 1H), 4.50 (br, 1H), 4.92-4.93 (m, 1H), 5.69-5.79 (m, 2H), 6.51 (s, 1H), 6.79-6.70 (m, 1H), 7.28-7.57 (m, 8H).

Example 7D: (2R,4R)-5-(3'-Chlorobiphenyl-4-yl)-2-hydroxy-4-[(3-methoxyisoxazole-5-carbonyl)amino]pentanoic Acid Acetoxymethyl Ester

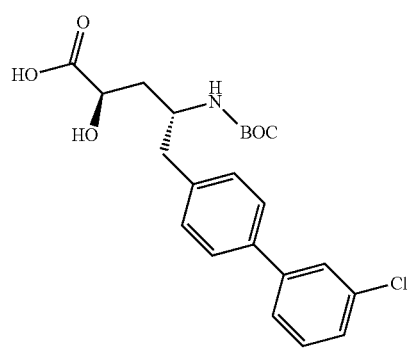

+

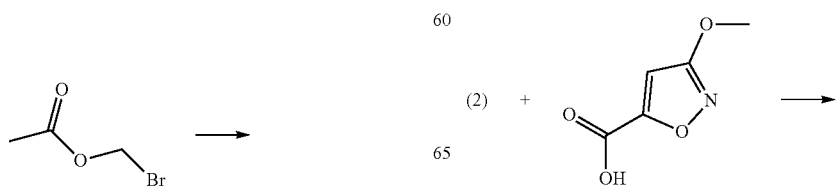

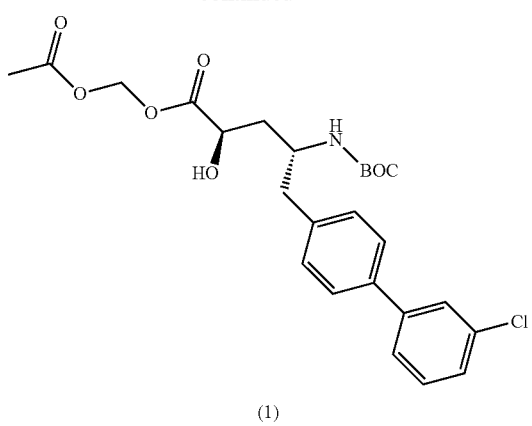

Bromomethyl acetate (977 mg, 6.4 mmol) was added to a stirred solution (2R,4R)-4-(t-butoxycarbonylamino)-5-(3'-chlorobiphenyl-4-yl)-2-hydroxypentanoic acid (1.8 g, 4.3 mmol) in DMF (20 mL) at room temperature. Pyridine (1.7 g, 21.5 mmol) was added dropwise and the resulting mixture was stirred at room temperature overnight. Water (50 mL) was added and the mixture was extracted with EtOAc (3×50 mL). The combined organic layers were washed with saturated aqueous NaCl (2×60 mL) and water (2×60 mL), dried over anhydrous $Na_2SO_4$, and concentrated in vacuo. The product was purified by column chromatography (petroleum ether:EtOAc, 15:16:1) to yield Compound 1 as a white solid (570 mg). LC-MS: 436 [M-tBu+H]$^+$.

(1) ⟶

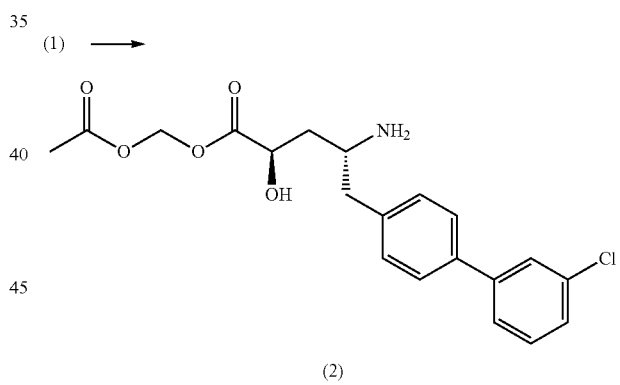

Compound 1 (570 mg, 1.2 mmol) was added to an HCl-dioxane solution (1.4 mol/L, 50 mL) at 0° C., and the resulting mixture was stirred at room temperature for 2 hours then concentrated in vacuo. The residue was dispersed in EtOAc (10 mL). The precipitate was collected by filtration to yield Compound 2 as a white solid HCl salt (200 mg). LC-MS: 392 [M+H]$^+$.

(2) +

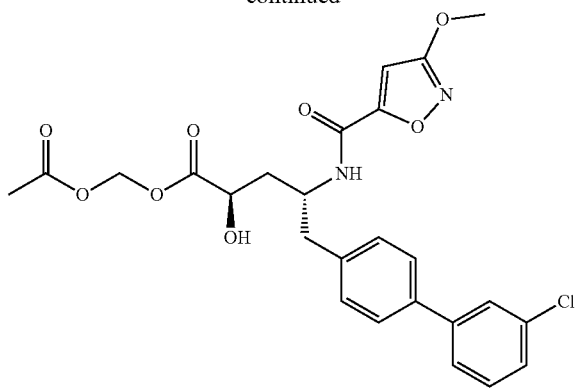

To a solution of Compound 2 (100 mg, 255 µmol) in DMF (10 mL) was added 3-methoxyisoxazole-5-carboxylic acid (79 mg, 383 µmol), HOBt (69 mg, 510 µmol), EDCI (98 mg, 510 µmol) and DIPEA (0.2 mL, 1.0 mmol). The mixture was stirred at room temperature overnight. Water (30 mL) was added and the mixture was extracted with EtOAc (3×30 mL). The combined organic layers were washed with saturated aqueous NaCl (2×30 mL) and water (2×30 mL), dried over anhydrous $Na_2SO_4$, and concentrated in vacuo. The residue was purified by preparative HPLC (CAN-$H_2O$ (0.1% TFA), 60-65) to yield the title compound as a white solid (15 mg). LC-MS: 517 [M+H]$^+$. $^1$H-NMR (DMSO-$d_6$, 400 Hz): δ 1.84-1.99 (m, 2H), 2.07 (s, 3H), 2.89-2.96 (m, 2H), 3.92 (s, 3H), 4.21-4.32 (m, 2H), 5.66-5.69 (m, 2H), 5.74 (br, 1H), 6.72 (s, 1H), 7.29 (d, J=8.4 Hz, 2H), 7.28-7.30 (m, 2H), 7.60-7.62 (m, 3H), 7.69 (s, 1H), 8.76 (d, J=8.8 Hz, 1H).

Example 7E: (2R,4R)-5-(3'-Chlorobiphenyl-4-yl)-2-hydroxy-4-[(3-methoxyisoxazole-5-carbonyl)-amino]pentanoic Acid Ethoxycarbonyloxymethyl Ester

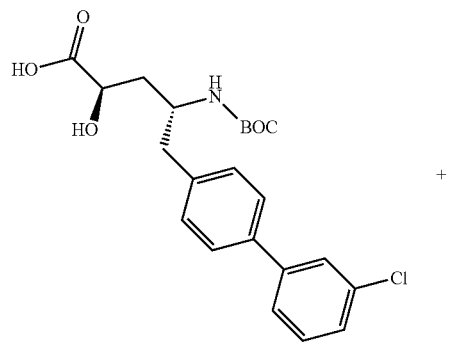

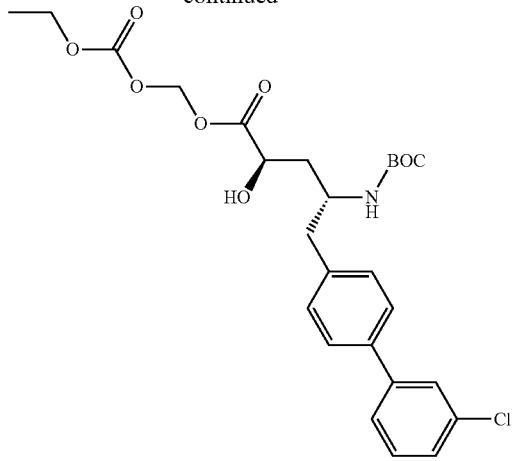

(1)

To a stirred solution of chloromethyl ethyl carbonate (0.2 mL, 1.1 mmol) in DMF (1 mL) was added dropwise a solution of (2R,4R)-4-(t-butoxycarbonylamino)-5-(3'-chlorobiphenyl-4-yl)-2-hydroxypentanoic acid (400 mg, 960 µmol) in DMF (6 mL) at room temperature. NaI (432 mg, 2.88 mmol) and DIPEA (0.5 mL, 2.88 mmol) were added and the resulting mixture was stirred at room temperature overnight. Water (50 mL) was added and the mixture was extracted with EtOAc (3×30 mL). The combined organic layers were washed with saturated aqueous NaCl (2×50 mL) and water (2×50 mL), dried over anhydrous $Na_2SO_4$, and concentrated in vacuo. The product was purified by column chromatography (petroleum ether:EtOAc, 15:16:1) to yield Compound 1 as a white solid (190 mg). LC-MS: 544 [M+Na]$^+$.

(1) ⟶

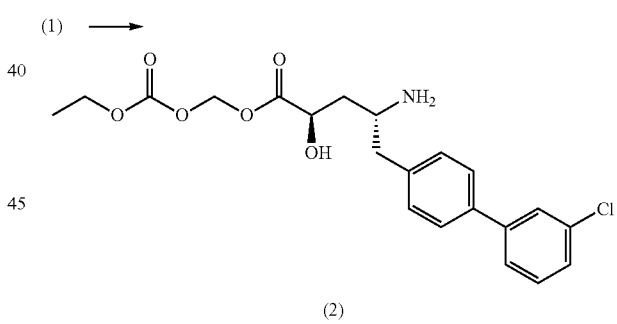

(2)

Compound 1 (190 mg, 360 µmol) was added to an HCl-dioxane solution (1.4 mol/L, 50 mL) at 0° C., and the resulting mixture was stirred at room temperature for 2 hours then concentrated in vacuo. The residue was dispersed in EtOAc (10 mL). The precipitate was collected by filtration to yield Compound 2 as a white solid HCl salt (150 mg). LC-MS: 422 [M+H]$^+$.

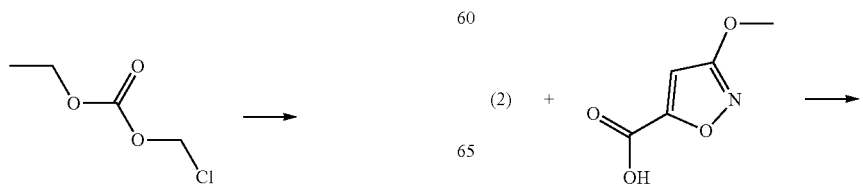

-continued

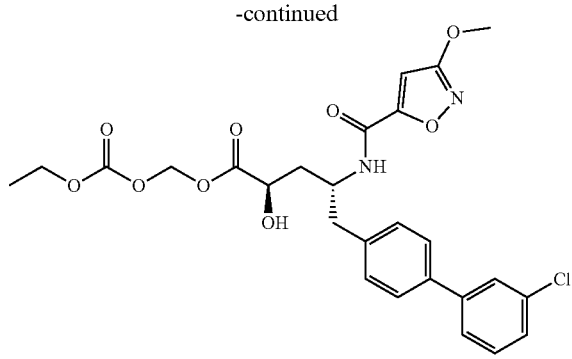

To a stirred solution of Compound 2 (150 mg, 360 μmol) in THF (20 mL) was added dropwise a solution of 3-methoxyisoxazole-5-carbonyl chloride (73 mg, 530 μmol) in THF (2 mL) at room temperature. DIPEA (0.2 mL) was added dropwise and the resulting mixture was stirred at room temperature overnight. Water (50 mL) was added and the mixture was extracted with Et$_2$O (3×40 mL). The combined organic layers were washed with saturated aqueous NaCl (2×50 mL) and water (2×50 mL), dried over anhydrous Na$_2$SO$_4$, and concentrated in vacuo. The residue was purified by preparative HPLC (CAN-H$_2$O (0.1% TFA), 60-70) to yield the title compound as a white solid (25 mg). LC-MS: 546.9 [M+H]$^+$. (DMSO-d$_6$, 400 MHz): δ 1.22 (t, J=6.8 Hz, 3H), 1.87-1.96 (m, 2H), 2.83-2.89 (m, 2H), 3.92 (s, 3H), 4.16 (q, J=6.8 Hz, 2H), 4.18-4.20 (m, 2H), 5.68-5.78 (m, 3H), 6.72 (s, 1H), 7.29 (d, J=8.0 Hz 2H), 7.45-7.48 (m, 2H), 7.60-7.62 (m, 3H), 7.69 (m, 1H), 8.76 (d, J=8.8 Hz, 1H).

Example 8A: (2R,4R)-5-(5'-Chloro-2'-fluorobiphenyl-4-yl)-2-hydroxy-4-[(1-hydroxy-1H-[1,2,3]triazole-4-carbonyl)amino]pentanoic Acid

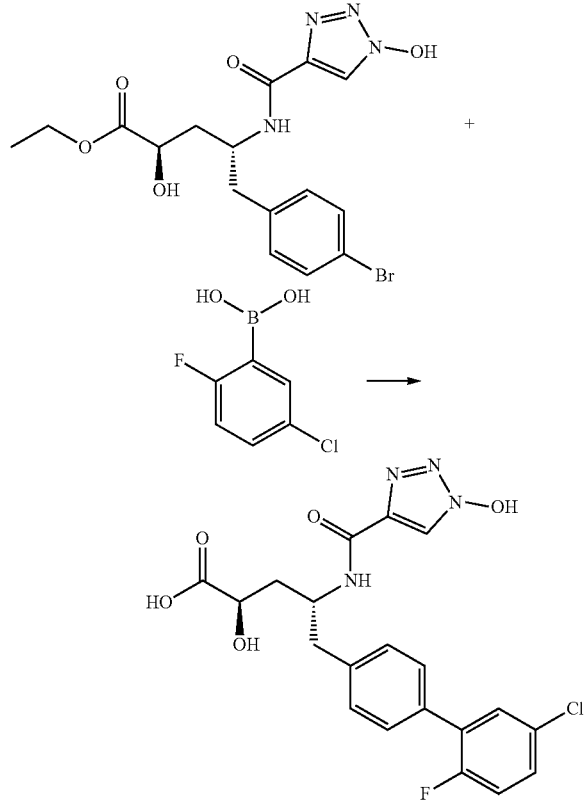

(2R,4R)-5-(4-Bromophenyl)-2-hydroxy-4-[(1-hydroxy-1H-1,2,3-triazole-4-carbonyl)amino]pentanoic acid ethyl ester (30 mg, 70 μmol) was combined with 5-chloro-2-fluorophenylboronic acid (22 mg, 126 μmol), K$_2$CO$_3$ (29.1 mg, 211 μmol), EtOH (0.8 mL, 10 mmol), and water (0.2 mL, 10 mmol). SilicaCat DPP-Pd (0.28 mmol/g loading; 25.1 mg, 7.0 μmol) was added the last. The resulting mixture was microwaved at 100° C. for 10 minutes. 1 M LiOH in water (281 μL, 281 μmol) was added, and the resulting mixture was stirred for 1 hour. The mixture was filtered, concentrated, and purified by preparative HPLC to yield the title compound (17 mg). MS m/z [M+H]$^+$ calc'd for C$_{20}$H$_{18}$ClFN$_4$O$_5$, 449.10; found 449.2.

Example 8B: (2R,4R)-5-(5'-Chloro-2'-fluorobiphenyl-4-yl)-2-hydroxy-4-[(1-hydroxy-1H-[1,2,3]triazole-4-carbonyl)amino]pentanoic Acid 2,2,3,3,3-pentafluoropropyl Ester

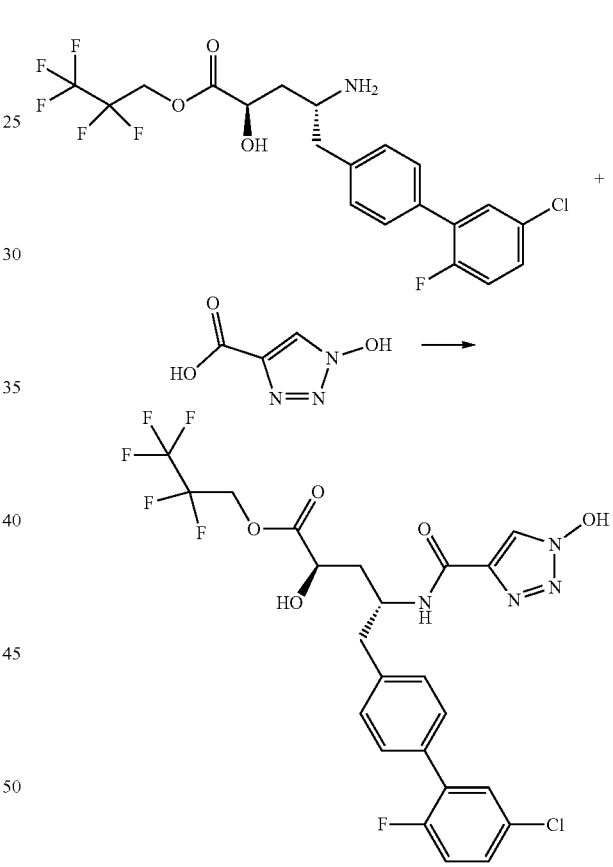

(2R,4R)-4-Amino-5-(5'-chloro-2'-fluorobiphenyl-4-yl)-2-hydroxypentanoic acid 2,2,3,3,3-pentafluoropropyl ester (32.1 mg, 68.3 μmol), 1-hydroxy-1H-[1,2,3]triazole-4-carboxylic acid (10.6 mg, 82 μmol) and HATU (39.0 mg, 102 μmol) were stirred in DMF (1.0 mL, 12.9 mmol) for 10 minutes. DIPEA (35.7 μL, 205 μmol) was added dropwise and the resulting mixture was stirred at room temperature for 1 hour. The mixture was concentrated and to yield a clear yellow liquid, which was purified using preparative scale C18 column chromatography (small column; 30-90% MeCN in water with 0.05% TFA) to yield the title compound as a white solid (4.9 mg). MS m/z [M+H]$^+$ calc'd for C$_{23}$H$_{19}$ClF$_6$N$_4$O$_5$, 581.09; found 581.

131

Example 8C: (2R,4R)-5-(5'-Chloro-2'-fluorobiphenyl-4-yl)-2-hydroxy-4-[(1-hydroxy-1H-[1,2,3]triazole-4-carbonyl)amino]pentanoic Acid 5-Methyl-2-oxo-[1,3]dioxol-4-ylmethyl Ester

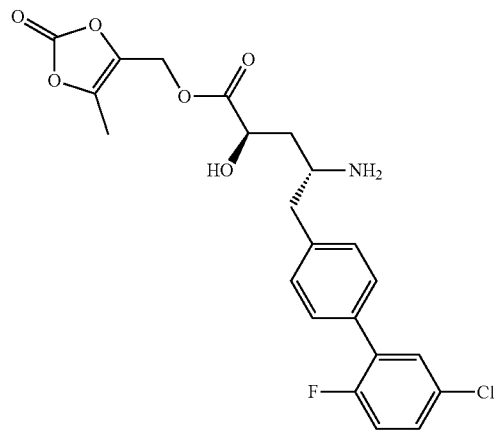

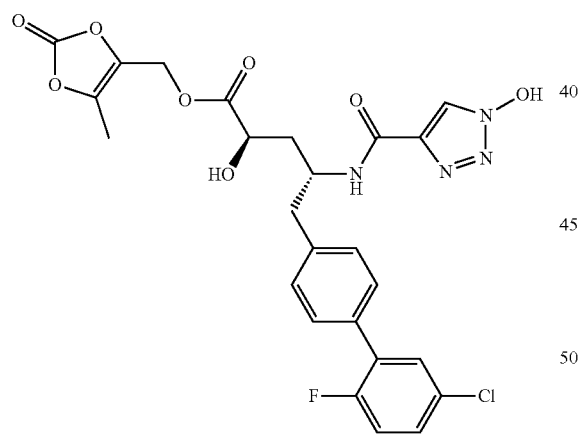

(2R,4R)-4-Amino-5-(5'-chloro-2'-fluorobiphenyl-4-yl)-2-hydroxypentanoic acid 5-methyl-2-oxo-[1,3]dioxol-4-ylmethyl ester (30.7 mg, 68.3 μmol), 1-hydroxy-1H-[1,2,3]triazole-4-carboxylic acid (10.6 mg, 82 μmol) and HATU (39.0 mg, 102 μmol) were stirred in DMF (1.0 mL, 12.9 mmol) for 10 minutes. DIPEA (35.7 μL, 205 μmol) was added dropwise and the resulting mixture was stirred at room temperature for 1 hour. The mixture was concentrated and to yield a clear yellow liquids, which was purified using preparative scale C18 column chromatography (small column; 30-90% MeCN in water with 0.05% TFA) to yield the title compound as a white solid (27.1 mg). MS m/z [M+H]$^+$ calc'd for $C_{25}H_{22}ClFN_4O_8$, 561.11; found 561.1.

132

Example 8D: (2R,4R)-5-(5'-Chloro-2'-fluorobiphenyl-4-yl)-2-hydroxy-4-{[1-(5-methyl-2-oxo-[1,3]dioxol-4-ylmethoxy)-1H-[1,2,3]triazole-4-carbonyl]amino}pentanoic Acid

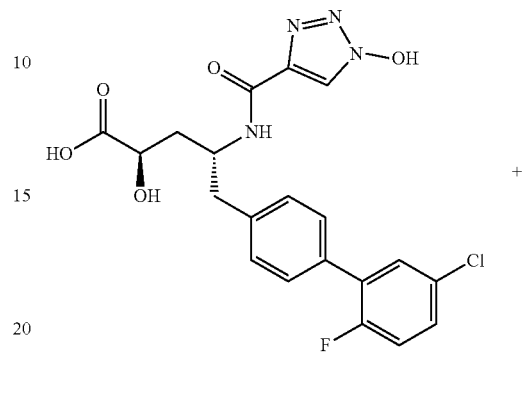

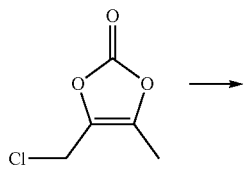

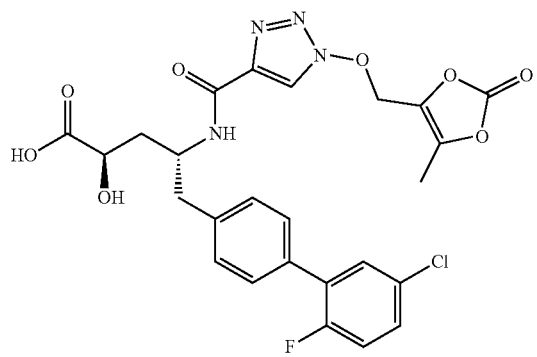

4-Chloromethyl-5-methyl-1,3-dioxol-2-one (11.0 μL, 100 μmol) was added to a solution of (2R,4R)-5-(5'-chloro-2'-fluorobiphenyl-4-yl)-2-hydroxy-4-[(1-hydroxy-1H-1,2,3-triazole-4-carbonyl)amino]pentanoic acid (30.0 mg, 66.8 μmol) in acetone (0.5 mL, 6.8 mmol). Et$_3$N (18.6 μL, 134 μmol) was added and the resulting mixture was stirred at 65° C. for 2 hours. The mixture was concentrated in vacuo to yield a yellow solid. The crude solid was purified by preparative scale HPLC (C18 column chromatography, small column, using 30-90% MeCN in water with 0.05% TFA) to yield the title compound as a white solid (6.5 mg). MS m/z [M+H]$^+$ calc'd for $C_{25}H_{22}ClFN_4O_8$, 561.11; found 561.1.

133

Example 8E: (2R,4R)-4-[(1-Butyryloxymethoxy-1H-[1,2,3]triazole-4-carbonyl)amino]-5-(5'-chloro-2'-fluorobiphenyl-4-yl)-2-hydroxypentanoic Acid

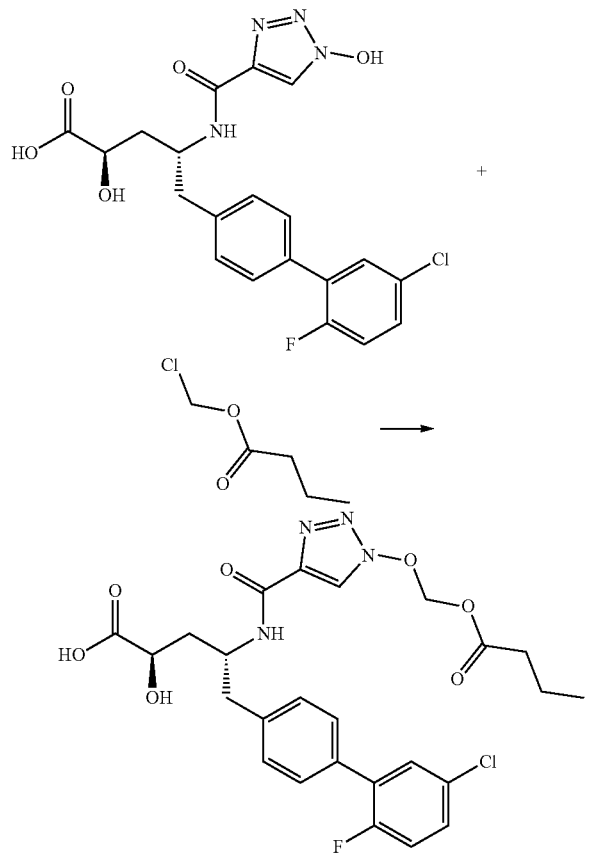

Chloromethyl butyrate (13.7 mg, 100 µmol) was added to a solution of (2R,4R)-5-(5'-chloro-2'-fluorobiphenyl-4-yl)-2-hydroxy-4-[(1-hydroxy-1H-1,2,3-triazole-4-carbonyl) amino]pentanoic acid (30.0 mg, 66.8 µmol) in acetone (0.5 mL, 6.8 mmol). Et₃N (18.6 µL, 134 µmol) was added and the resulting mixture was stirred at 65° C. for 2 hours. The mixture was then concentrated in vacuo to yield a yellow liquid. The crude liquid was purified (preparative scale C18 column chromatography, small column, using 30-90% MeCN in water with 0.05% TFA) to yield the title compound as a white solid (6.0 mg). MS m/z [M+H]⁺ calc'd for C₂₅H₂₆ClFN₄O₇, 549.15; found 549.1.

Example 8F: (2R,4R)-4-{[1-((S)-2-Amino-3-methylbutyryloxymethoxy)-1H-[1,2,3]triazole-4-carbonyl]-amino}-5-(5'-chloro-2'-fluorobiphenyl-4-yl)-2-hydroxypentanoic Acid

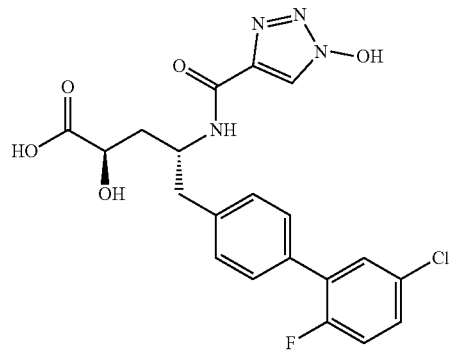

134

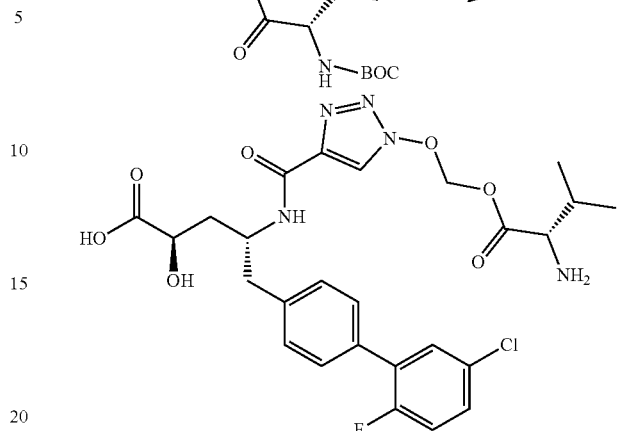

(S)-2-t-Butoxycarbonylamino-3-methylbutyric acid chloromethyl ester (44.4 mg, 167 µmol) was added to a solution of (2R,4R)-5-(5'-chloro-2'-fluorobiphenyl-4-yl)-2-hydroxy-4-[(1-hydroxy-1H-1,2,3-triazole-4-carbonyl)amino]pentanoic acid (30.0 mg, 66.8 µmol) in acetone (0.5 mL, 6.8 mmol). Et₃N (18.6 µL, 134 µmol) was added and the resulting mixture was stirred at 65° C. for 2 hours. 1:1 TFA/DCM (1.0 mL, 6.2 mmol) was added and the mixture was stirred at room temperature for 30 minutes, and then concentrated in vacuo to yield a yellow liquid. The crude liquid was purified (preparative scale C18 column chromatography, small column, using 30-90% MeCN in water with 0.05% TFA) to yield the title compound as a white solid (10 mg). MS m/z [M+H]⁺ calc'd for C₂₆H₂₉ClFN₅O₇, 578.17; found 578.1.

Example 8G: (2R,4R)-5-(5'-Chloro-2'-fluorobiphenyl-4-yl)-2-hydroxy-4-{[1-((S)-2-methoxycarbonylamino-3-methylbutyryloxymethoxy)-1H-[1,2,3]triazole-4-carbonyl]amino}pentanoic Acid

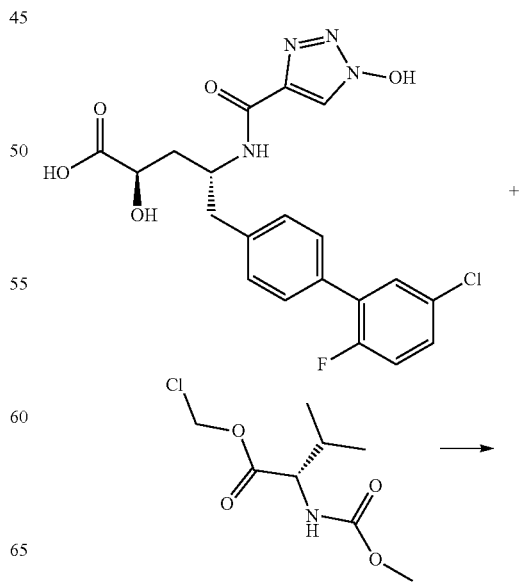

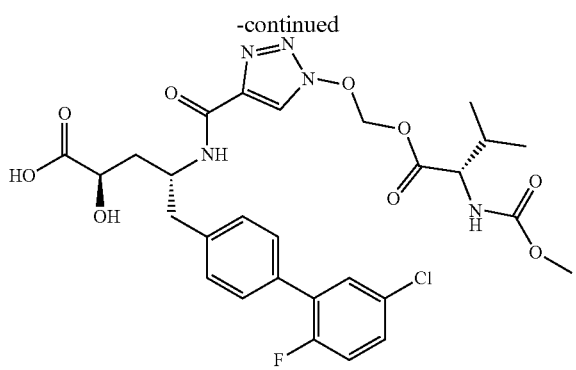

(S)-2-Methoxycarbonylamino-3-methylbutyric acid chloromethyl ester (37.4 mg, 167 μmol) was added to a solution of (2R,4R)-5-(5'-chloro-2'-fluorobiphenyl-4-yl)-2-hydroxy-4-[(1-hydroxy-1H-1,2,3-triazole-4-carbonyl)amino]pentanoic acid (30.0 mg, 66.8 μmol) in acetone (0.5 mL, 6.8 mmol). Et₃N (18.6 μL, 134 μmol) was added and the resulting mixture was stirred at 65° C. for 2 hours. The mixture was then concentrated in vacuo to yield a yellow liquid. The crude liquid was purified (preparative scale C18 column chromatography, small column, using 30-90% MeCN in water with 0.05% TFA) to yield the title compound as a white solid (8.2 mg). MS m/z [M+H]⁺ calc'd for C₂₈H₃₁ClFN₅O₉, 636.18; found 636.1.

Example 8H: (2R,4R)-5-(5'-Chloro-2'-fluorobiphenyl-4-yl)-2-hydroxy-4-[(1-hydroxy-1H-[1,2,3]triazole-4-carbonyl)amino]pentanoic Acid Butyryloxymethyl Ester DIPEA (35.8 μL, 206 μmol) was added to a solution of (2R,4R)-4-amino-5-(5'-chloro-2'-fluorobiphenyl-4-yl)-2-hydroxypentanoic acid butyryloxymethyl ester (30.0 mg, 68.5 μmol, 1-hydroxy-1H-1,2,3-triazole-4-carboxylic acid (13.3 mg, 103 μmol) and HATU (39.1 mg, 103 μmol) in DMF (500 μL, 6.5 mmol). The resulting mixture was stirred at room temperature for 30 minutes, then concentrated in vacuo to yield a clear yellow liquid. The crude liquid was purified by preparative scale HPLC (C18 column chromatography, small column, using 30-90% MeCN in water with 0.05% TFA) to yield the title compound as a white solid (9.0 mg). MS m/z [M+H]⁺ calc'd for C₂₅H₂₆ClFN₄O₇, 549.15; found 549.1.

Example 81: (2R,4R)-5-(5'-chloro-2'-fluorobiphenyl-4-yl)-2-hydroxy-4-[(1-hydroxy-1H-[1,2,3]triazole-4-carbonyl)amino]pentanoic Acid Ethoxycarbonyloxymethyl Ester

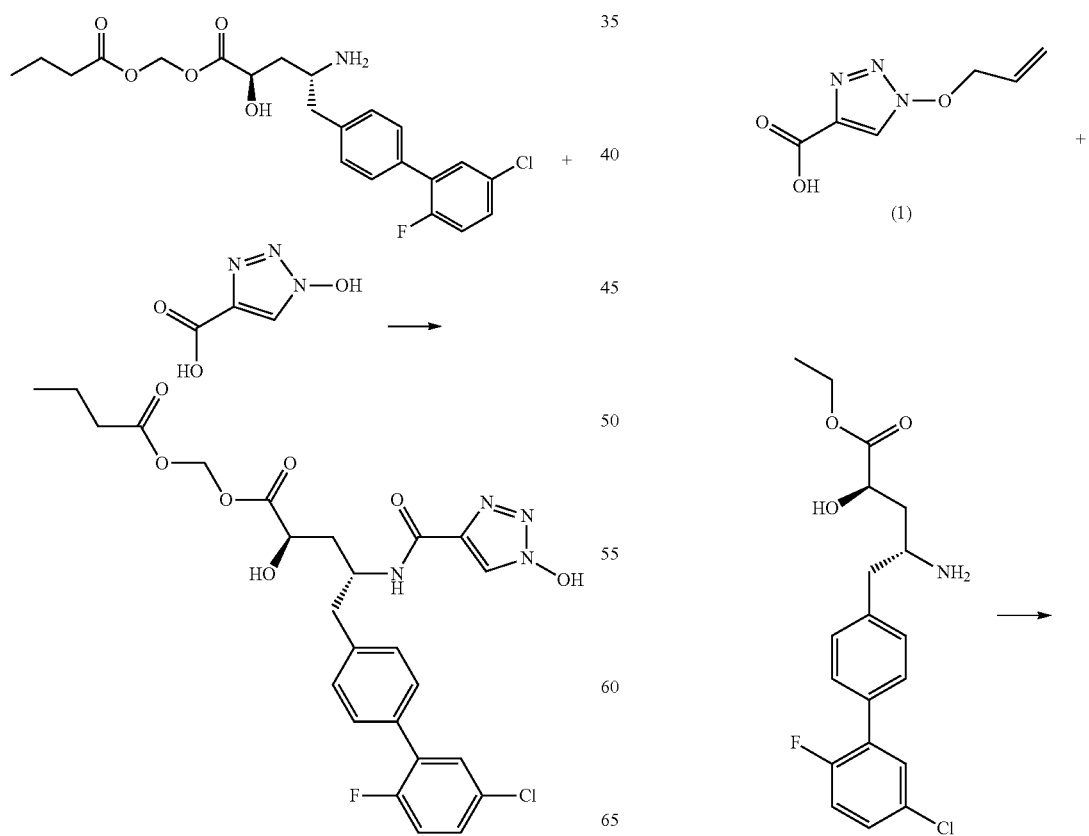

-continued

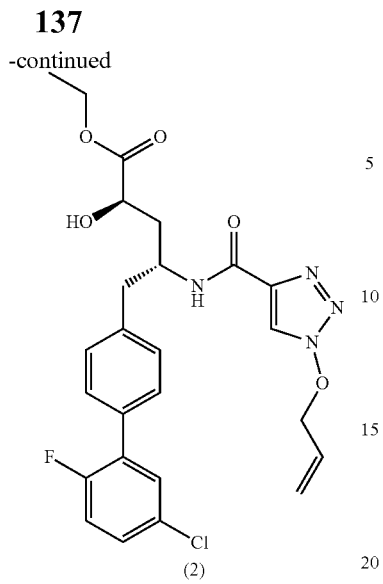

(2)

To a solution of 1-allyloxy-1H-[1,2,3]triazole-4-carboxylic acid ethyl ester (1.7 g, 8.6 mmol) in MeOH (20 mL) was added a solution of LiOH (1.1 g, 45.3 mmol) in water (4 mL). The mixture was stirred at room temperature until the reaction was complete (1 hour). The mixture was concentrated, diluted with water (10 mL), and extracted with EtOAc (2×20 mL). The aqueous layer was acidified by 1N HCl to pH=3, extracted with EtOAc (3×30 mL), and the combined organic layers were washed with saturated aqueous NaCl (30 mL) and dried over anhydrous $Na_2SO_4$. The solution was evaporated to yield Compound 1 (1.3 g) as a white solid. LC-MS: 170 [M+H]$^+$.

To a solution of (2R,4R)-4-amino-5-(5'-chloro-2'-fluoro-biphenyl-4-yl)-2-hydroxypentanoic acid ethyl ester (HCl salt) (800 mg, 2.0 mmol) and Compound 1 (337 mg, 2.0 mmol) in DMF (15 mL) were added PyBOP (1.0 g, 2.0 mmol) and DIPEA (987 µL, 6.0 mmol) at 0° C. The mixture was stirred at room temperature for 4 hours. Water (50 mL) was added, and the mixture was extracted with EtOAc (3×10 mL), and the combined organic layers were washed with saturated aqueous NaCl and dried over anhydrous $Na_2SO_4$. The solution was concentrated to give a crude product which was purified by silica gel chromatography (silica gel: 200-300 mesh; eluted with PE:EtOAc=10:1 to 5:1 to 1:1) to yield Compound 2 (700 mg) as a light yellow solid. LC-MS: 517 [M+H]$^+$.

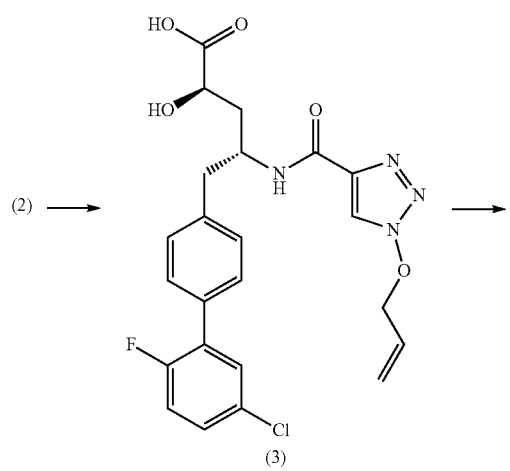

(2) →          (3)

-continued

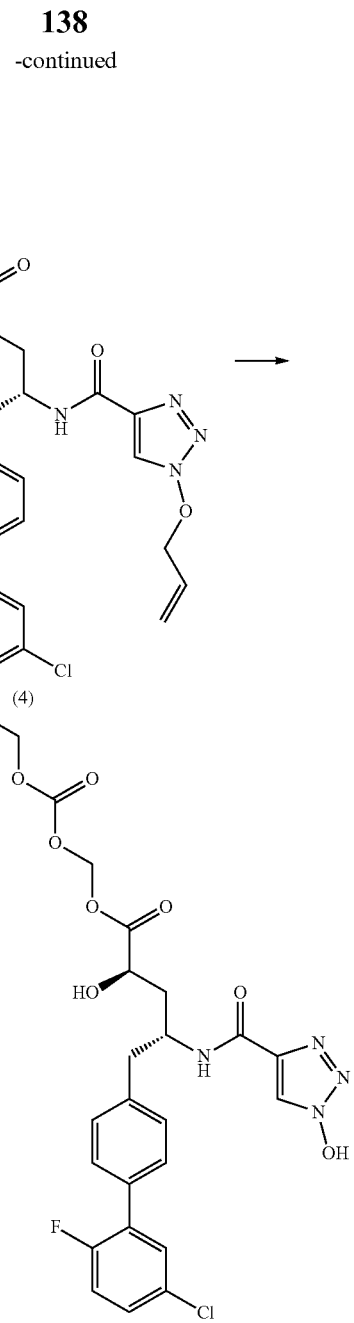

(4)

To a solution of Compound 2 (700 mg, 1.4 mmol) in MeOH (15 mL) and water (3 mL) was added LiOH (171 mg, 4.1 mmol) at room temperature. The mixture was stirred at room temperature overnight. The mixture was concentrated, water (20 mL) was added, and the mixture was extracted with EtOAc (2×10 mL). The aqueous layer was acidified by 1N HCl to pH=3, extracted with EtOAc (3×10 mL), and the combined organic layers were washed with saturated aqueous NaCl (30 mL) and dried over anhydrous $Na_2SO_4$. The solution was evaporated to yield Compound 3 (650 mg) as a yellow solid. LC-MS: 489 [M+H]$^+$.

To a mixture of Compound 3 (80 mg, 160 µmol) and chloromethyl ethyl carbonate (1.0 ml) were added NaI (48 mg, 0.32 mmol) and lutidine (52 mg, 480 µmol). The mixture was stirred at 50° C. for 6 hours. The mixture was then cooled to room temperature, diluted with water (15 ml), and extracted with EtOAc (2×15 mL). The combined organic layers were washed with saturated aqueous NaCl (20 mL), dried over anhydrous Na$_2$SO$_4$, concentrated, and purified by silica gel chromatography (silica gel: 200-300 mesh; elute with PE:EtOAc from 4:1 to 1:1) to yield Compound 4 (60 mg) as a light yellow solid. LC-MS: 591 [M+H]$^+$.

To a solution of Compound 4 (40 mg, 68 μmol) in MeCN (10 mL) was added NaI (10 mg, 68 μmol), and the mixture was stirred at room temperature for 5 minutes. To this stirred suspension, TMSCl (11 mg, 102 μmol) was added and stirred for another 10 minutes. The reaction was quenched by sodium thiosulphate and the mixture was extracted with EtOAc (2×10 mL). The combined organic layers were washed with saturated aqueous NaCl (20 mL) and dried over anhydrous Na$_2$SO$_4$. The residue was purified by pre-HPLC [Daisogel-C18, 250×50 mm, 10 μm; CAN-H$_2$O (0.1% TFA) from 60% to 90%] to yield the title compound (8 mg) as a white solid. LC-MS: 551 [M+H]$^+$. $^1$H-NMR (CDCl$_3$, 400 Hz): δ 1.27 (t, 3H), 2.06-2.11 (m, 1H), 2.14-2.24 (m, 1H), 2.96-3.01 (m, 2H), 4.18 (q, 2H), 4.42 (m, 1H), 4.71 (m, 1H), 5.57-5.65 (m, 2H), 7.05 (t, 1H), 7.22-7.24 (m, 2H), 7.35-7.40 (m, 4H), 8.04 (s, 1H).

Example 8J: (2R,4R)-5-(5'-Chloro-Z-fluorobiphenyl-4-yl)-2-hydroxy-4-[(1-hydroxy-1H-[1,2,3]triazole-4-carbonyl)amino]pentanoic Acid Isopropoxycarbonyloxymethyl Ester

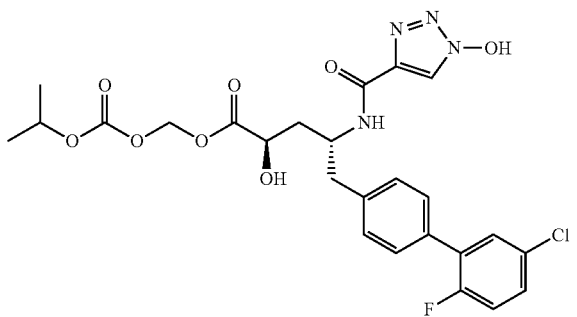 [SMILES: CC(C)OC(=O)OCOC(=O)[C@H](O)C[C@@H](Cc1ccc(-c2cc(Cl)ccc2F)cc1)NC(=O)c1cn(O)nn1]

The title compound was prepared (110 mg) using the procedures described herein.

Example 8K: (2R,4R)-5-(5'-Chloro-2'-fluorobiphenyl-4-yl)-2-hydroxy-4-[(1-hydroxy-1H-[1,2,3]triazole-4-carbonyl)amino]pentanoic Acid 1-Cyclohexyloxycarbonyloxyethyl Ester

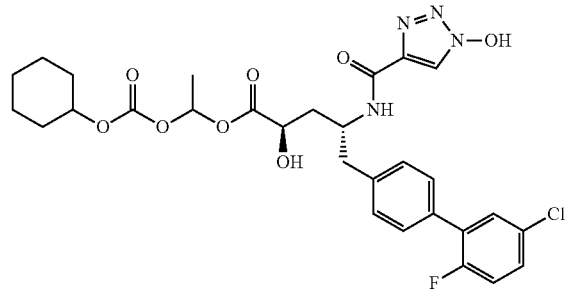 [SMILES: CC(OC(=O)OC1CCCCC1)OC(=O)[C@H](O)C[C@@H](Cc1ccc(-c2cc(Cl)ccc2F)cc1)NC(=O)c1cn(O)nn1]

The title compound was prepared (16.6 mg) using the procedures described herein.

Example 8L: (2R,4R)-5-(5'-Chloro-2'-fluorobiphenyl-4-yl)-2-hydroxy-4-[(1-hydroxy-1H-[1,2,3]triazole-4-carbonyl)amino]pentanoic acid (S)-2-methoxycarbonylamino-3-methyl-butyryloxymethyl Ester

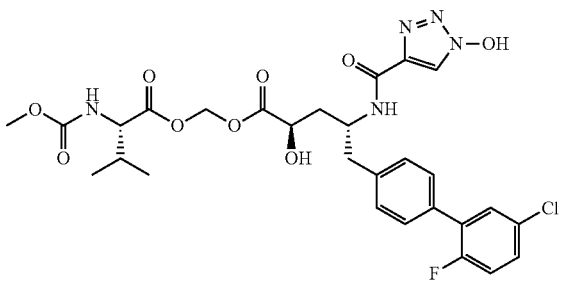 [SMILES: COC(=O)N[C@H](C(=O)OCOC(=O)[C@H](O)C[C@@H](Cc1ccc(-c2cc(Cl)ccc2F)cc1)NC(=O)c1cn(O)nn1)C(C)C]

The title compound was prepared (117 mg) using the procedures described herein.

Example 8M: (2R,4R)-5-(5'-Chloro-2'-fluorobiphenyl-4-yl)-2-hydroxy-4-[(1-hydroxy-1H-[1,2,3]triazole-4-carbonyl)amino]pentanoic Acid Acetoxymethyl Ester

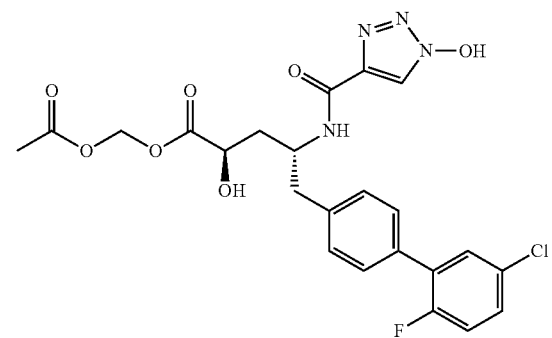 [SMILES: CC(=O)OCOC(=O)[C@H](O)C[C@@H](Cc1ccc(-c2cc(Cl)ccc2F)cc1)NC(=O)c1cn(O)nn1]

Using the procedures described herein, the title compound can also be prepared.

Example 9A: (2R,4R)-5-(3'-Chlorobiphenyl-4-yl)-2-hydroxy-4-[(5-oxo-1-phenyl-4,5-dihydro-1H-[1,2,4]triazole-3-carbonyl)amino]pentanoic Acid

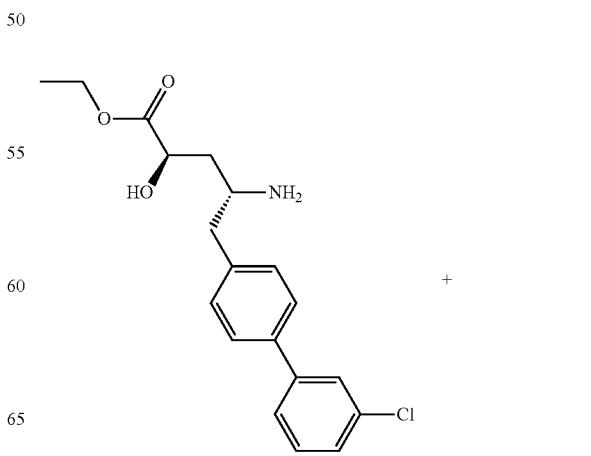

+

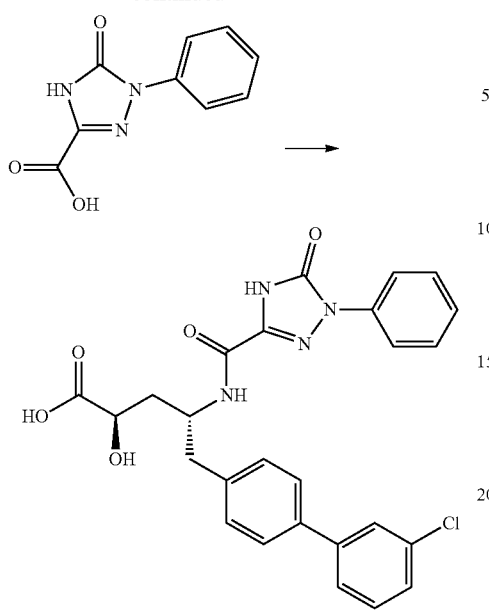

5-Oxo-1-phenyl-4,5-dihydro-1H-[1,2,4]triazole-3-carboxylic acid (42.3 mg, 206 μmol) and HCTU (128 mg, 310 μmol) were combined in DMF, and stirred for 10 minutes at room temperature. DIPEA (72 μL, 413 μmol) and (2R,4R)-4-amino-5-(3'-chlorobiphenyl-4-yl)-2-hydroxypentanoic acid ethyl ester (50 mg, 0.1 mmol) were added, and the resulting mixture was stirred at room temperature overnight. The mixture was combined with EtOH (402 μL, 6.9 mmol) and 1 M LiOH in water (1.1 mL, 1.1 mmol). The mixture was stirred at room temperature for 1 hour, evaporated under reduced pressure, and purified by preparative HPLC to yield the title compound (1.8 mg) as a TFA salt. MS m/z [M+H]+ calc'd for $C_{26}H_{23}ClN_4O_5$, 507.14; found 507.2.

Example 9B: (2R,4R)-5-(3'-Chlorobiphenyl-4-yl)-2-hydroxy-4-[(5-oxo-1-phenyl-4,5-dihydro-1H-[1,2,4]triazole-3-carbonyl)amino]pentanoic Acid Ethoxycarbonyloxymethyl Ester

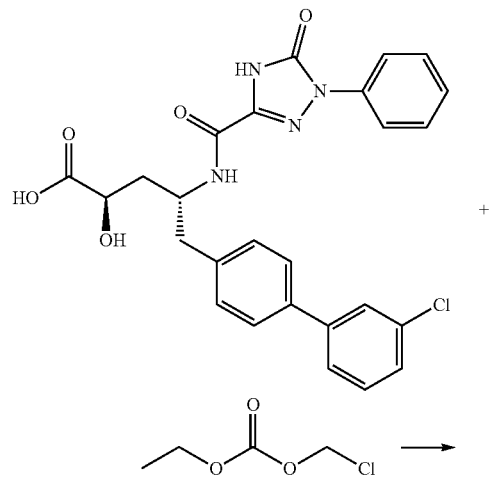

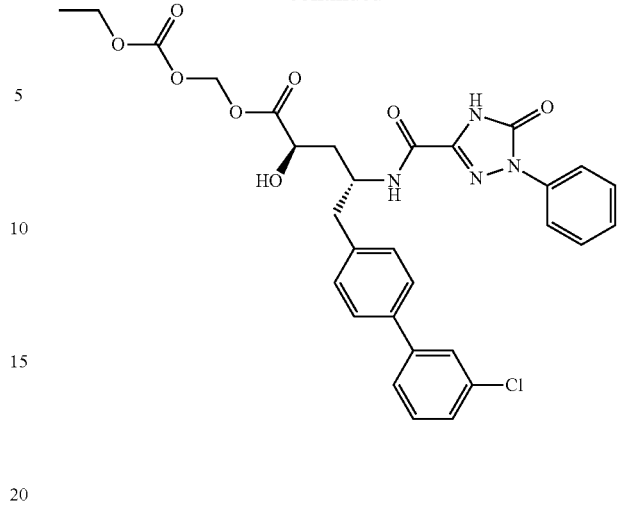

A solution of (2R,4R)-5-(3'-chlorobiphenyl-4-yl)-2-hydroxy-4-[(5-oxo-1-phenyl-4,5-dihydro-1H-[1,2,4]triazole-3-carbonyl)amino]pentanoic acid (253 mg, 0.5 mmol), chloromethyl ethyl carbonate (69 mg, 0.5 mmol), 2,6-lutidine (165 mg, 1.5 mmol) and NaI (150 mg, 1 mmol) in DMF (20 mL) was stirred for 15 hours at 50° C. The mixture was quenched with water (20 mL) and extracted with EtOAc (3×30 mL). The combined organic layers were collected and concentrated in vacuo. The residue was purified by column chromatography (petroleum ether/EtOAc=3:1) to yield the title compound as a white solid (13 mg). LC-MS: 608.8 [M+H]+. 1H NMR: (CDCl3, 400 MHz) δ 1.27 (t, J=8.0 Hz, 3H), 2.03-2.33 (m, 2H), 3.02-3.05 (m, 2H), 4.18 (q, J=8.0 Hz, 2H), 4.49 (br, 1H), 4.85 (br, 1H), 5.57-5.76 (m, 2H), 7.03 (d, J=12 Hz, 1H), 7.25-7.40 (m, 4H), 7.42-7.51 (m, 3H), 7.53-7.61 (m, 3H), 7.93 (d, J=8.0 Hz, 2H).

Example 9C: (2R,4R)-5-(3'-Chlorobiphenyl-4-yl)-2-hydroxy-4-[(5-oxo-1-phenyl-4,5-dihydro-1H-[1,2,4]triazole-3-carbonyl)amino]pentanoic acid (S)-2-methoxycarbonylamino-3-methylbutyryloxymethyl Ester

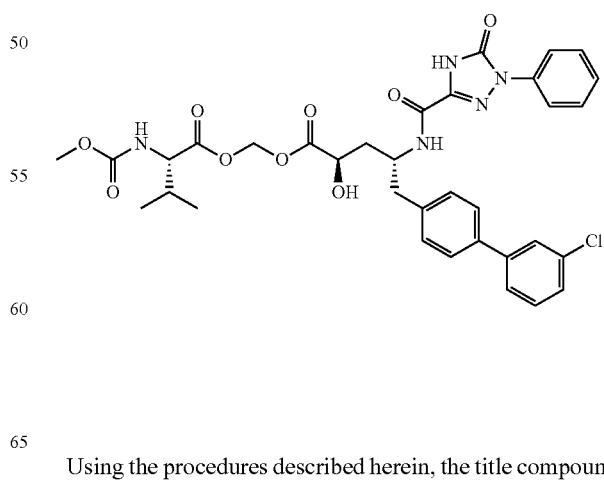

Using the procedures described herein, the title compound can also be prepared.

Example 10A: (2R,4R)-4-[(5-Acetyl-2-phosphonooxymethyl-2H-pyrazole-3-carbonyl)amino]-5-biphenyl-4-yl-2-hydroxypentanoic Acid Ethyl Ester

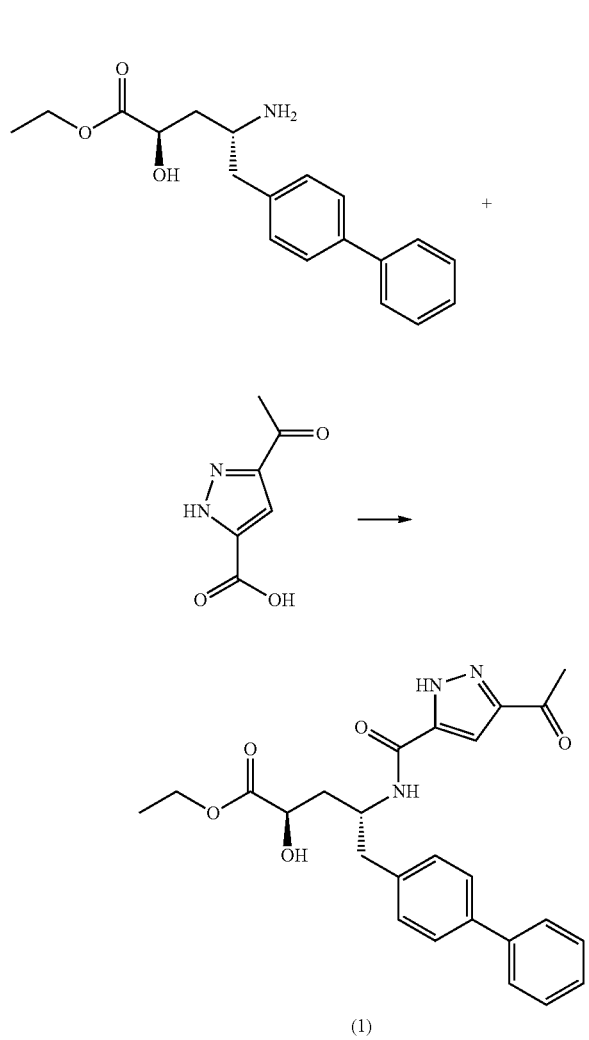

(1)

(2R,4R)-4-Amino-5-biphenyl-4-yl-2-hydroxypentanoic acid ethyl ester (HCl salt; 500 mg, 1 mmol, 1.0 eq.), 5-acetyl-2H-pyrazole-3-carboxylic acid (330.4 mg, 2.1 mmol, 1.5 eq.), and HATU (820 mg, 2.1 mmol, 1.5 eq.) were combined in DMF (5 mL), and the resulting mixture was stirred for 2 minutes. DIPEA (750 µL) was added and the mixture was stirred for 1 hour. The mixture was dried under vacuum, and the product was purified using reverse phase chromatography (10-70% MeCN/H$_2$O; 0.05% TFA over 70 minutes) to yield Compound 1 as a TFA salt (300 mg, purity 98%). MS m/z [M+H]$^+$ calc'd for C$_{25}$H$_{27}$N$_3$O$_5$, 450.20; found 450.2.

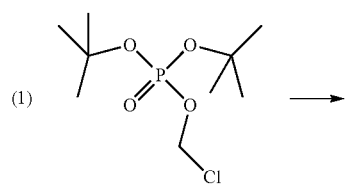

(1)

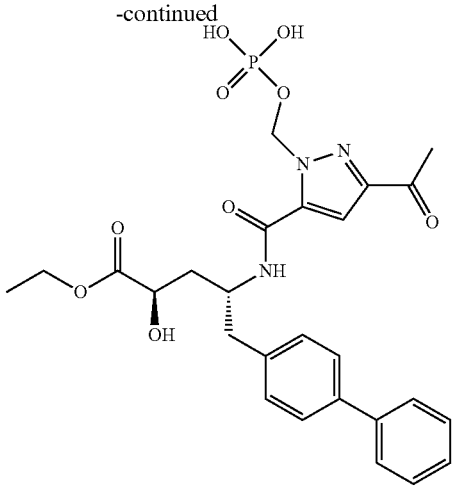

To a solution of Compound 1 (15.0 mg, 33.4 µmol) in DMF (103 µL, 1.3 mmol) was added K$_2$CO$_3$ (5.1 mg, 36.7 µmol) and phosphoric acid di-t-butyl ester chloromethyl ester (9.50 mg, 36.7 µmol). The resulting mixture was stirred at room temperature overnight, then evaporated under reduced pressure. The residue was diluted in EtOAc and a solution of 1M HCl was added to bring the pH to 4-5. The organic layer was extracted twice with EtOAc, washed with water followed by saturated aqueous NaCl, dried over anhydrous MgSO$_4$, filtered, and evaporated. The residue was purified by flash chromatography (30-90% EtOAc in hexanes). DCM (64.2 µL, 1.0 mmol) was added, followed by TFA (40 µL, 0.6 mmol), and the resulting mixture was stirred at room temperature for 20 minutes. The mixture was evaporated and purified by purified by preparative HPLC to yield the title compound as a TFA salt (4 mg). MS m/z [M+H]$^+$ calc'd for C$_{26}$H$_{30}$H$_3$O$_9$P, 560.17; found 560.1.

Example 10B: (2R,4R)-4-[(5-Acetyl-2H-pyrazole-3-carbonyl)amino]-2-((S)-2-amino-3-methylbutyryloxy)-5-biphenyl-4-yl-pentanoic Acid Ethyl Ester

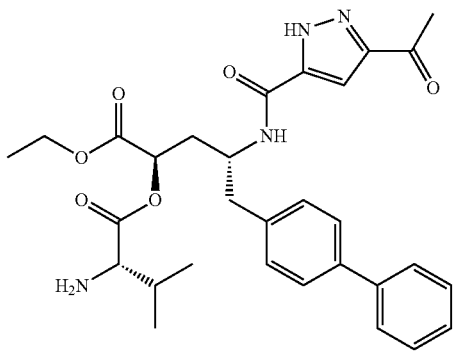 [SMILES: CCOC(=O)[C@@H](C[C@@H](Cc1ccc(-c2ccccc2)cc1)NC(=O)c1cc(C(C)=O)n[nH]1)OC(=O)[C@@H](N)C(C)C]

Using the procedures described herein, the title compound can also be prepared.

Example 10C: (2R,4R)-4-{[5-Acetyl-2-((S)-2-amino-3-methylbutyryloxymethyl)-2H-pyrazole-3-carbonyl]amino}-5-biphenyl-4-yl-2-hydroxypentanoic Acid Ethyl Ester

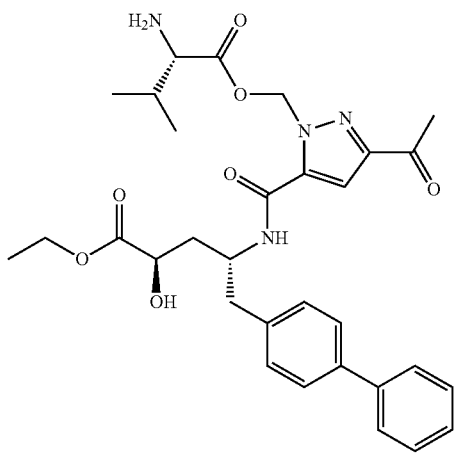 [SMILES: CCOC(=O)[C@H](O)C[C@@H](Cc1ccc(-c2ccccc2)cc1)NC(=O)c1cc(C(C)=O)nn1COC(=O)[C@@H](N)C(C)C]

Using the procedures described herein, the title compound can also be prepared.

Example 11A: (2R,4R)-5-(3'-Chlorobiphenyl-4-yl)-2-hydroxy-4-[(1H-tetrazole-5-carbonyl)amino]pentanoic Acid Ethoxycarbonyloxymethyl Ester

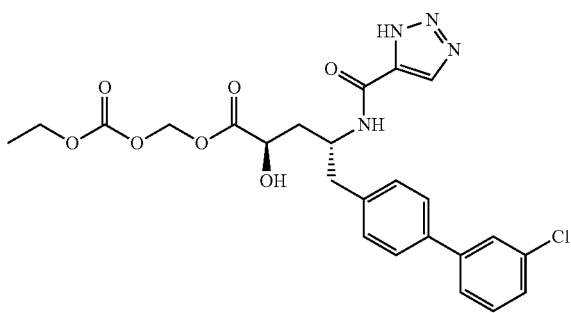 [SMILES: CCOC(=O)OCOC(=O)[C@H](O)C[C@@H](Cc1ccc(-c2cccc(Cl)c2)cc1)NC(=O)c1cnn[nH]1]

Using the procedures described herein, the title compound can also be prepared.

ASSAY

In Vitro Assays for the Quantitation of Inhibitor Potencies (IC$_{50}$) at Human and Rat NEP, and Human ACE The inhibitory activities of compounds at human and rat neprilysin (EC 3.4.24.11; NEP) and human angiotensin converting enzyme (ACE) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl) aminomethane (Tris) pH 7.5; Bordier (1981) *J. Biol. Chem.* 256: 1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

ENZYME INHIBITION ASSAYS

Recombinant human NEP and recombinant human ACE were obtained commercially (R&D Systems, Minneapolis, Minn., catalog numbers 1182-ZN and 929-ZN, respectively). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) and Abz-Phe-Arg-Lys(Dnp)-Pro-OH (Araujo et al. (2000) *Biochemistry* 39:8519-8525; Bachem, Torrance, Calif.) were used in the NEP and ACE assays respectively.

The assays were performed in 384-well white opaque plates at 37° C. using the fluorogenic peptide substrates at a concentration of 10 μM in Assay Buffer (NEP: 50 mM HEPES, pH 7.5, 100 mM NaCl, 0.01% polyethylene glycol sorbitan monolaurate (Tween-20), 10 μM ZnSO$_4$; ACE: 50 mM HEPES, pH 7.5, 100 mM NaCl, 0.01% Tween-20, 1 μM ZnSO$_4$). The respective enzymes were used at concentrations that resulted in quantitative proteolysis of 1 μM of substrate after 20 minutes at 37° C.

Test compounds were assayed over the range of concentrations from 10 μM to 20 pM. Test compounds were added to the enzymes and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively. Inhibition constants were obtained by nonlinear regression of the data using the equation (GraphPad Software, Inc., San Diego, Calif.):

$$v = v_0/[1+(I/K')]$$

where v is the reaction rate, $v_0$ is the uninhibited reaction rate, I is the inhibitor concentration and K' is the apparent inhibition constant.

The compound of formula I' (Example 1A) was tested in this assay and found to have a pK$_i$ value at human NEP of ≥9.0, and the following prodrugs were also found to have activity:

| Ex. | pK$_i$ |
| --- | --- |
| 1G | ≥9.0 |
| 1I | 7.0-7.9 |

-continued

| Ex. | pK$_i$ |
|---|---|
| 1L | ≥9.0 |
| 1M | 8.0-8.9 |

The prodrug compounds of Examples 1B-F, 1H, 1J-K and 1N-P were not tested since activity would not be expected in this in vitro assay; however, based upon the activity of the active form, the prodrugs are expected to have in vivo NEP activity.

The compound of formula II' (Example 2A) was tested in this assay and found to have a pK$_i$ value at human NEP of ≥9.0. The prodrug compounds of Examples 2B-I either did not inhibit the enzyme in this in vitro assay, or were not tested since activity would not be expected in this assay; however, based upon the activity of the active form, the prodrugs are expected to have in vivo NEP activity.

The compound of formula III' (Example 3A) was tested in this assay and found to have a pK$_i$ value at human NEP of ≥9.0. The prodrug compounds of Examples 3B-E either did not inhibit the enzyme in this in vitro assay, or were not tested since activity would not be expected in this assay; however, based upon the activity of the active form, the prodrugs are expected to have in vivo NEP activity.

The following compounds of the invention were tested in this assay and found to have pK$_i$ values at human NEP as follows. In general, either the prodrug compounds did not inhibit the enzyme in this in vitro assay, or the prodrugs were not tested (n.d.) since activity would not be expected.

| Ex. | pK$_i$ |
|---|---|
| 4A | n.d. |
| 4B | ≥9.0 |
| 5A | n.d. |
| 5B | ≥9.0 |
| 6A | ≥9.0 |
| 6B | n.d. |
| 6C | n.d. |
| 6D | n.d. |
| 6E | n.d. |

The compound of formula VII' (Example 7A) was tested in this assay and found to have a pK$_i$ value at human NEP of ≥9.0. The prodrug compounds of Examples 7B-E either did not inhibit the enzyme in this in vitro assay, or were not tested since activity would not be expected in this assay; however, based upon the activity of the active form, the prodrugs are expected to have in vivo NEP activity.

The compound of formula VIII' (Example 8A) was tested in this assay and found to have a pK$_i$ value at human NEP of ≥9.0. The prodrug compounds of Examples 8B-L either did not inhibit the enzyme in this in vitro assay, or were not tested since activity would not be expected in this assay; however, based upon the activity of the active form, the prodrugs are expected to have in vivo NEP activity. The prodrug compounds of Example 81 are expected to have in vivo NEP activity.

The compound of formula IX' (Example 9A) was tested in this assay and found to have a pK$_i$ value at human NEP of ≥9.0. The prodrug compounds of Examples 9B-C either did not inhibit the enzyme in this in vitro assay, or were not tested since activity would not be expected in this assay; however, based upon the activity of the active form, the prodrugs are expected to have in vivo NEP activity.

The compound of formula X' was tested in this assay and found to have a pK$_i$ value at human NEP of ≥9.0. The prodrug compound of Example 10A either did not inhibit the enzyme in this in vitro assay, or was not tested since activity would not be expected in this assay; however, based upon the activity of the active form, this prodrug is expected to have in vivo NEP activity.

The prodrug compound of Example 11A either did not inhibit the enzyme in this in vitro assay, or was not tested since activity would not be expected in this assay; however, this prodrug is expected to have in vivo NEP activity.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A compound of:
   (a) (2R,4R)-5-(3'-chlorobiphenyl-4-yl)-4-{[3-(2-fluorophenyl)isoxazole-5-carbonyl]amino}-2-hydroxypentanoic acid;
   (b) (2R,4R)-5-(3'-chlorobiphenyl-4-yl)-4-{[3-(2-fluorophenyl)isoxazole-5-carbonyl]amino}-2-hydroxypentanoic acid ethoxycarbonyloxymethyl ester;
   (c) (2R,4R)-5-(3'-chlorobiphenyl-4-yl)-4-{[3-(2-fluorophenyl)isoxazole-5-carbonyl]amino}-2-hydroxypentanoic acid isopropoxycarbonyloxymethyl ester;
   (d) (2R,4R)-5-(3'-chlorobiphenyl-4-yl)-4-{[3-(2-fluorophenyl)isoxazole-5-carbonyl]amino}-2-hydroxypentanoic acid acetoxymethyl ester;
   (e) (2R,4R)-5-(3'-chlorobiphenyl-4-yl)-4-{[3-(2-fluorophenyl)isoxazole-5-carbonyl]amino}-2-hydroxypentanoic acid (S)-2-methoxycarbonylamino-3-methylbutyryloxymethyl ester; or
   a pharmaceutically-acceptable salt thereof.

2. A pharmaceutical composition comprising a pharmaceutically acceptable carrier and the compound of claim 1.

3. A method for treating hypertension, heart failure, or renal disease, comprising administering to a patient a therapeutically effective amount of the compound of claim 1.

* * * * *